(12) United States Patent
Shoseyov et al.

(10) Patent No.: US 10,716,876 B2
(45) Date of Patent: Jul. 21, 2020

US010716876B2

(54) METHOD OF GENERATING COLLAGEN FIBERS

(71) Applicant: CollPlant Ltd., Ness Ziona (IL)

(72) Inventors: Oded Shoseyov, Karmei Yosef (IL); Amit Yaari, Kibbutz Ein Dor (IL)

(73) Assignee: CollPlant Ltd., Rehovot (IL)

( * ) Notice: Subject to any disclaimer, the term of this patent is extended or adjusted under 35 U.S.C. 154(b) by 28 days.

(21) Appl. No.: 15/867,783

(22) Filed: Jan. 11, 2018

(65) Prior Publication Data

US 2018/0193524 A1 Jul. 12, 2018

Related U.S. Application Data

(60) Provisional application No. 62/445,333, filed on Jan. 12, 2017.

(51) Int. Cl.

| *A61L 27/24* | (2006.01) |
|---|---|
| *C07K 14/78* | (2006.01) |
| *A61L 27/38* | (2006.01) |
| *A61K 8/65* | (2006.01) |
| *D01F 4/00* | (2006.01) |
| *D01D 5/06* | (2006.01) |
| *A61Q 19/00* | (2006.01) |
| *A61L 27/56* | (2006.01) |
| *D01D 5/16* | (2006.01) |
| *D01F 11/02* | (2006.01) |

(52) U.S. Cl.
CPC .............. *A61L 27/24* (2013.01); *A61K 8/65* (2013.01); *A61L 27/38* (2013.01); *A61L 27/56* (2013.01); *A61Q 19/00* (2013.01); *C07K 14/78* (2013.01); *D01D 5/06* (2013.01); *D01D 5/16* (2013.01); *D01F 4/00* (2013.01); *A61K 2800/10* (2013.01); *D01F 11/02* (2013.01); *D10B 2211/06* (2013.01); *D10B 2509/00* (2013.01)

(58) Field of Classification Search
CPC .......... A61L 27/26; A61L 27/18; A61L 27/34; A61L 29/085; A61L 31/10; A61L 27/54; A61L 31/06; A61L 27/3804; A61L 27/48; A61L 27/50; A61L 31/14; A61L 31/16; A61L 2400/18; A61L 27/24; A61L 17/00; A61L 2300/00; A61L 27/3895; A61L 27/52; A61L 27/58; A61L 15/26; A61L 2300/252; A61L 2300/414; A61L 27/20; A61L 27/46; A61L 27/60; A61L 31/148; A61L 17/10; A61L 2300/406; A61L 2300/41; A61L 2400/04; A61L 2430/00; A61L 27/225; A61L 27/3808; A61L 27/3826; A61L 27/507; A61L 15/325; A61L 15/64; A61L 17/04; A61L 2300/214; A61L 2300/256; A61L 2300/404; A61L 2300/43; A61L 2300/602; A61L 2400/12; A61L 2430/20; A61L 2430/22; A61L 27/14; A61L 27/3612; A61L 27/3633; A61L 27/3679; A61L 27/3691; A61L 27/38; A61L 27/3813; A61L 27/3834; A61L 27/3873; A61L 27/3882; A61L 27/3886; A61L 27/56; A61L 31/046; A61L 31/128; A23L 13/424; A23L 13/426; A23L 27/26; A23L 13/42; A23L 27/00; A23L 27/10; A23L 27/20; A23L 29/238; A23L 2/66; A23L 33/185; A23L 5/41; A23L 7/109; A61K 47/30; A61K 47/4823; A61K 47/542; A61K 47/549; A61K 47/61; A61K 47/62; A61K 35/12; A61K 47/32; A61K 9/70; A61K 38/00; A61K 38/1825; A61K 38/1841; A61K 38/1883; A61K 38/39; A61K 9/0024

See application file for complete search history.

(56) References Cited

U.S. PATENT DOCUMENTS

| 663,032 | A | 12/1900 | Laughlin | |
|---|---|---|---|---|
| 6,413,742 | B1 * | 7/2002 | Olsen | C07K 14/765 435/69.1 |
| 7,057,023 | B2 | 6/2006 | Islam et al. | |
| 2003/0100739 | A1 | 5/2003 | Tsai et al. | |
| 2003/0129699 | A1 | 7/2003 | Perret et al. | |
| 2006/0159731 | A1 | 7/2006 | Shoshan | |
| 2007/0187862 | A1 | 8/2007 | Kaplan et al. | |
| 2007/0269476 | A1 * | 11/2007 | Voytik-Harbin | A61L 27/24 424/422 |
| 2008/0286244 | A1 | 11/2008 | Cheema et al. | |
| 2009/0069893 | A1 | 3/2009 | Paukshto et al. | |
| 2009/0260646 | A1 | 10/2009 | Masuda | |
| 2011/0121485 | A1 | 5/2011 | Rheinecker et al. | |
| 2012/0273993 | A1 | 11/2012 | Shoseyov et al. | |

(Continued)

FOREIGN PATENT DOCUMENTS

| EP | 0943346 | | 9/1999 | |
|---|---|---|---|---|
| EP | 1674116 | | 6/2006 | |
| GB | 606427 | * | 8/1948 | ............... A51K 9/00 |

(Continued)

OTHER PUBLICATIONS

Advisory Action and Interview Summary dated Nov. 17, 2016 From the US Patent and Trademark Office Re. U.S. Appl. No. 13/511,686. (9 pages).

(Continued)

*Primary Examiner* — Audrea B Coniglio

(57) ABSTRACT

A method of generating a collagen fiber is disclosed. Fibers generated thereby are also disclosed as well as scaffolds comprising such fibers.

24 Claims, 14 Drawing Sheets
(7 of 14 Drawing Sheet(s) Filed in Color)
Specification includes a Sequence Listing.

(56) References Cited

U.S. PATENT DOCUMENTS

2013/0230573 A1    9/2013  Shoseyov et al.

FOREIGN PATENT DOCUMENTS

| GB | 643859 | | 9/1950 | | |
|----|--------|---|--------|---|---|
| JP | 07-097714 | | 4/1995 | | |
| WO | WO 93/06791 | | 4/1993 | | |
| WO | WO 2008/157608 | | 12/2008 | | |
| WO | WO2010/048281 | A1 * | 4/2010 | ............... | A51K 9/00 |
| WO | WO 2012/066543 | | 5/2012 | | |

OTHER PUBLICATIONS

Communication Pursuant to Article 94(3) EPC dated Feb. 10, 2017 From the European Patent Office Re. Application No. 10793058.8. (5 pages).
Communication Pursuant to Article 94(3) EPC dated Apr. 22, 2014 From the European Patent Office Re. Application No. 11799500.1.
International Preliminary Report on Patentability dated Jun. 7, 2012 From the International Bureau of WIPO Re. Application No. PCT/IL2010/000984.
International Preliminary Report on Patentability dated May 30, 2013 From the International Bureau of WIPO Re. Application No. PCT/IL2011/000886.
International Search Report and the Written Opinion dated Mar. 17, 2011 From the International Searching Authority Re. Application No. PCT/IL2010/000984.
International Search Report and the Written Opinion dated Jun. 22, 2012 From the International Searching Authority Re. Application No. PCT/IL2011/000886.
Official Action dated May 19, 2014 From the US Patent and Trademark Office Re. U.S. Appl. No. 13/885,690.
Official Action dated Aug. 27, 2015 From the US Patent and Trademark Office Re. U.S. Appl. No. 13/511,686.
Official Action dated Jun. 28, 2016 From the US Patent and Trademark Office Re. U.S. Appl. No. 13/511,686.
Official Action dated Jan. 29, 2016 From the US Patent and Trademark Office Re. U.S. Appl. No. 13/511,686.
Restriction Official Action dated Sep. 6, 2013 From the US Patent and Trademark Office Re. U.S. Appl. No. 13/885,690.
Restriction Official Action dated Sep. 9, 2014 From the US Patent and Trademark Office Re. U.S. Appl. No. 13/511,686.
Giraud-Guille et al. "Liquid Crystalline Assemblies of Collagen in Bone and in Vitro Systems", Journal of Biomechanics, 36(10): 1571-1579, Oct. 2003.
Kato et al. "Regeneration of Achilles Tendon With a Collagen Tendon Prosthesis. Results of a One-Year Implantation Study", The Journal of Bone and Joint Surgery, XP000202597, 73-A(4): 561-574, Apr. 1, 1991. p. 563, col. 2-p. 564, col. 1, Fig.3A.
Kirkwood et al. "Liquid Crystalline Collagen: A Self-Assembled Morphology for the Orientation of Mammalian Cells", Langmuir, XP002625917, 25(5): 3200-3206, Mar. 3, 2009. p. 3200, cols. 1-2.
Martin et al. "Liquid Cristalline Ordering of Procollagen as a Determinant of Three-Dimensional Extracellular Matrix Architecture", Journal of Molecular Biology, 301(1):11-7, Aug. 4, 2000.
Murthy Liquid Crystallinity in Collagen Solutions and Magnetic Orientation of Collagen Fibrils,Biopolymers, 23:1261-1267, 1984.
Sigma-Aldrich "Collagen Solution From Bovine Skin. BioReagent, Suitable for Cell Culture", Sigma 4243, Datasheet, EC No. 231-791-2, Mar. 31, 2015.
Silver et al. "Viscoelastic Properties of Young and Old Human Dermis: A Proposed Molecular Mechanism for Elastic Energy Storage in Collagen and Elastin", Journal of Applied Polymer Science, 86(8): 1978-1985, Nov. 21, 2002.
Vasilev et al. "Regenerated Collagen Fibres", Fibre Chemistry Fibre and Technology, 3(1): 57-61, Jan. 1972.
Yaari et al. "Liquid Crystalline Human Recombinant Collagen: The Challenge and the Opportunity", Tissue Engineering Part A, 19(13/14): 1502-1506, Published Online Jan. 31, 2013.
Yaari et al. "Wet Spinning and Drawing of Human Recombinant Collagen", ACS Biomaterials Science & Engineering, 2(3): 349-360, Feb. 26, 2016.

* cited by examiner

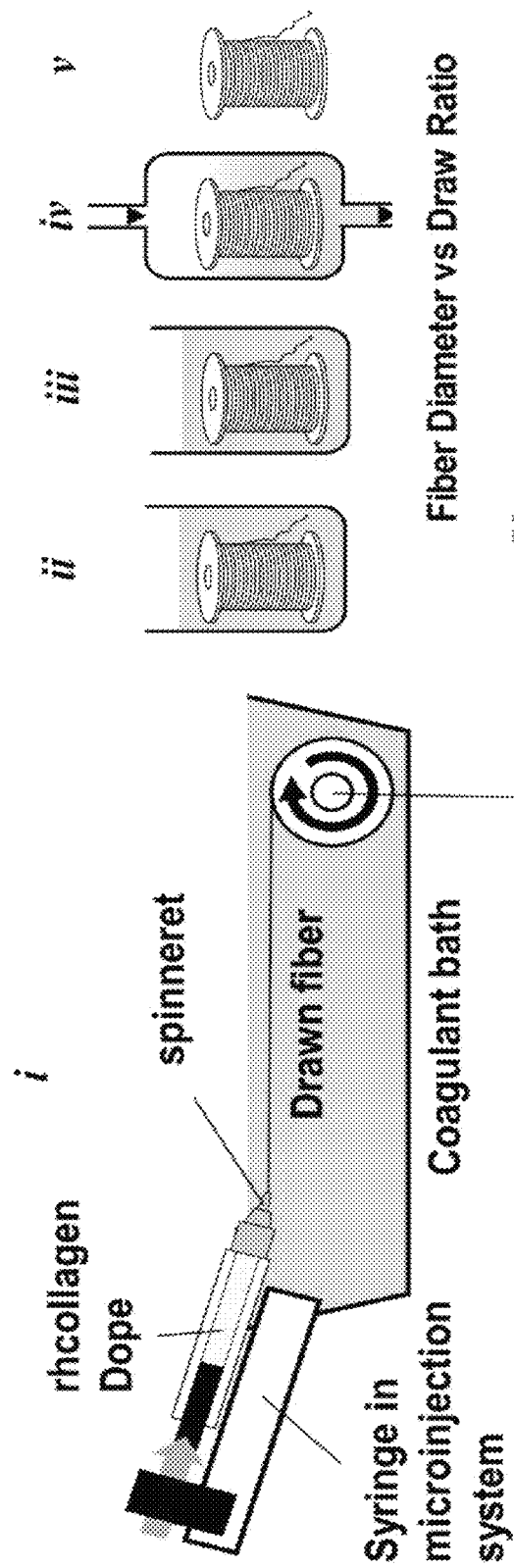
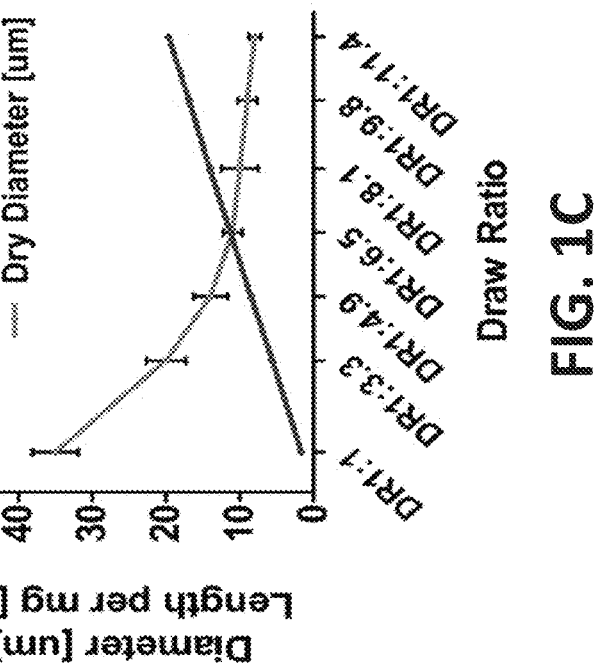
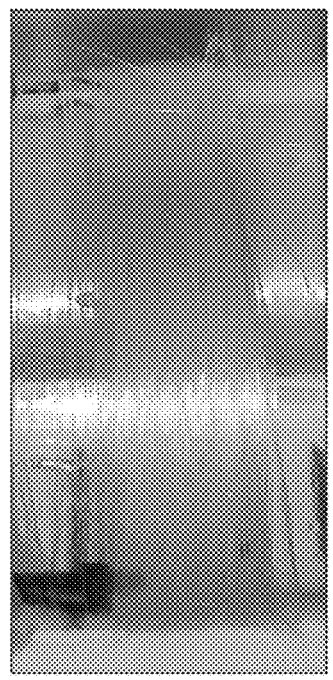
FIG. 1A
FIG. 1B
FIG. 1C

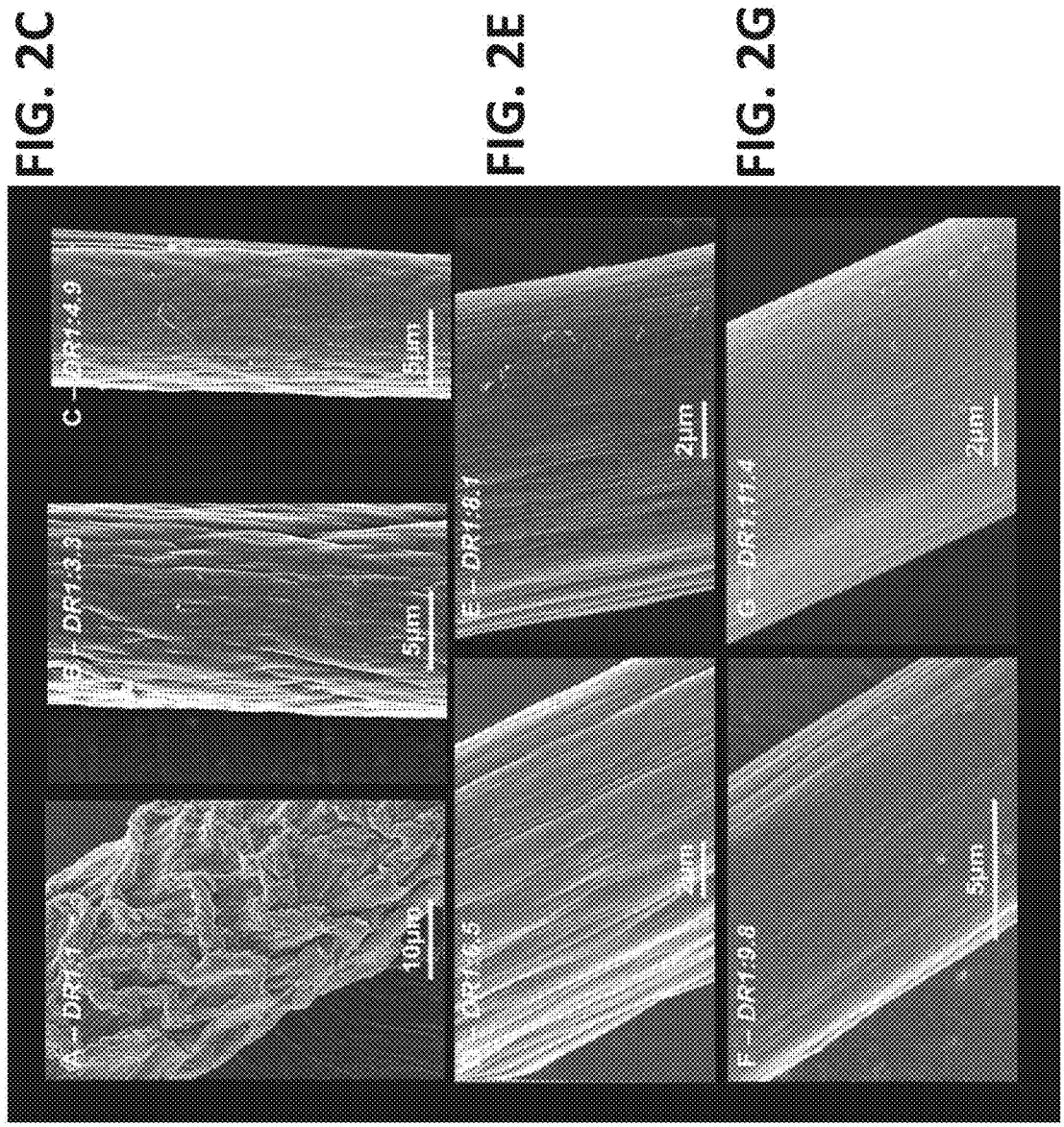

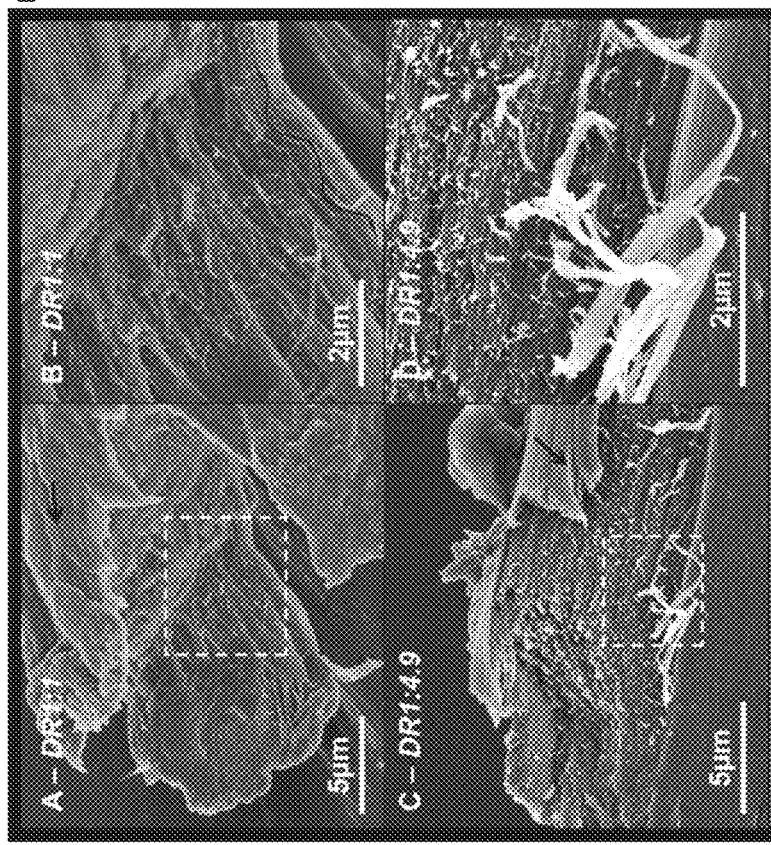

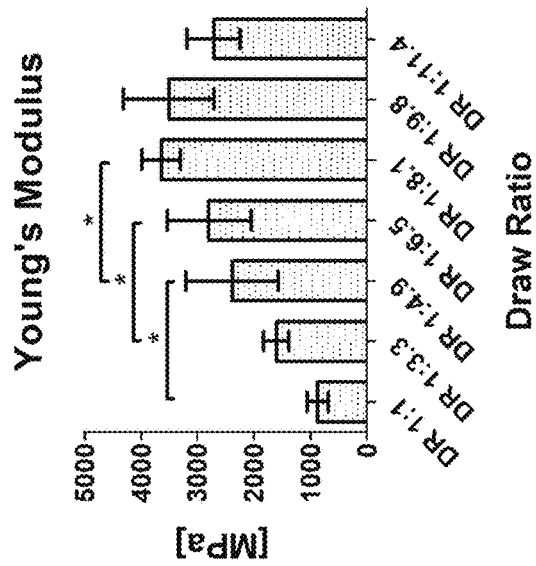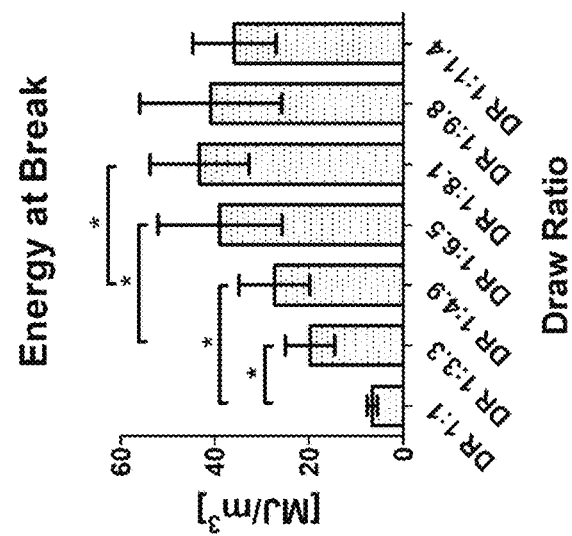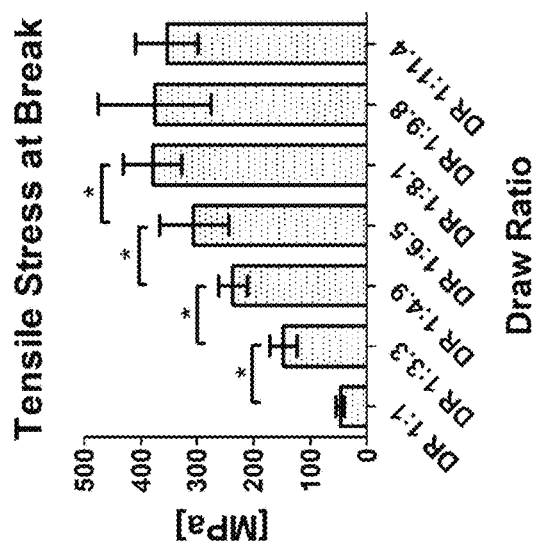
FIG. 5A  FIG. 5B  FIG. 5C  FIG. 5D

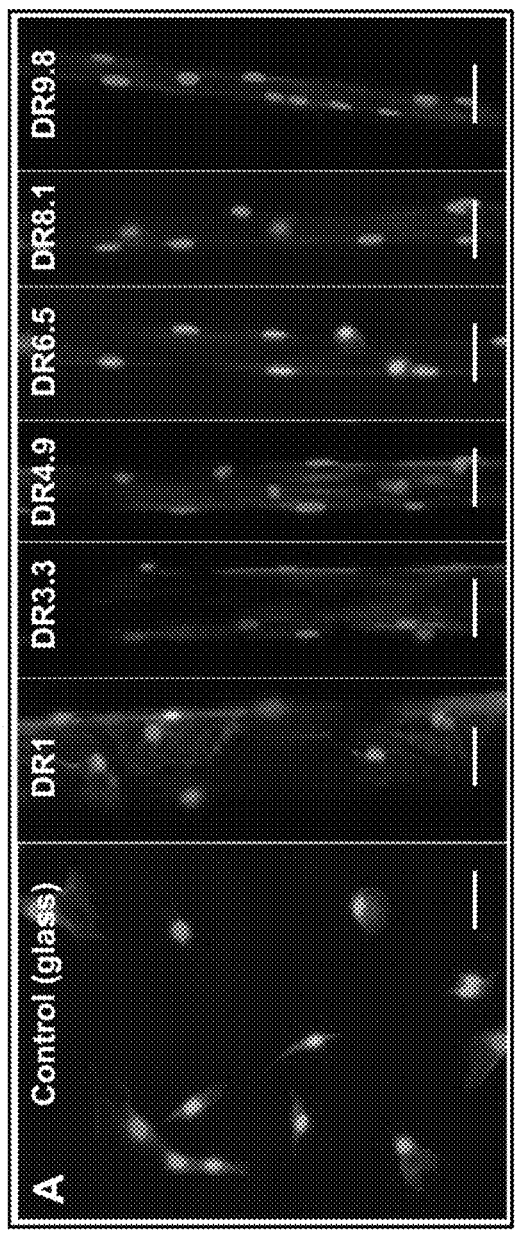
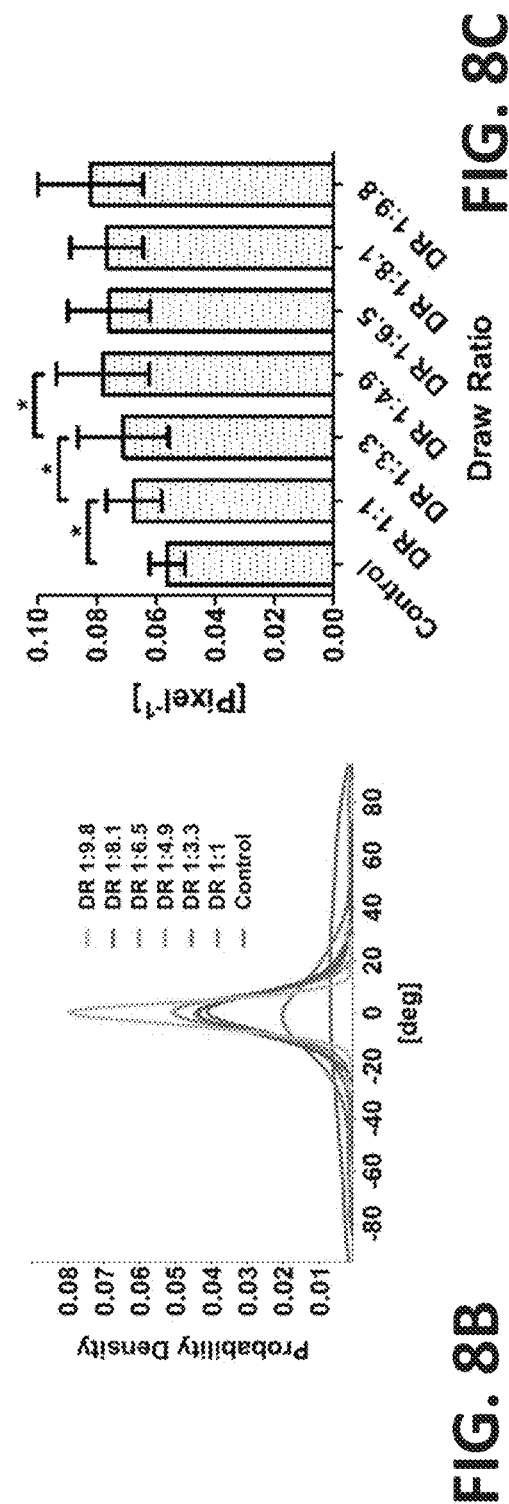
FIG. 8A
FIG. 8B
FIG. 8C

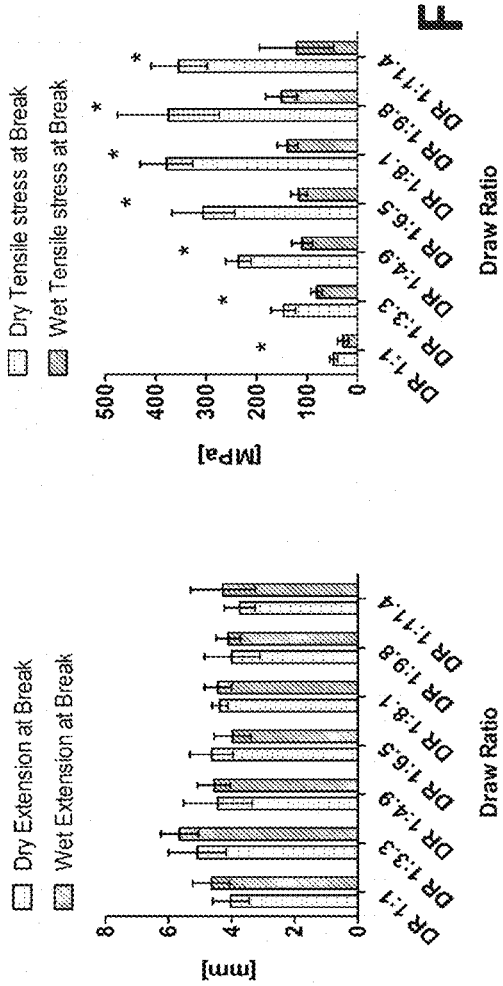
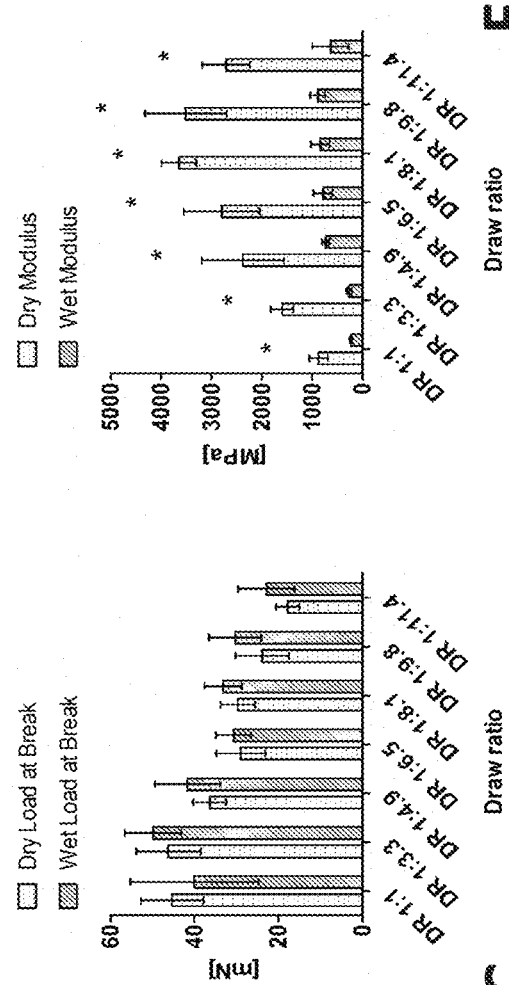
FIG. 12A  FIG. 12B  FIG. 12C  FIG. 12D

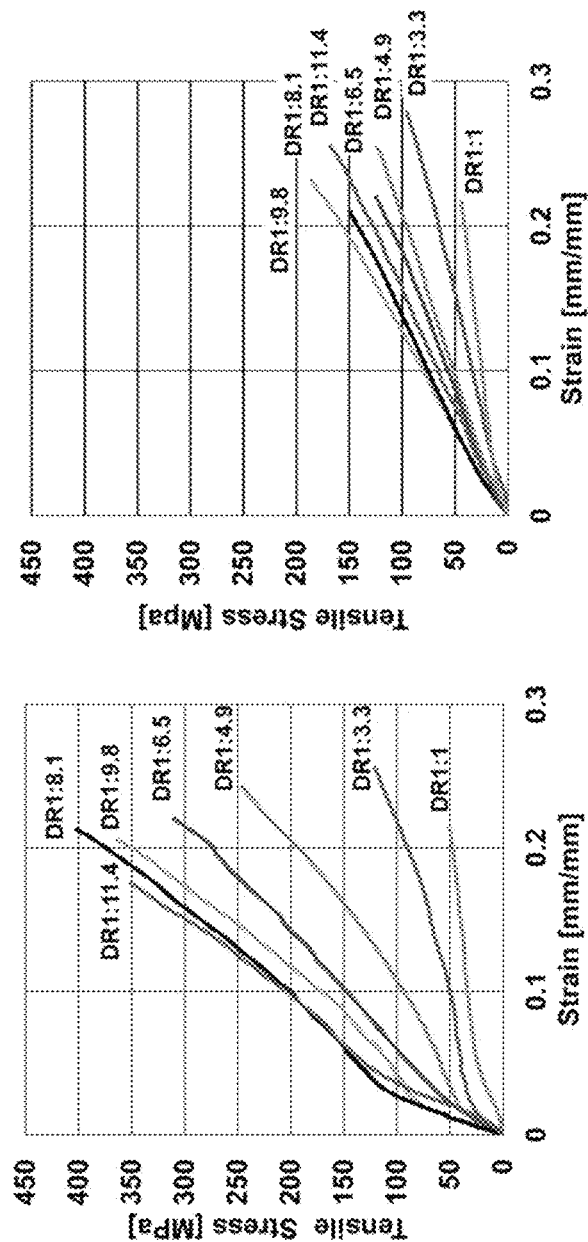

METHOD OF GENERATING COLLAGEN FIBERS

RELATED APPLICATIONS

This application claims the benefit of priority under 35 USC § 119(e) of U.S. Provisional Patent Application No. 62/445,333 filed on Jan. 12, 2017, the contents of which are incorporated herein by reference in their entirety.

SEQUENCE LISTING STATEMENT

The ASCII file, entitled 72286SequenceListing.txt, created on Jan. 11, 2018, comprising 110,640 bytes, submitted concurrently with the filing of this application is incorporated herein by reference.

FIELD AND BACKGROUND OF THE INVENTION

The present invention, in some embodiments thereof, relates to a method of generating collagen fibers.

Collagen is the principal structural protein in the body and constitutes approximately one-third of the total body protein. It comprises most of the organic matter of the skin, tendons, bones and teeth and occurs as fibrous inclusions in most other body structures. Some of the properties of collagen are its high tensile strength; its ion exchanging ability, due in part to the binding of electrolytes, metabolites and drugs; its low antigenicity, due to masking of potential antigenic determinants by the helical structure, and its low extensibility, semipermeability, and solubility. Furthermore collagen is a natural substance for cell adhesion. These properties make this protein suitable for fabrication of bioremodelable research products and medical devices such as implantable prostheses, cell growth substrates, and cellular and acellular tissue constructs.

Naturally, collagen is secreted by cells as a long triple-helical monomer, which polymerizes spontaneously into fibrils and strands, which often have a preferential orientation essential to the function of tissues such as skin, bone and nerve.

The exact structure of the collagen fibril is still unknown, but increasingly detailed models are becoming available, emphasizing the relation between fibril structure and function. Current models hint at a semi-crystalline (liquid crystal like) structure, combining a highly ordered arrangement in the axial direction and a short-range liquid-like order in the lateral direction.

Collagen in its monomeric form is soluble in cold acidic pH (~pH 2) solutions, and can be precipitated in the form of fibrils by neutralizing the pH, increasing the temperature and/or the ionic strength. Fibrillogenesis is entropy driven—the loss of water molecules from monomer surfaces drives the collagen monomers out of solution and into assemblies with a circular cross-section, so as to minimize surface area.

The fibrils formed in-vitro display D-banding pattern of 67 nm wide cross striations typical of natural collagen fibrils formed in-vivo, but lack altogether the macroscopic order that is the basis of structural tissues. Fibrils precipitated out of bulk solutions form an entangled mesh reminiscent of spaghetti and not the neatly ordered arrays of fibrils observed in nature.

Collagen can be deposited from solution by a variety of processes including casting, lyophilization, electrospinning and other processes well known to one skilled in the art. In most of these procedures, collagen fibers of widely varying diameters and lengths from the micrometer range typical of conventional fibers down to the nanometer range are formed. Owing to their small diameters, electrospun fibers possess very high surface-to-area ratios and are expected to display morphologies and material properties very different from their conventional counterparts occurring in nature.

Numerous attempts to direct or align collagen fibrils for manufacturing of collagen matrices have been performed, employing various methods. Major efforts are aimed at creating 2D (collagen surface) or 3D (collagen scaffold) matrices. Exemplary methods include: alignment by surface templating, chemical patterning, nanolithography, electrochemical fabrication, use of a magnetic field, and by shear flow.

In vitro, collagen displays mesophase (liquid crystalline) properties at concentrations above ~20 mg/ml (depending on acid concentration of the solvent). At concentrations between ~20 to 50 mg/ml diffuse nematic phases appear in the bulk isotropic solution, observed as birefringent flakes. When the collagen concentration is increased, precholesteric patterns form—observed as spherulites, bands, or zigzag extinction patterns. Further increase in the concentration leads to formation of cholesteric patterns that become more and more compact until the entire sample displays characteristic fingerprint pattern.

At concentrations above 150 mg/ml, collagen fibrillar aggregates start to appear even in acidic solution, displaying the 67 nm banding typical of collagen fibrils, in a process reminiscent of a cholesteric-to-smectic (N*/SmA) transition.

U.S. Pat. No. 7,057,023 teaches spinning of liquid crystalline silk to generate silk fibers.

U.S. Patent Application No. 20070187862 teaches spinning a solution of liquid crystalline silk, wherein the solution is devoid of organic solvents to generate silk fibers.

U.S. Patent Application No. 20090069893 teaches formation of oriented collagen based materials from mesophase collagen by application of a shear force.

WO2011/064773 teaches generation of fibers from a solution of mesophase collagen.

Yaari et al., TISSUE ENGINEERING: Part A, Volume 19, Numbers 13 and 14, 2013, pages 1502-1505 teaches generation of fibers from a solution of mesophase collagen.

Additional background art includes Yaari et al., ACS Biomaterials Sci. Eng. Pages 349-360, Feb. 15, 2016.

SUMMARY OF THE INVENTION

According to an aspect of some embodiments of the present invention there is provided a method of generating a collagen fiber, the method comprising:

(a) extruding a solution of collagen into a coagulating solution to generate the collagen fiber; and (b) drawing the fiber in the coagulating solution, wherein the rate of the drawing of the fiber is higher than the rate of extruding the solution of collagen into the coagulating solution.

According to an aspect of some embodiments of the present invention there is provided a collagen fiber produced by the method described herein.

According to an aspect of some embodiments of the present invention there is provided a method of regenerating tissue comprising providing to a subject in need-thereof the collagen fiber described herein, thereby regenerating tissue.

According to an aspect of some embodiments of the present invention there is provided a method of generating tissue comprising culturing cells on the scaffold described herein under conditions that the cells generate a tissue, thereby generating the tissue.

According to an aspect of some embodiments of the present invention there is provided a pharmaceutical composition comprising the isolated collagen fiber described herein.

According to an aspect of some embodiments of the present invention there is provided a cosmetic composition comprising the isolated collagen fiber described herein.

According to an aspect of some embodiments of the present invention there is provided a scaffold comprising the collagen fibers described herein.

According to some embodiments of the invention, the method further comprises isolating the collagen fiber following the extruding.

According to some embodiments of the invention, the method further comprises drying the collagen fiber following the isolating.

According to some embodiments of the invention, the extruding is effected concomitantly with the drawing.

According to some embodiments of the invention, the method further comprises polymerizing the collagen following the extruding.

According to some embodiments of the invention, the method further comprises crosslinking the collagen following the extruding.

According to some embodiments of the invention, the crosslinking is effected in the coagulating solution.

According to some embodiments of the invention, the extruding is effected using a spinneret.

According to some embodiments of the invention, the rate of the drawing of the fiber is at least three times higher than the rate of extruding the solution of collagen into the coagulating solution.

According to some embodiments of the invention, the extruding is effected by passing the collagen solution through an orifice comprising an inner diameter between 10 μm-100 μm.

According to some embodiments of the invention, the collagen comprises recombinant atelocollagen.

According to some embodiments of the invention, the collagen is human collagen.

According to some embodiments of the invention, the collagen is present at a concentration between 20-200 mg/ml in the solution.

According to some embodiments of the invention, the collagen is present at a concentration between 30-70 mg/ml in the solution.

According to some embodiments of the invention, the extruding is effected by passing through an orifice comprising an inner diameter of about 30 μm.

According to some embodiments of the invention, the solution of collagen is an acidic solution.

According to some embodiments of the invention, the collagen fiber has a diameter of about 10 μm.

According to some embodiments of the invention, the collagen fiber has a tensile stress at break of between 60-200 MPa when wet.

According to some embodiments of the invention, the collagen fiber has a Young's modulus of between 500-1200 MPa when wet.

According to some embodiments of the invention, the collagen fiber has a strain at break of between 0.15-0.3 when wet.

According to some embodiments of the invention, the scaffold further comprises a cell population seeded thereon.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-C. Wet spinning and drawing system. A—Setting of the wet spinning and drawing system and fiber formation process. i—A syringe fitted in a microinjection system injects the rhcollagen dope through a small bore ceramic spinneret into a coagulation bath. A speed-controlled rotating spool collects the fiber at the desired take-up speed. The ratio between the injection and take-up velocities determines the draw ratio (DR). ii—The fiber, wound on the spool, is crosslinked and washed, iii—dehydrated in ethanol, and iv—dried by a critical point drying process in $CO_2$, to yield v—dried finished fibers. B—An image of a GTA-crosslinked dehydrated fiber sample. C—A plot of fiber diameter (grey) and the length (in meters) per mg rhcollagen vs draw ratio.

FIGS. 2A-G. Scanning electron microscopy (SEM) images of fibers drawn at different draw ratios. A to G—DR1:1, DR1:3.3, DR1:4.9, DR1:6.5, DR1:8.1, DR1:9.8, DR1:11.4, respectively. Note the differences in scale between the various images.

FIGS. 3A-E. SEM of fractured fiber ends. A and B—DR 1:1, B is a magnification of the area marked by the broken white line in A. The black arrow denotes the fiber's outer shell. B—The black wavy line at the bottom right marks crimp pattern of the fibrils. C and D—DR1:4.9. A core-shell structure is still visible. The black arrow shows separation of the shell into constituent sub-fibrils. D is a magnification of the area marked by the broken white line in C, showing higher alignment and tighter packing of the core fibrils. E—DR 1:11.3. Arrows denote areas were the fiber separates into the component sub fibrils.

FIGS. 4A-G. Polarized microscopy of wet spun collagen fibers (20× magnification). Color (see scheme on right) indicates azimuthal orientation of the slow optical axis (molecular axis), and intensity indicates degree of retardance (nm). Insets at the top depict the retardance intensity along the white broken line that transverses the fibers' perpendicular to their axis. Note that the insets are not to scale with the fiber images, but expanded to ease viewing.

Fibers spun at the different draw ratios from A to G—DR 1:1, DR 1:3.3, DR 1:4.9, DR 1:6.5, DR 1:8.1, DR 1:9.8, DR 1:11.4 respectively.

FIGS. 5A-D. A comparison of ultimate tensile strength (UTS), Young's modulus, tensile strain at break and energy at break between fibers drawn under different draw ratios. Five samples were tested for every draw ratio. A—Tensile stress at break. B—Young's modulus. C—Tensile strain at break. D—Energy at break. The combined effects of the tensile strain and the UTS graphs is observed. Error bars shows the SD. Asterisk denotes statistical significance of $p<0.05$.

Figure 6:
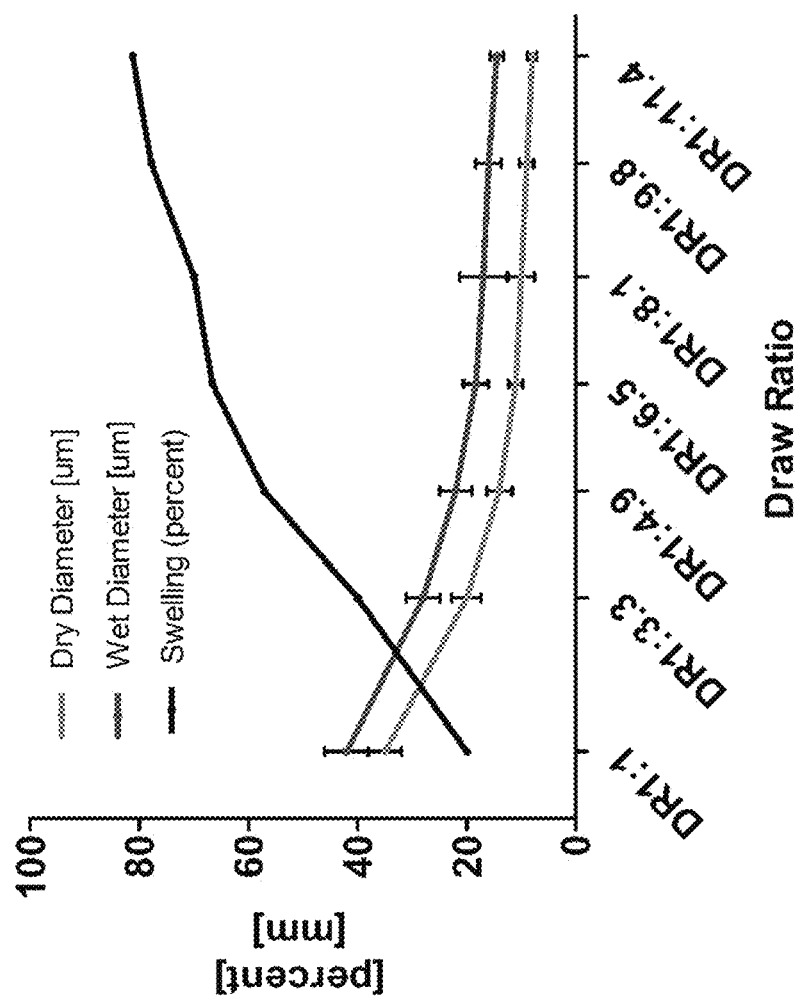

FIG. 6. Effect of draw ratio on fiber diameter and swelling. Dry fiber diameter (grey), wet fiber diameter (blue) and the swelling ratio (black) are plotted against draw ratio. Error bars show the SD.

FIGS. 7A-D. Comparison of the mechanical properties of EDC-versus GTA-crosslinked spun rhcollagen fibers. Fibers were drawn at DR 1:8.1. A—Swelling. The swelling percent for each indicated pair is presented in parentheses. B—Stress at break. C—Extension at break. D—Load at break. Error bars in all graphs denote SD. Asterisk denotes statistical significance of $p<0.01$.

FIGS. 8A-C. Rat tenocytes alignment on the drawn rhcollagen fibers. A—Fluorescence microscope images of tenocytes grown on rhcollagen fibers. The DAPI-stained nuclei appear blue, and Pahlloidin-stained actin fibers appear red. The leftmost image shows tenocytes grown on glass slide as control. Next to it, from left to right, are images of cells grown on fibers with increasing draw ratios. Scale bar—50 µm. B—Nuclear orientation probability density diagram. The nuclear orientation is defined as the angle between the x-axis and the major axis of the nucleus. The fiber axis was set parallel to the x-axis (0 degrees). C—Nucleus length to area ratio (in pixels). The number of cells assessed from every experimental group was: n=206, 216, 161, 150, 153, 178 and 117, for the control, DR 1:1, DR 1:3.3, DR 1:4.9, DR 1:6.5, DR 1:8.1 and DR 1:9.8, respectively. Error bars show the SD. Asterisk denotes statistical significance of $p<0.05$.

Figure 9:
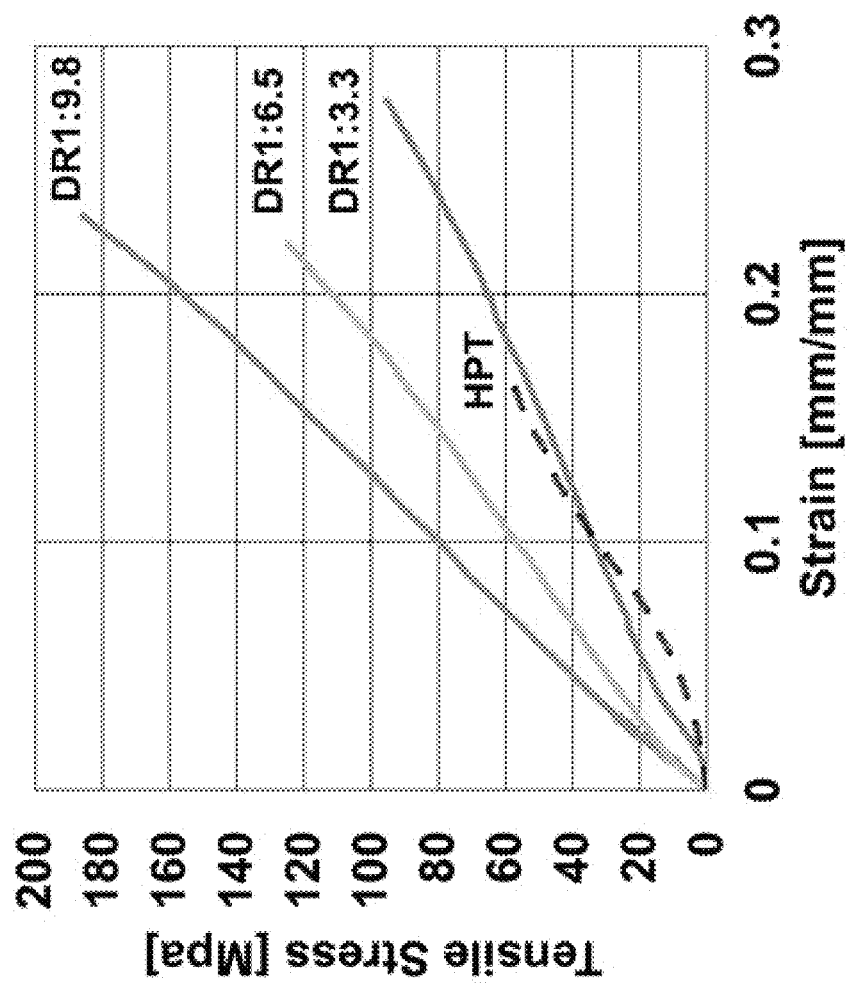

FIG. 9. A comparison of stress/strain plots from representative hydrated fibers versus a hydrated human patellar tendon (HPT)[35a]. Fiber DRs are noted on the plot.

Figure 10:
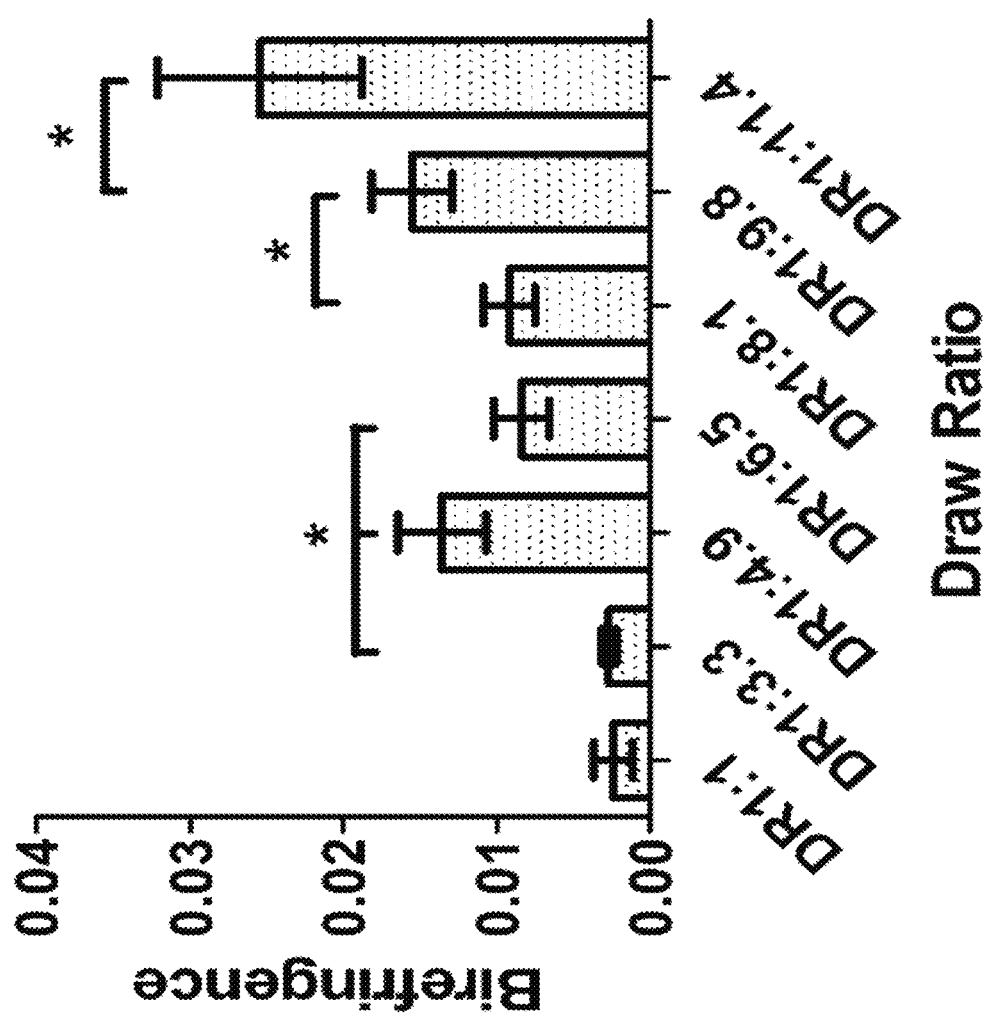

FIG. 10. A plot of the birefringence versus draw ratio. The birefringence was calculated by dividing the retardance by the fiber diameter. Error bars shows the standard deviation (SD). n=5, 6, 6, 6, 7, 6, 5, for DR1 to 11.4, respectively. Asterisk denotes statistical significance of $p<0.05$. For birefringence calculation, the diameter (D) of the fiber and retardance value (R) were measured at the same point along the fiber. Birefringence for every fiber sample was then calculated as the average R/D of 5-7 individual measurements, as previously described[28].

Figure 11A:
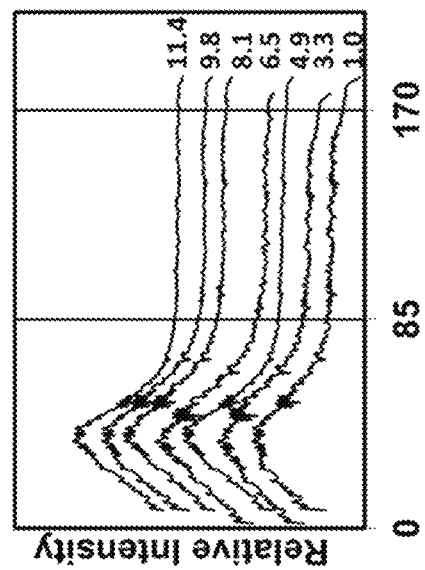
Figure 11B:
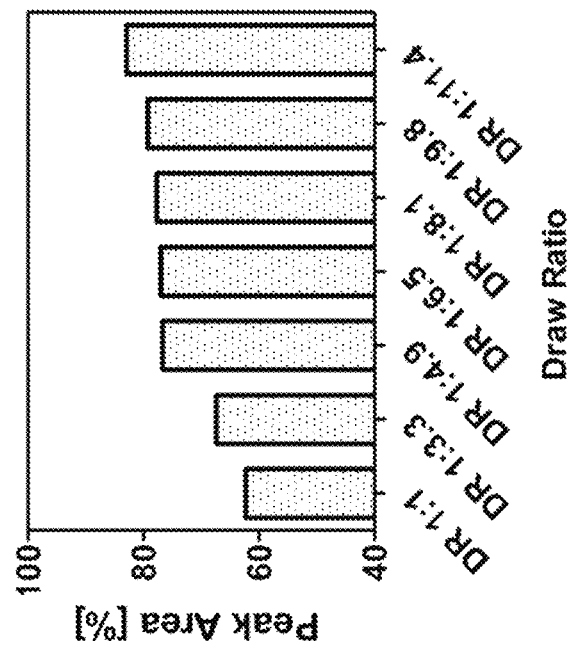

FIGS. 11A-B. Small angle X-ray scattering analysis. A—Azimuthal integrations of the diffraction profiles obtained from fibers drawn under different DR conditions. B—Ratio of the area under the peak (from 0° to 85°) to the total area of the signal (from 0° to 180°). It can be seen that the ordered area relative to the total signal area gradually increased with the draw ratio, reflecting the increased order of the collagen monomers in the fiber.

FIGS. 12A-D. A comparison of mechanical properties between dry and wet rhcollagen fibers. A—Extension at break. B—Stress at break. C—Load at break. D—Young's modulus. Error bars show the SD. Asterisk denotes statistical significance of $p<0.05$.

FIGS. 13A-B. Representative stress strain plots of fibers spun at different draw ratios. A—Dry fibers, B—hydrated fibers.

Figure 14:
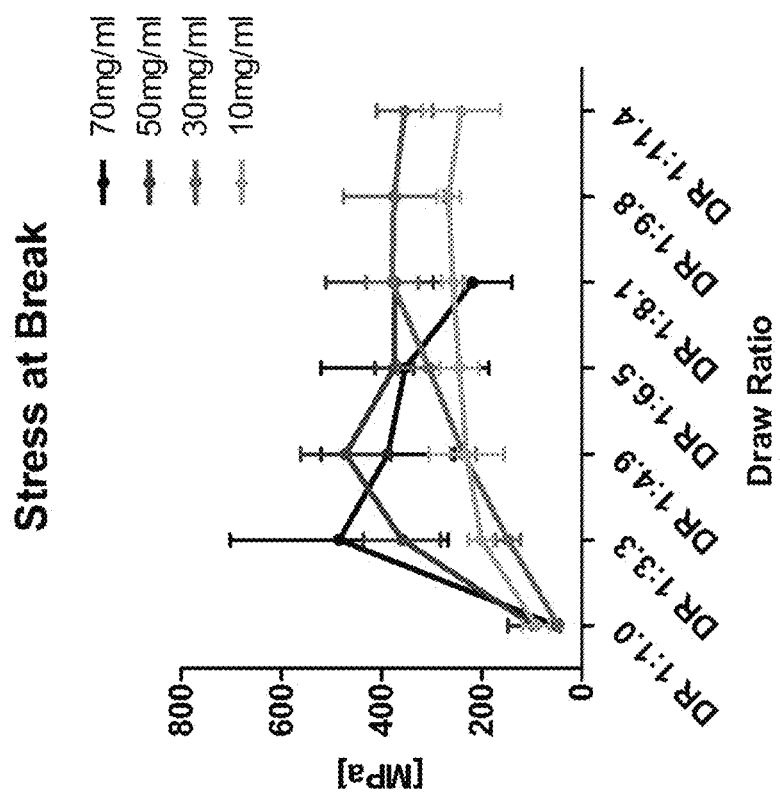

FIG. 14. Effect of dope concentration and drawing on ultimate tensile stress. The black, blue, green, and grey lines correspond to dope rhcollagen concentrations of 70, 50, 30 and 10 mg/mL, respectively. It can be seen that increasing the dope concentration increases the fibers' peak UTS values, and that these values are obtained at a lower draw ratio. Error bars in all graphs denote SD. Only the 10 mg/mL peak UTS values are significantly different than the other values.

DESCRIPTION OF SPECIFIC EMBODIMENTS OF THE INVENTION

The present invention, in some embodiments thereof, relates to a method for generating collagen fibers.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Order and alignment lie at the basis of the molecular structure of high-modulus, high tenacity fibers. The fiber-forming monomers can be roughly divided into two main groups—stiff, interactive molecules and flexible, inert molecules. Each group of polymers is spun using different methods that rely on different principals; rigid molecules form a liquid crystalline dope that is aligned by shear forces applied as it passes through the narrow spinneret, while flexible, inert molecules are spun by methods that rely on extensive drawing to create order.

The present inventors have now attempted to combine both shear alignment and drawing to order and orient collagen molecules.

Yaari, A et al., Tissue Engineering Part A 2013, 19 (13-14), 1502-1506 teaches the formation of highly aligned and ordered fibers by wet spinning of liquid crystalline rhcollagen dope (at a concentration of 180 mg/mL), without drawing. The shear forces acting on the dope were sufficient to align the monomers in the injection direction, and the order was then preserved upon coagulation. However, working with such concentrated, high viscosity solutions can be very challenging, especially if the goal is to obtain thin fibers (<10 µm). Injection of such dopes through small diameter spinnerets requires high pressures, and is accompanied by frequent clogging.

The present inventors therefore decreased the dope concentration to 30 mg/mL, which lowered the viscosity and enabled continuous spinning. This concentration is substantially higher than the concentration reported in most soluble collagen fiber spinning works (1-10 mg/mL), and offers two advantages: first, the formed fiber is solid and strong enough to support its own weight immediately upon exit from the spinneret, allowing high speed spin-drawing without the need for prolonged incubations or cumbersome collection devices. This further allowed efficient decoupling of the spinning operation from downstream stages, such as washing and crosslinking, which can be performed directly on the spool. A flexible, modular spinning process is obtained, that can be adjusted for different crosslinking methods, or accommodate additional buffer incubations (i.e., for fibrillogenesis), when required. The second advantage of concentrated dope spinning is improved fibrillar order and alignment. It has been shown that the degree of orientation induced in isotropic, high aspect ratio mesogen solutions by shear forces is dependent on concentration. Concentrated solutions show increased alignment and orientation compared to dilute solutions under similar shear, and may even become nematic under certain conditions.

Although spin-drawing is a critical element in both natural spinning mechanisms and modern fiber spinning technologies, and has been used for silk protein and even gelatin fiber spinning methodologies, spin drawing of native, soluble collagen fibers has not been previously reported. Post-spin drawing of collagen fibers (i.e., stretching of the previously spun, solid fibers) has been reported, and shown to improve alignment and mechanical performance. It is, however, significantly different from spin-drawing, where the liquid dope is drawn directly out of the spinneret, and stretched several fold while concomitantly undergoing a sol-gel transition that is induced by drying and neutralization. During this process, the collagen molecules are in a semi-dissolved state—they are free enough to slide past each other, but stronger interactions gradually develop between them as the pH nears the pI, and water is removed. These intermolecular interactions pull the molecules from both ends in the direction of fiber axis, aligning and packing them tightly together, until they are solidified in the form of fibrils. In addition to the high levels of density and alignment achieved by spin drawing, it also allows for high spinning rates, and the formation of thin fibers. In the present examples, spinning rates of up to 1,000 m/hr and fiber diameters as thin as 8 µm were generated (see Tables 1A-B of the Examples section herein below).

As observed in the SEM images (FIGS. 2A-G and FIGS. 3A-E) and corroborated by the polarized microscopy images (FIGS. 4A-G), undrawn and low draw ratio fibers display a double layered, core-shell fiber structure. Its formation begins as soon as the liquid dope exits the spinneret in to the coagulation bath, where it begins to coagulate and harden on its outer side. A solid and denser external layer is thus formed, acting as a barrier that slows coagulation of the inner material. If drawing is exerted, the take-up forces are borne by this solid layer that is consequently stretched and aligned. The outcome is an aligned, dense outer shell that encompasses a less ordered, less oriented and less compact core. As draw ratio increase, the shell becomes more aligned and oriented, and also takes up more of the fiber cross-section area, until a uniform structure is formed, composed only of a uniform, tightly packed and aligned material.

The retardance (FIGS. 4A-G) and birefringence (FIG. 10) of the fibers show an overall increase in the fiber molecular order with increasing draw ratio. Interestingly, a strong local peak was observed for DR1:4.9, indicating increased molecular order for that draw ratio. The mechanical properties of the fibers presented in this work significantly surpassed those previously reported. A comparison of the hydrated fibers mechanical properties to literature data of reconstituted collagen fibers (Table 2) indicated an improvement of more than 25% for strain and 30% for UTS.

A comparison between the stress/strain plots of representative hydrated fibers and a hydrated human patellar tendon is presented in FIG. 9. Human patellar and Achilles tendons were measured to have a UTS of 81.3 MPa and 60 MPa, strain at break of 0.21 and 0.18, and modulus of 550 MPa and 513 MPa, respectively[35]. The DR 1:9.8, GTA cross-linked fibers displayed a UTS of 150 MPa, strain at break of 0.21 and Young's modulus of 890 MPa. The drawn fibers therefore compared to natural human tendon in their stress at break, but had almost twice the UTS, giving them a substantially higher toughness.

The mechanical properties of the fibers were greatly affected by the draw ratio. Both the UTS and the modulus significantly increased with the introduction of drawing and continued rising along a steep slope with each increment in the draw ratio (FIGS. 5A and 5B). For the dry fibers, peak values of 378 MPa and 3.5 GPa for the UTS and modulus, respectively, were measured at DR 1:8.1, beyond which, further drawing did not improve the UTS or modulus.

Comparison of the GTA-versus the EDC-crosslinked fibers showed that when dry, EDC-crosslinked fibers had the same extension and only a slightly reduced load at break as the GTA-crosslinked fibers. However, hydration had a significant impact, with EDC-crosslinked fibers swelling substantially more and displaying notably reduced strength, breaking at 40 MPa relative versus 138 MPa for fibers crosslinked with GTA.

Rat tenocyte alignment on spun rhcollagen fibers demonstrated that the degree of molecular and fibrillar alignment in the fiber shell influences cell shape and directionality, as reflected by the nuclear shape and orientation. Interestingly, cellular alignment and orientation were affected by draw ratio, as predicted by the SAX (FIGS. 11A-B) and birefringence (FIG. 10) measurements, with a strong increase from DR 1:1 to 1:4.9 fibers, followed by a plateau or even a decrease until DR 1:8.1, followed by another strong increase to 9.8.

Thus, according to one aspect of the present invention there is provided a method of generating a collagen fiber, the method comprising:

(a) extruding a solution of collagen into a coagulating solution to generate the collagen fiber; and (b) drawing the fiber in the coagulating solution, wherein the rate of the drawing of said fiber is higher than the rate of extruding said solution of collagen into said coagulating solution.

The term "collagen" as used herein, refers to a polypeptide having a triple helix structure and containing a repeating Gly-X-Y triplet, where X and Y can be any amino acid but are frequently the imino acids proline and hydroxyproline. According to one embodiment, the collagen is a type I, II, III, V, XI, or biologically active fragments therefrom.

A collagen of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to collagen sequences listed in Table 1 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

According to a particular embodiment, the collagen is a human collagen.

In another embodiment, the collagen comprises a naturally occurring amino acid sequence of human collagen.

Table 1A below lists examples of collagen NCBI sequence numbers.

TABLE 1A

| Exemplary procollagen NCBI sequence number | SEQ ID NO: |
|---|---|
| P02452 | 1 |
| P08123 | 2 |

The annotation of SEQ ID NO: 1 is as follows:
Amino acids 1-22—signal peptide;
Amino acids 23-161—N-terminal peptide;
Amino acids 162-1218—collagen alpha-1(I) chain;
Amino acids 1219-1464—C-terminal peptide;
The annotation of SEQ ID NO: 2 is as follows:
Amino acids 1-22—signal peptide;
Amino acids 23-79—N-terminal peptide;
Amino acids 80-1119—collagen alpha-2(I) chain;
Amino acids 1120-1366—C-terminal peptide;

According to one embodiment, the collagen of the present invention comprises a sufficient portion of its telopeptides such that under suitable conditions it is capable of forming fibrils.

Thus, for example, the collagen may be atelocollagen, a telocollagen or procollagen.

As used herein, the term "atelocollagen" refers to collagen molecules lacking both the N- and C-terminal propeptides typically comprised in procollagen and at least a portion of its telopeptides, but including a sufficient portion of its telopeptides such that under suitable conditions it is capable of forming fibrils.

The term "procollagen" as used herein, refers to a collagen molecule (e.g. human) that comprises either an N-terminal propeptide, a C-terminal propeptide or both. Exemplary human procollagen amino acid sequences are set forth by SEQ ID NOs: 3, 4, 5 and 6.

The term "telocollagen" as used herein, refers to collagen molecules that lack both the N- and C-terminal propeptides typically comprised in procollagen but still contain the telopeptides. The telopeptides of fibrillar collagen are the remnants of the N- and C-terminal propeptides following digestion with native N/C proteinases.

According to another embodiment, the collagen is devoid of its telopeptides and is not capable of undergoing fibrillogenesis.

According to another embodiment, the collagen is a mixture of the types of collagen above.

The collagen may be isolated from an animal (e.g. bovine, pig or human) or may be genetically engineered using recombinant DNA technology (e.g. human collagen).

Methods of isolating collagen from animals are known in the art. Dispersal and solubilization of native animal collagen can be achieved using various proteolytic enzymes (such as porcine mucosal pepsin, bromelain, chymopapain, chymotrypsin, collagenase, ficin, papain, peptidase, proteinase A, proteinase K, trypsin, microbial proteases, and, similar enzymes or combinations of such enzymes) which disrupt the intermolecular bonds and remove the immunogenic non-helical telopeptides without affecting the basic, rigid triple-helical structure which imparts the desired characteristics of collagen (see U.S. Pat. Nos. 3,934,852; 3,121,049; 3,131,130; 3,314,861; 3,530,037; 3,949,073; 4,233,360 and 4,488,911 for general methods for preparing purified soluble collagen). The resulting soluble collagen can be subsequently purified by repeated precipitation at low pH and high ionic strength, followed by washing and re-solublization at low pH.

Plants expressing collagen chains and procollagen are known in the art, see for example, WO06035442A3; Merle et al., FEBS Lett. 2002 Mar. 27; 515(1-3):114-8. PMID: 11943205; and Ruggiero et al., 2000, FEBS Lett. 2000 Mar. 3; 469(1):132-6. PMID: 10708770; and U.S. Pat. Applications 2002/098578 and 2002/0142391 as well as U.S. Pat. No. 6,617,431 each of which are incorporated herein by reference.

It will be appreciated that the present invention also contemplates genetically modified forms of collagen/atelocollagen—for example collagenase-resistant collagens and the like [Wu et al., Proc Natl. Acad Sci, Vol. 87, p. 5888-5892, 1990].

Recombinant procollagen or telocollagen (e.g. human) may be expressed in any non-animal cell, including but not limited to plant cells and other eukaryotic cells such as yeast and fungus.

Plants in which procollagen or telocollagen may be produced (i.e. expressed) may be of lower (e.g. moss and algae) or higher (vascular) plant species, including tissues or isolated cells and extracts thereof (e.g. cell suspensions). Preferred plants are those which are capable of accumulating large amounts of collagen chains, collagen and/or the processing enzymes described herein below. Such plants may also be selected according to their resistance to stress conditions and the ease at which expressed components or assembled collagen can be extracted. Examples of plants in which human procollagen may be expressed include, but are not limited to tobacco, maize, alfalfa, rice, potato, soybean, tomato, wheat, barley, canola, carrot, lettuce and cotton.

Production of recombinant procollagen is typically effected by stable or transient transformation with an exogenous polynucleotide sequence encoding human procollagen.

Exemplary polynucleotide sequences encoding human procollagen are set forth by SEQ ID NOs: 7, 8, 9 and 10.

Production of human telocollagen is typically effected by stable or transient transformation with an exogenous polynucleotide sequence encoding human procollagen and at least one exogenous polynucleotide sequence encoding the relevant protease. Alternatively, a protease may be added following isolation of the recombinant procollagen.

The stability of the triple-helical structure of collagen requires the hydroxylation of prolines by the enzyme prolyl-4-hydroxylase (P4H) to form residues of hydroxyproline within the collagen chain. Although plants are capable of synthesizing hydroxyproline-containing proteins, the prolyl hydroxylase that is responsible for synthesis of hydroxyproline in plant cells exhibits relatively loose substrate sequence specificity as compared with mammalian P4H. Thus, production of collagen containing hydroxyproline only in the Y position of Gly-X-Y triplets requires co-expression of collagen and human or mammalian P4H genes [Olsen et al, Adv Drug Deliv Rev. 2003 Nov. 28; 55(12):1547-67].

Thus, according to one embodiment, the procollagen or telocollagen is expressed in a subcellular compartment of a plant that is devoid of endogenous P4H activity.

As used herein, the phrase "subcellular compartment devoid of endogenous P4H activity" refers to any compartmentalized region of the cell which does not include plant P4H or an enzyme having plant-like P4H activity. According to one embodiment, the subcellular compartment is a vacuole, an apoplast or a chloroplast. According to a particular embodiment, the subcellular compartment is a vacuole.

Accumulation of the expressed procollagen in a subcellular compartment devoid of endogenous P4H activity can be effected via any one of several approaches.

For example, the expressed procollagen/telocollagen can include a signal sequence for targeting the expressed protein to a subcellular compartment such as the apoplast or an organelle (e.g. chloroplast).

Examples of suitable signal sequences include the chloroplast transit peptide (included in Swiss-Prot entry P07689, amino acids 1-57) and the Mitochondrion transit peptide (included in Swiss-Prot entry P46643, amino acids 1-28).

Targeting to the vacuole may be achieved by fusing the polynucleotide sequence encoding the collagen to a vacuolar targeting sequence—for example using the vacuolar targeting sequence of the thiol protease aleurain precursor (NCBI accession P05167 GI:113603)-MAHARVLLLALAV-LATAAVAVASSSSFADSNPIRPVTDRAASTLA (SEQ ID NO: 14). Typically, the polynucleotide sequence encoding the collagen also comprises an ER targeting sequence. In one embodiment, the ER targeting sequence is native to the collagen sequence. In another embodiment, the native ER targeting sequence is removed and a non-native ER targeting sequence is added. The non-native ER targeting sequence may be comprised in the vacuolar targeting sequence. It will be appreciated, for it to traverse the ER and move on to the vacuole, the collagen sequence should be devoid of an ER retention sequence.

Alternatively, the sequence of the procollagen can be modified in a way which alters the cellular localization of the procollagen when expressed in plants.

The present invention contemplates genetically modified cells co-expressing both human procollagen and a P4H. In one embodiment, the P4H is capable of correctly hydroxylating the procollagen alpha chain(s) [i.e. hydroxylating only the proline (Y) position of the Gly-X-Y triplets]. P4H is an enzyme composed of two subunits, alpha and beta as set forth in Genbank Nos. P07237 and P13674. Both subunits are necessary to form an active enzyme, while the beta subunit also possesses a chaperon function.

The P4H expressed by the genetically modified cells of the present invention is preferably a human P4H. An exemplary polynucleotide sequence which encodes human P4H is SEQ ID Nos: 11 and 12. In addition, P4H mutants which exhibit enhanced substrate specificity, or P4H homologues can also be used. A suitable P4H homologue is exemplified by an *Arabidopsis* oxidoreductase identified by NCBI accession no: NP_179363.

Since it is essential that P4H co-accumulates with the expressed procollagen chain, the coding sequence thereof is preferably modified accordingly (e.g. by addition or deletion of signal sequences). Thus, the present invention contemplates using P4H polynucleotide sequences that are fused to vacuole targeting sequences. It will be appreciated that for targeting to the vacuole, when an endogenous ER retention sequence is present, it should be removed prior to expression.

In mammalian cells, collagen is also modified by Lysyl hydroxylase, galactosyltransferase and glucosyltransferase. These enzymes sequentially modify lysyl residues in specific positions to hydroxylysyl, galactosylhydroxylysyl and glucosylgalactosyl hydroxylysyl residues at specific positions. A single human enzyme, Lysyl hydroxylase 3 (LH3), as set forth in Genbank No. 060568, can catalyze all three consecutive modifying steps as seen in hydroxylysine-linked carbohydrate formation.

Thus, the genetically modified cells of the present invention may also express mammalian LH3 (optionally fused to vacuole targeting sequences). It will be appreciated that for targeting to the vacuole, the endogenous ER retention sequence is removed prior to expression.
An LH3 encoding sequence such as that set forth by SEQ ID NO: 13, can be used for such purposes.

The procollagen(s) and modifying enzymes described above can be expressed from a stably integrated or a transiently expressed nucleic acid construct which includes polynucleotide sequences encoding the procollagen alpha chains and/or modifying enzymes (e.g. P4H and LH3) positioned under the transcriptional control of functional promoters. Such a nucleic acid construct (which is also termed herein as an expression construct) can be configured for expression throughout the whole organism (e.g. plant, defined tissues or defined cells), and/or at defined developmental stages of the organism. Such a construct may also include selection markers (e.g. antibiotic resistance), enhancer elements and an origin of replication for bacterial replication.

There are various methods for introducing nucleic acid constructs into both monocotyledonous and dicotyledenous plants (Potrykus, I., Annu. Rev. Plant. Physiol., Plant. Mol. Biol. (1991) 42:205-225; Shimamoto et al., Nature (1989) 338:274-276). Such methods rely on either stable integration of the nucleic acid construct or a portion thereof into the genome of the plant, or on transient expression of the nucleic acid construct, in which case these sequences are not inherited by the plant's progeny.

In addition, several methods exist in which a nucleic acid construct can be directly introduced into the DNA of a DNA-containing organelle such as a chloroplast.

There are two principle methods of effecting stable genomic integration of exogenous sequences, such as those included within the nucleic acid constructs of the present invention, into plant genomes:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues.

Regardless of the transformation technique employed, once collagen-expressing progeny are identified, such plants are further cultivated under conditions which maximize expression thereof. Progeny resulting from transformed plants can be selected, by verifying presence of exogenous mRNA and/or polypeptides by using nucleic acid or protein probes (e.g. antibodies). The latter approach enables localization of the expressed polypeptide components (by for example, probing fractionated plants extracts) and thus also verifies the plant's potential for correct processing and assembly of the foreign protein.

Following cultivation of such plants, the telopeptide-comprising collagen is typically harvested. Plant tissues/cells are preferably harvested at maturity, and the procollagen molecules are isolated using extraction approaches. Preferably, the harvesting is effected such that the procollagen remains in a state that it can be cleaved by protease enzymes. According to one embodiment, a crude extract is generated from the transgenic plants of the present invention and subsequently contacted with the protease enzymes.

As mentioned, the propeptide or telopeptide-comprising collagen may be incubated with a protease to generate atelocollagen or collagen prior to solubilization. It will be appreciated that the propeptide or telopeptide-comprising collagen may be purified from the genetically engineered cells prior to incubation with protease, or alternatively may be purified following incubation with the protease. Still alternatively, the propeptide or telopeptide-comprising collagen may be partially purified prior to protease treatment and then fully purified following protease treatment. Yet alternatively, the propeptide or telopeptide-comprising collagen may be treated with protease concomitant with other extraction/purification procedures.

Exemplary methods of purifying or semi-purifying the telopeptide-comprising collagen of the present invention include, but are not limited to salting out with ammonium sulfate or the like and/or removal of small molecules by ultrafiltration.

According to one embodiment, the protease used for cleaving the recombinant propeptide or telopeptide comprising collagen is not derived from an animal. Exemplary proteases include, but are not limited to certain plant derived proteases e.g. ficin (EC 3.4.22.3) and certain bacterial derived proteases e.g. subtilisin (EC 3.4.21.62), neutrase. The present inventors also contemplate the use of recombinant enzymes such as rhTrypsin and rhPepsin. Several such enzymes are commercially available e.g. Ficin from Fig tree latex (Sigma, catalog #F4125 and Europe Biochem), Subtilisin from *Bacillus licheniformis* (Sigma, catalog #P5459) Neutrase from bacterium *Bacillus amyloliquefaciens* (Novozymes, catalog # PW201041) and TrypZean™, a recombinant human trypsin expressed in corn (Sigma catalog #T3449).

As used herein, the phrase "collagen fiber" refers to a non-soluble self-aggregate of collagen comprising a fibrous structure in which collagen molecules are packed in series and also in parallel. It will be appreciated that the collagen molecules may be in their monomeric form or their polymeric form. The collagen fibers generated according to the method of the present invention typically have a cross sectional diameter in the range of about 10-20 μm.

As mentioned, the starting material for generating the fibers of the present invention is a solution of collagen (e.g. recombinant human atetocollagen or recombinant human procollagen).

According to one embodiment, the liquid collagen solution is an acidic solution of collagen monomers (e.g. human or bovine collagen type I). Exemplary acids for solubilizing monomeric collagen include, but are not limited to hydrochloric acid (HCl) and acetic acid.

As used herein, the phrase "collagen monomers" refers to monomeric collagen that has not undergone the process of polymerization.

According to one embodiment a concentration of about 1 mM-100 mM HCl is used to solubilize the collagen monomers. An exemplary concentration of HCl which may be used to solubilize collagen monomers is about 10 mM HCl.

According to one embodiment a concentration of about 0.05 mM-50 mM acetic acid is used to solubilize the collagen monomers. An exemplary concentration of acetic acid which may be used to solubilize collagen monomers is about 0.5 M acetic acid.

The starting concentration of the collagen (e.g. atelocollagen) in the solution is typically about 1 mg/ml-5 mg/ml, for example 3 mg/ml.

The starting collagen solution is then typically concentrated to form the dope. The liquid collagen solution may be concentrated using any means known in the art, including but not limited to filtration, rotary evaporation and dialysis membrane.

Dialysis may be effected against a hygroscopic polymer, for example, PEG, a polyethylene oxide, amylose or sericin. Preferably, the PEG is of a molecular weight of 10,000-50,000 g/mol (e.g. 35,000 g/mol) and has a concentration of 10-50%—e.g. 10%. Typically, the dialysis is effected in the cold (e.g. at about 4° C.). The dialysis is effected for a time period sufficient to result in a final concentration of aqueous collagen solution of about 10 mg/ml or more. According to one embodiment, the collagen is concentrated such that it reaches a final concentration between 20-200 mg/ml, 20-150 mg/ml, 20-100 mg/ml, 30-100 mg/ml, 30-90 mg/ml, 30-80 mg/ml, 30-70 mg/ml, 30-60 mg/ml or 30-50 mg/ml.

In one embodiment, the collagen is concentrated to a degree such that it changes to be in a liquid crystalline state.

Liquid crystal is a state of matter that is intermediate between the crystalline solid and the amorphous liquid. There are three basic phases of liquid crystals, known as smectic phase, nematic phase, and cholesteric phase and the present invention envisages the use of any of the above. In the smectic phase a one-dimensional translational order, as well as orientational order exists. In the nematic phase, only a long-range orientational order of the molecular axes exists. Cholesteric phase is also a nematic liquid type with molecular aggregates lie parallel to one another in each plane, but each plane is rotated by a constant angle from the next plane.

In most cases, dialysis for 2-16 hours is sufficient, depending on volume and concentration.

In another embodiment, the doping collagen solution may be prepared by ultrasonic treatment. Brown E. M. et al. Journal of American Leather Chemists Association, 101: 274-283 (2006), herein incorporated by reference by its entirety.

The present invention contemplates addition of a cross-linker to the acidic solution of collagen monomers. The acidity of the solution prevents premature crosslinking. Following extrusion into a neutral coagulating solution, the crosslinker becomes activated and crosslinks the collagen fibrils. Examples of crosslinkers are further described herein below.

It will be appreciated that once the collagen is solubilized in the acid, the pH of the solution may be increased. Raising of the pH may be effected by dialyzing the acidic collagen against a higher pH buffer (e.g. pH 4/4.5 acetate buffer).

The collagen doping solution may comprise additives such as ATP to decrease the threshold of the required concentration to develop the liquid crystal state. Without being bound by any particular theory, generally, highly negative charged molecules (more than −3) can be used as additives to the collagen solution to promote the orientation or adhesion of the collagen. Suitable additives include, but are not limited to ATP, vanadate, insulin, phosphate and VGF.

Other additives that may be added to the doping solution of the present invention include antimicrobials such as silver nitrate, iodized radicals (e.g., Triosyn®; Hydro Biotech), benzylalkonium chloride, alkylpyridinium bromide (cetrimide), and alkyltrimethylammonium bromide. Viscosity enhancers may be added to improve the rheological properties of the starting material. Examples include, but are not limited to polyacrylates, alginate, cellulosics, guar, starches and derivatives of these polymers, including hydrophobically modified derivatives.

The present invention further contemplates addition of hyaluronic acid (HA) to the doping solution to generate a highly extensible and spinable dope.

As mentioned, the collagen fibers of the present invention are generated by extruding the solution of liquid crystalline collagen into a coagulating solution.

As used herein, the term "extruding" as used herein refers to the forcing of a flowable material out through a relatively narrow aperture (i.e. a nozzle in the widest sense), e.g. through a needle.

According to one embodiment the aperture has an inner diameter of between 10 μm-100 μm. According to one embodiment the aperture has an inner diameter of about 30 μm. For this aperture size, preferably a doping solution of about 30-70 mg/ml of collagen (e.g. human recombinant atelocollagen) is used.

According to another embodiment, the extruding is effected using a spinneret. The spinneret can have a single orifice or multiple orifices, depending on, for example, the volume of collagen solution to be spun, and the number of collagen fibers to be produced. Spinnerets may be composed of various materials, including metals and alloys, such as stainless steel or tantalum, polymeric materials, such as PEEK tubing, ceramics or carbon-composite materials. Spinnerets with a single orifice may be made of metal, preferably stainless steel. Spinnerets with multiple orifices are preferably made of polymeric tubing, most preferably PEEK tubing. Spinnerets may also be treated with substances, such as TEFLON™ or spray silicon, in such a manner as to prevent adherence of the dope to the spinneret needle.

The coagulating solution serves to stabilize or preserve the molecular orientation of the extruded collagen molecules. Typically, the stabilizing agent in the coagulating solution is at a high enough osmolarity such that is can extract water from the collagen and dry it. The collagen typically remains in the coagulating solution for at least 15 minutes, at least 1 hour, at least 6 hours, at least 12 hours—for example about 24 hours.

In one embodiment, the coagulating solution may be a concentrated aqueous salt solution having a high ionic strength. The high osmotic pressure of a concentrated salt solution draws the water away from the collagen protein, thereby facilitating fiber coagulation. Preferred coagulating solutions include aqueous solutions containing a high concentration of aluminum sulfate, ammonium sulfate, sodium sulfate, or magnesium sulfate. Additives, particularly acids, such as acetic acid, sulfuric acid, or phosphoric acid, or also sodium hydroxide may be added to the salt-based coagulation bath.

Contemplated salt coagulating solutions may comprise one or more salts of high solubility such as, for example, salts containing one or more of the following anions: nitrates, acetates, chlorates, halides (fluoride, chloride, bromide, iodide), sulfates, sulfides, sulfites, carbonates, phosphates, hydroxides, thiocyanates, bicarbonates, formates, propionates, and citrates; and one or more of the following cations: ammonium, aluminum, calcium, cesium, potassium, lithium, magnesium, manganese, sodium, nickel, rubidium, antimony, and zinc.

The solution may also contain an acid of the same anion as the salt, e.g., nitric, acetic, hydrochloric, sulfuric, carbonic, phosphoric, formic, propionic, citric, or lactic acid, or another acid which also forms highly soluble salts with the cation(s) present. Preferably, the salts used in the coagulating solution of the present invention are multivalent anions and/or cations, resulting in a greater number of ions, and proportionally higher ionic strength, on dissociation. Typically, concentrated salt coagulating solutions comprise about 30%-70% (w/v) of salt; preferably about 40-65%.

In another embodiment, the coagulating solution comprises an organic solvent. The present invention contemplates coagulating solutions wherein at least 50% thereof comprises the organic solvent. The present invention further contemplates coagulating solutions wherein at least 70% thereof comprises the organic solvent. The present invention further contemplates coagulating solutions wherein at least 90% thereof comprises the organic solvent.

Exemplary organic solvents that may be used according to this aspect of the present invention include, but are not limited to acetone, methanol, isopropanol, methylated spirit and ethanol.

The coagulation solution of this aspect of the present invention may allow polymerization (i.e. fibrilogenesis) of collagen monomers. Such a solution typically is at a neutral or high pH (e.g. pH 7.4 or more) to allow for polymerization. An exemplary fibrilogenesis buffer comprises between about 5 mM sodium phosphate to about 50 mM sodium phosphate.

Useful additives may be included in the coagulating medium include, but are not limited to surfactants, osmoprotective agents, stabilizing agents, UV inhibitors, and antimicrobial agents. Stabilizers that protect against UV radiation, radical formation, and biodegradation include, for example, 2-hydroxybenzophenones, 2-hydroxyphenyl-2-(2H)-benzotriazoles, cifmamates, and mixtures thereof. These chemicals are capable of absorbing and dissipating UV energy, thereby inhibiting UV degradation. Free radicals are neutralized by hindered amine light stabilizers (HALS), butylated hydroxyanisole (BHA), and butylated hydroxytoluene (BHT).

The growing fiber can be extruded through an air gap before entering the coagulation medium, or the fiber can be extruded directly into the coagulation medium.

Concomitantly with the extrusion into the coagulating solution of the present invention, the fibers are stretched or drawn under conditions wherein significant molecular orientation is imparted. The variables include but are not limited to draw ratio, temperature and strain rate. Preferably, the drawing is effected in the coagulation medium.

Drawing may be effected using a rotating spool or a set of godets, with the filament wrapped several times (e.g. 3-8 times) around the chromium roller of each godet.

The present inventors have found that when the rate of the drawing of the fiber is higher than the rate of extruding the solution of collagen into the coagulating solution, the fibers have enhanced properties, as detailed herein below.

Exemplary draw ratios (contemplated by the present inventors include about 1:3 (e.g. 1:3.3), 1:5 (e.g. 1:4.9), 1:6.5, 1:8 (e.g. 1:8.1), 1:10 (e.g. 1:9.8) and 1:11.5 (e.g. 1:11.4), wherein the ratio is rate of extruding: rate of drawing.

Preferably, the fibers remains in the coagulating solution for at least two hours, 6 hours, 12 hours, 24 hours or longer following the drawing (and prior to the optional crosslinking, as further described herein below).

The drawn collagen fibers may optionally be crosslinked using any one of the below methods: 1. by glutaraldehyde and other chemical crosslinking agents; 2. by glycation using different sugars; 3. by Fenton reaction using metal ions such as copper; 4. by lysine oxidase; or 5. by UV radiation.

In one embodiment, the crosslinker is added to the coagulation medium following the drawing (e.g. 6-48 hours, e.g. about 24 hours) following the drawing. The drawn collagen fibers may be contacted with the crosslinker for any length of time that allows sufficient crosslinking (e.g. 6-48 hours, e.g. about 24 hours).

buffer bath, raising the temperature of the water or buffer bath, and observing the temperature of the water or buffer bath at which the fiber shrinks. In order to observe shrinkage, a tension may be applied on the fiber.

According to one embodiment, the fibers generated according to the method of the present invention have a tensile stress at break of between 60-200 MPa or 60-150 MPa when wet.

The fibers generated according to the method of the present invention may have a Young's modulus of between 500-1200 MPa or 500-1000 MPa when wet.

Furthermore, the fibers generated according to the method of the present invention may have a strain at break of between 0.15-0.3 or 0.15-0.25 when wet.

Table 1B, herein below summarize the mechanical properties of the dry and wet fibers.

TABLE 1B

| Draw Ratio | Dry Load at Break [mN] | Wet load at Break [mN] | Dry UTS [MPa] | Wet UTS [MPa] | Dry Young's Modulus [GPa] | Wet Young's Modulus [GPa] | Dry strain at break | Wet Strain at Break |
|---|---|---|---|---|---|---|---|---|
| 1:1 | 45.3 ± 7.5 | 40.0 ± 15.3 | 47.1 ± 7.8 | 28.9 ± 11.0 | 0.87 ± 0.18 | 0.23 ± 0.02 | 0.20 ± 0.03 | 0.23 ± 0.05 |
| 1:3.3 | 46.1 ± 7.7 | 49.8 ± 6.7 | 146.9 ± 24.4 | 80.9 ± 10.9 | 1.59 ± 0.22 | 0.27 ± 0.05 | 0.25 ± 0.05 | 0.28 ± 0.05 |
| 1:4.9 | 36.4 ± 3.9 | 41.7 ± 7.8 | 236.4 ± 25.4 | 109.6 ± 20.6 | 2.38 ± 0.82 | 0.73 ± 0.07 | 0.22 ± 0.05 | 0.23 ± 0.03 |
| 1:6.5 | 29.0 ± 5.9 | 30.7 ± 4.2 | 305.6 ± 61.8 | 116.3 ± 15.7 | 2.39 ± 0.75 | 0.79 ± 0.19 | 0.23 ± 0.03 | 0.20 ± 0.03 |
| 1:8.1 | 29.7 ± 4.1 | 33.2 ± 4.4 | 378.7 ± 52.2 | 138.6 ± 20.5 | 3.64 ± 0.35 | 0.84 ± 0.18 | 0.22 ± 0.01 | 0.22 ± 0.02 |
| 1:9.8 | 23.9 ± 6.4 | 30.3 ± 6.3 | 375.2 ± 100.7 | 150.9 ± 31.1 | 3.51 ± 0.81 | 0.89 ± 0.15 | 0.20 ± 0.04 | 0.21 ± 0.02 |
| 1:11.4 | 17.8 ± 2.8 | 22.9 ± 6.8 | 354.2 ± 55.8 | 121.1 ± 73.6 | 2.71 ± 0.47 | 0.63 ± 0.36 | 0.19 ± 0.02 | 0.19 ± 0.01 |

The fibers may be optionally washed in one or more wash baths following the drawing stage. In addition, following the drawing stage, the fibers may be dried or dehydrated to evaporate the coagulating solution. Alternatively, the fibers may be washed in baths of successively lower concentration of the coagulant used, e.g., successively lower salt or organic solvent concentrations subsequent to the coagulant bath, until an ultimate water bath is used.

Following generation and optional crosslinking/polymerization, the physical properties of the collagen fibers may be tested.

To measure such physical properties, any suitable apparatus having (1) two clamps for attaching to the fiber(s), (2) a force transducer attached to one of the clamps for measuring the force applied to the fiber, (3) a means for applying the force, and (4) a means for measuring the distance between the clamps, is suitable. For example, tensiometers can be purchased from manufacturers MTS, Instron, and Cole Parmer. To calculate the tensile strength, the force at failure is divided by the cross-sectional area of the fiber through which the force is applied, resulting in a value that can be expressed in force (e.g., Newtons) per area. The stiffness is the slope of the linear portion of the stress/strain curve. Strain is the real-time change in length during the test divided by the initial length of the specimen before the test begins. The strain at failure is the final length of the specimen when it fails minus the initial specimen length, divided by the initial length.

An additional physical property that is associated with the extent of cross-linking in a composition is the shrinkage temperature. In general, the higher the temperature at which a collagenous composition begins to shrink, the higher the level of cross-linking. The shrinkage temperature of a fiber can be determined by immersing the fiber in a water or Techniques for directing or casting the collagen fibers generated according to the methods of the present invention for manufacturing of aligned collagen matrices into 2D or 3D structures are widely known and include for example alignment by surface templating [David A. Cisneros, Jens Friedrichs, Anna Taubenberger, Clemens M. Franz, and Daniel J. Muller. Creating Ultrathin Nanoscopic Collagen Matrices For Biological And Biotechnological Applications small 2007, 3, No. 6, 956-963]; by chemical patterning [Frederic A. Denis, Antoine Pallandre, Bernard Nysten, Alain M. Jonas, and Christine C. Dupont-Gillain. Alignment and Assembly of Adsorbed Collagen Molecules Induced by Anisotropic Chemical Nanopatterns. small 2005, 1, No. 10, 984-991]; nanolithography [Donna L. Wilson, Raquel Martin, Seunghun Hong, Mark Cronin-Golomb, Chad A. Mirkin, and David L. Kaplan. Surface organization and nanopatterning of collagen by dip-pen nanolithography. Proc Natl Acad Sci USA. 2001 Nov. 20; 98(24):13660-4]; electrochemical fabrication [Xingguo Cheng, Umut A. Gurkan, Christopher J. Dehen, Michael P. Tate, Hugh W. Hillhouse, Garth J. Simpson, Ozan Akkus An electrochemical fabrication process for the assembly of anisotropically oriented collagen bundles. Biomaterials 29 (2008) 3278-3288]; magnetic field [Jim Torbet, Marilyne Malbouyres, Nicolas Builles, Virginie Justin, Muriel Roulet, Odile Damour, Ake Oldberg, Florence Ruggiero, David J. S. Hulmes. Orthogonal scaffold of magnetically aligned collagen lamellae for corneal stroma reconstruction. Biomaterials 28 (2007) 4268-4276]; and by shear flow [Babette Lanfer, Uwe Freudenberg, Ralf Zimmermann, Dimitar Stamov, Vincent Korber, Carsten Werner. Aligned fibrillar collagen matrices obtained by shear flow deposition. Biomaterials 29 (2008) 3888-3895].

The collagen fibers generated according to the method of the present invention may be used per se, or as part of a composite material. The components of the composites of the present invention may be attached to, coated on, embedded or impregnated into the collagen of the present invention. In such composites, the collagen may be uncrosslinked, partially crosslinked or fully crosslinked. Exemplary components of the composite material include, but are not limited to minerals, pharmaceutical agents (i.e. drugs) polysaccharides and polypeptides.

Exemplary polysaccharides that may be used in composite materials of the present invention include, but are not limited to glycosaminoglycans such as chondroitin sulfate of type A, C, D, or E, dermatan sulfate, keratan sulfate, heparan sulfate, heparin, hyaluronic acid and their derivatives, individually or mixed.

Exemplary polypeptides that may be used in composite materials of the present invention include, but are not limited to resilin, silk, elastin and fibronectin.

Exemplary minerals that may be used in composite materials of the present invention include, but are not limited to calcium, magnesium, boron, zinc, copper, manganese, iron, silicon, selenium, phosphorus and sulfur. Methods for preparing collagen mineral composites are well known in the art, see for example WO/2006/118803.

The collagen fibers generated according to the method of the present invention show superior mechanical properties compared to those that have not been generated according to the methods described herein.

Since the collagen of the present invention has been shown to be highly structured and comprise high strength, the collagen may be particularly suitable for bioprostheses suitable for tendon and/or ligament repair, augmentation, and/or replacement. A biomaterial with increased strength over that of natural tissue (muscle and the like) can allow for a bioprosthesis that has a smaller cross-sectional area than that of the natural tissue being replaced or repaired. The smaller area can improve the function of the bioprosthesis as a scaffold for neo-tendon or ligament in-growth, which may augment strength and/or long term survival rate of the repair. The use of high-strength fibers on medical devices and constructs may also offset or reduce the effects of stress concentration factors that reside at regions of integration in adjacent tissue such as bone.

The collagen generated according to the method of the present invention or composites thereof may therefore also be used as part of a scaffold.

As used herein, the term "scaffold" refers to a 3D matrix upon which cells may be cultured (i.e., survive and preferably proliferate for a predetermined time period).

The scaffold may be fully comprised of the collagen of the present invention or composites thereof, or may comprise a solid support on which is layered the collagen of the present invention.

A "solid support," as used refers to a three-dimensional matrix or a planar surface (e.g. a cell culture plate) on which cells may be cultured. The solid support can be derived from naturally occurring substances (i.e., protein based) or synthetic substances. Suitable synthetic matrices are described in, e.g., U.S. Pat. Nos. 5,041,138, 5,512,474, and 6,425,222. For example, biodegradable artificial polymers, such as polyglycolic acid, polyorthoester, or polyanhydride can be used for the solid support. Calcium carbonate, aragonite, and porous ceramics (e.g., dense hydroxyapatite ceramic) are also suitable for use in the solid support. Polymers such as polypropylene, polyethylene glycol, and polystyrene can also be used in the solid support.

Therapeutic compounds or agents that modify cellular activity can also be incorporated (e.g. attached to, coated on, embedded or impregnated) into the scaffold material or a portion thereof. In addition, agents that act to increase cell attachment, cell spreading, cell proliferation, cell differentiation and/or cell migration in the scaffold may also be incorporated into the scaffold. Such agents can be biological agents such as an amino acid, peptides, polypeptides, proteins, DNA, RNA, lipids and/or proteoglycans.

Suitable proteins which can be used along with the present invention include, but are not limited to, extracellular matrix proteins [e.g., fibrinogen, collagen, fibronectin, vimentin, microtubule-associated protein 1D, Neurite outgrowth factor (NOF), bacterial cellulose (BC), laminin and gelatin], cell adhesion proteins [e.g., integrin, proteoglycan, glycosaminoglycan, laminin, intercellular adhesion molecule (ICAM) 1, N-CAM, cadherin, tenascin, gicerin, RGD peptide and nerve injury induced protein 2 (ninjurin2)], growth factors [epidermal growth factor, transforming growth factor-α, fibroblast growth factor-acidic, bone morphogenic protein, fibroblast growth factor-basic, erythropoietin, thrombopoietin, hepatocyte growth factor, insulin-like growth factor-I, insulin-like growth factor-II, Interferon-β, platelet-derived growth factor, Vascular Endothelial Growth Factor and angiopeptin], cytokines [e.g., M-CSF, IL-1beta, IL-8, beta-thromboglobulin, EMAP-II, G-CSF and IL-10], proteases [pepsin, low specificity chymotrypsin, high specificity chymotrypsin, trypsin, carboxypeptidases, aminopeptidases, proline-endopeptidase, *Staphylococcus aureus* V8 protease, Proteinase K (PK), aspartic protease, serine proteases, metalloproteases, ADAMTS17, tryptase-gamma, and matriptase-2] and protease substrates.

Additionally and/or alternatively, the scaffolds of the present invention may comprise an antiproliferative agent (e.g., rapamycin, paclitaxel, tranilast, Atorvastatin and trapidil), an immunosuppressant drug (e.g., sirolimus, tacrolimus and Cyclosporine) and/or a non-thrombogenic or anti-adhesive substance (e.g., tissue plasminogen activator, reteplase, TNK-tPA, glycoprotein IIb/IIIa inhibitors, clopidogrel, aspirin, heparin and low molecular weight heparins such as enoxiparin and dalteparin).

Cells which may be seeded on the collagen of the present invention may comprise a heterogeneous population of cells or alternatively the cells may comprise a homogeneous population of cells. Such cells can be for example, stem cells (such as embryonic stem cells, bone marrow stem cells, cord blood cells, mesenchymal stem cells, adult tissue stem cells), progenitor cells, or differentiated cells such as chondrocytes, osteoblasts, connective tissue cells (e.g., fibrocytes, fibroblasts and adipose cells), endothelial and epithelial cells. The cells may be naïve or genetically modified.

According to one embodiment of this aspect of the present invention, the cells are mammalian in origin.

Furthermore, the cells may be of autologous origin or non-autologous origin, such as postpartum-derived cells (as described in U.S. application Ser. Nos. 10/887,012 and 10/887,446). Typically the cells are selected according to the tissue being generated.

Techniques for seeding cells onto or into a scaffold are well known in the art, and include, without being limited to, static seeding, filtration seeding and centrifugation seeding.

It will be appreciated that to support cell growth, the cells are seeded on the collagen of the present invention in the presence of a culture medium.

The culture medium used by the present invention can be any liquid medium which allows at least cell survival. Such a culture medium can include, for example, salts, sugars, amino acids and minerals in the appropriate concentrations and with various additives and those of skills in the art are capable of determining a suitable culture medium to specific cell types. Non-limiting examples of such culture medium include, phosphate buffered saline, DMEM, MEM, RPMI 1640, McCoy's 5A medium, medium 199 and IMDM (available e.g., from Biological Industries, Beth Ha'emek, Israel; Gibco-Invitrogen Corporation products, Grand Island, N.Y., USA).

The culture medium may be supplemented with various antibiotics (e.g., Penicillin and Streptomycin), growth factors or hormones, specific amino acids (e.g., L-glutamin) cytokines and the like.

The scaffolds of the present invention may be administered to subjects in need thereof for the regeneration of tissue such as connective tissue, muscle tissue such as cardiac tissue and pancreatic tissue. Examples of connective tissues include, but are not limited to, cartilage (including, elastic, hyaline, and fibrocartilage), collagen, adipose tissue, reticular connective tissue, embryonic connective tissues (including mesenchymal connective tissue and mucous connective tissue), tendons, ligaments, and bone.

The collagen fibers generated according to the method of the present invention may be used to prepare films and matrices. According to one embodiment, biomedical devices may be formed from such films and matrices.—e.g. collagen membranes for hemodialysis.

According to one embodiment, the collagen films and membranes are kept cold, in the dark in the dark or hydrated in order to prevent the collapsing and condensation of the structure.

According to another embodiment, the collagen generated according to the method of the present invention (or films derived therefrom) is used in cell cultures. Collagen as a film or as a coating on other materials has also been used in tissue culture for the growth of fastidious cells. The protein surface and the orientation of the fibers appear to promote cell growth in vitro and probably in vivo as well.

The phrase "cell culture" or "culture" as used herein refers to the maintenance of cells in an artificial, e.g., an in vitro environment. It is to be understood, however, that the term "cell culture" is a generic term and may be used to encompass the cultivation not only of individual prokaryotic (e.g., bacterial) or eukaryotic (e.g., animal, plant and fungal) cells, but also of tissues, organs, organ systems or whole organisms.

Generally, cell culture is carried out by growing cells in a culture vessel in the presence of cell culture medium. By "culture vessel" herein is meant a glass, plastic, or metal container and the like that can provide an aseptic environment for culturing cells. Culture vessels include but are not limited to petri dishes and 96-well plates.

In some embodiments, the collagen generated according to the method of the present invention is used to coat the surface of a cell culture vessel.

In some embodiments, the collagen generated according to the method of the present invention is used in a wound healing process. During the wound healing process, oriented collagen acts to modulate cell proliferation and migration and is important in the wound contraction process. Cuttle L., et al., Wound Repair and Regeneration, 13:198-204 (2005).

In some embodiments, collagen films provided herein are used to prevent adhesions following tendon injuries, to lengthen levator palpebrae muscles ophthalmic surgery, and to repair transected nerves. Collagen films provided herein may further be used for burn dressings and wound healing. In some embodiments, the collagen is preferably not heavily cross-linked. If the films are heavily cross-linked, they do not become incorporated into the tissue, but rather, granulation, and re-epithelialization take place beneath the films. Here the film acts as an inert dressing. Collagen felt or sponge, on the other hand, may function as a true artificial skin. Healing of bone defects and wounds also appears enhanced by collagen.

It will be appreciated that the collagen of the present invention comprises a myriad of uses other than for tissue regeneration including, but not limited to treatment of diseases such as interstitial cystitis, scleroderma, and rheumatoid arthritis cosmetic surgery, as a healing aid for burn patients, as a wound-healing agent, as a dermal filler, for spinal fusion procedures, for urethral bulking, in duraplasty procedures, for reconstruction of bone and a wide variety of dental, orthopedic and surgical purposes.

The collagen of the present invention may be formulated as pharmaceutical and/or cosmetic compositions.

The term "cosmetic composition" as used herein refers to a composition formulated for external application to human or animal skin, nails, or hair for the purpose of beautifying, coloring, conditioning, or protecting the body surface. The present cosmetic composition can be in any form including for example: a gel, cream, lotion, makeup, colored cosmetic formulations, shampoo, hair conditioner, cleanser, toner, aftershave, fragrance, nail enamel, and nail treatment product.

The phrase "colored cosmetic formulation" refers to cosmetics containing pigment including for example eye shadow, lipsticks and glosses, lip and eye pencils, mascara, and blush.

For example, the collagen fibers of the present invention may also be used as a cosmetic agent for treatment of skin and hair.

Thus, the present invention contemplates the collagen of the present invention as a substance which can be topically applied, optionally in combination with other active substance such as for example a vitamin (vitamin A, C, E or their mixtures) or other topically active substances including but not limited to avarol, avarone or plant extracts, such as Extr. *Cepae* or Extr. *Echinaceae pallidae*. The collagen of the present invention may be formulated as a topical agent in the form of creams, ointments, lotions or gels such as a hydrogels e.g. on the basis of polyacrylate or an oleogel e.g. made of water and Eucerin.

Oleogels comprising both an aqueous and a fatty phase are based particularly on *Eucerinum anhydricum*, a basis of wool wax alcohols and paraffin, wherein the percentage of water and the basis can vary. Furthermore additional lipophilic components for influencing the consistency can be added, e.g. glycerin, polyethylene glycols of different chain length, e.g. PEG400, plant oils such as almond oil, liquid paraffin, neutral oil and the like. The hydrogels of the present invention can be produced through the use of gel-forming agents and water, wherein the first are selected especially from natural products such as cellulose derivatives, such as cellulose ester and ether, e.g. hydroxyethyl-hydroxypropyl derivatives, e.g. tylose, or also from synthetic products such as polyacrylic acid derivatives, such as Carbopol or Carbomer, e.g. P934, P940, P941. They can be produced or polymerized based on known regulations, from alcoholic suspensions by adding bases for gel formation.

Exemplary amounts of collagen in the gel include 0.01-30 g per 100 g of gel, 0.01-10 g per 100 g of gel, 0.01-8 g per 100 g of gel, 0.1-5 g per 100 g of gel.

The cosmetic composition may comprise other agents capable of conditioning the body surface including, for example humectants; emollients; oils including for example mineral oil; and shine enhancers including for example dimethicone and cyclomethicone. The present conditioning agents may be included in any of the present pharmacological and/or cosmetic compositions.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the collagen accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran.

Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (collagen) effective to prevent, alleviate or ameliorate symptoms of a disorder (e.g., skin disease).

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide tissue levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

MATERIALS AND METHODS

Collagen Source:
Recombinant human atelocollagen ("Collagen", 3 mg/mL in 10 mM HCl).
Reagents:
Except where otherwise noted, all reagents were purchased from Sigma Aldrich Ltd. (Rehovot, Israel).
Collagen Dope:
The collagen solution was concentrated to a concentration of 30 mg/mL by dialysis in a dialysis bag (molecular weight cutoff of 3.5 kDa, "SnakeSkin" Thermo Fisher Scientific) against 10% polyethylene glycol, (molecular weight 35 kDa) in 10 mM HCl, (pH 2). Before spinning, the dope was centrifuged at 4,000 RCF for 5 minutes to remove gas bubbles.
Fiber Wet Spinning:
The wet spinning and drawing apparatus (FIG. 1-A(i)) was comprised of an injection system, a coagulation bath and speed-controlled collecting mandrel (spool). The acidic rhcollagen dope was placed in a plastic syringe to which a ceramic die was fitted. In order to produce fibers comparable in diameter to cotton or textile polymer fibers (10-15 µm), a modified ceramic capillary (Kulicke & Soffa, 48FFA-4146-R31) was used, with an internal 10° conical taper and 30 µm orifice diameter. Usage of smaller diameter dies resulted in frequent clogging and necessitated high injection pressures, and was therefore avoided.
The syringe was placed in a Chemyx "Nanojet" microinjection system, with volume, time, and injection rate controls. The dope coagulated immediately upon exposure to the coagulant and formed a soft but solid fiber that was able to support its own weight for lengths up to 1.5 m.
After exiting the spinneret, the fiber traveled a distance of 15 cm inside the coagulant and was then rolled up onto a rotating spool placed inside the coagulation bath. The spool was attached directly to a Heidolph "RZR 2052" controlled stirrer which was used to determine its rotation speed. Fiber linear take-up speed (collection rate) in m/s was calculated by multiplying the spool's circumference by its rotation speed (in RPM). In order to prevent fiber breakage, the injection angle (the angle at which the fiber exits the spinneret) was kept as small as possible. As soon as the fiber emerged from the spinneret, it was picked up using tweezers and wound onto the rotating spool for collection.
The injection flow rate of the dope was kept constant at 30 µL/min, giving a fiber production rate of 0.026 m/s at the exit from the spinneret. In order to produce undrawn fibers, injection and take-up speeds were equilibrated (hence, Draw Ratio 1:1 (DR1:1), i.e., the take-up speed was maintained at 0.026 m/s, leaving a free-floating fiber section between the spinneret and the spool. To introduce drawing, the take-up speed was increased while the injection rate was maintained constant. To obtain a DR of 1:2 for example, the take-up speed was set to 0.052 m/s. Fibers were injected at 7 different draw ratios: DR 1:1, 1:3.3, 1:4.9, 1:6.5, 1:8.1, 1:9.8 and 1:11.4. The maximum take-up speed that was stably achieved was 0.295 m/s at DR 1:11.4.
After spinning, the fibers, wound on the spool, were incubated in the coagulation buffer (FIG. 1-A(ii)) for 24 h to ensure neutralization of the dope. The coagulation buffer comprised of phosphate buffered saline (PBS):10 mM phosphate, 2.7 mM KCl and 0.137 M NaCl at pH 7.4, to which 2 M NaCl was added.
Two crosslinking methods were tested—glutaraldehyde (GTA) for maximal mechanical performance and sustainability, and EDC/NHS, for fibers to be used in cell culture. Either 0.1% glutaraldehyde or 50 mM 1-ethyl-3-(3-dimethylaminopropyl) carbodiimide (EDC) and 100 mM N-hydroxysuccinimide (NHS) were added directly to the coagulation buffer followed by further 24 hr incubation at room temperature. After crosslinking, the fibers were rinsed three times in purified water to remove crosslinker and salt residues.
For drying, the fibers were gradually dehydrated by 2-hour incubations in solutions of increasing ethanol concentrations (50%, 75%, 87% 95%, 100%) (FIG. 1A(iii)). After dehydration, the fibers were dried by critical point drying process (FIG. 1A(iv)), to prevent fusion of their outer surfaces as a result of water adhesion forces. At least 20 meters were produced from each draw ratio. The dried, finished fibers (FIG. 1A(v)) were kept at room temperature for further testing.
Critical Point Drying (CPD):
CPD was performed on a Quorum Technologies k850 critical point dryer. Fibers on spools were removed from 100% ethanol and introduced into the CPD chamber, pre-cooled to 5° C. After sealing the chamber, the ethanol was exchanged with liquid $CO_2$. This was performed by filling the chamber with the liquefied gas, rinsing for 2 minutes and then emptying the chamber and refilling with fresh gas; the process was repeated three times, or until no ethanol was detected in the exhaust gases. The chamber was filled again, and the temperature was increased to 32° C., a temperature at which the $CO_2$ undergoes sublimation, reaching a pressure of 1,150 PSI. The pressure was then gradually released, taking heed not to lower more than 100 PSI/min.

Mechanical Characterization:

Tensile testing of the fibers was performed on an Instron model 3345 machine equipped with the "Bluehill Lite" analysis software. A Honeywell model 31 low load cell, with a 50 g load range was used. The load cell was calibrated with a 20 g standard weight before each test session. Testing was performed at a 2 mm/min rate.

At least 15 m of fiber were produced for each draw ratio, from which five 50 mm samples were chosen at random. Fiber samples were well affixed in a 1 mm-thick polypropylene frame between two layers of double-sided tape; tests were performed to confirm that no slippage occurred. The fiber samples were positioned so that at least 1 cm ran through the tape on each side of the sample, and the tested region was 20 mm long.

For wet testing, the fiber was dipped into PBS for 3 hours before the test. Fiber diameter and sample length were input to the Bluehill software, which generated the stress-strain graphs, ultimate tensile strength (UTS), extension, energy at break and Young's modulus data. Prior to testing, the diameter of every fiber sample was determined by a Nikon eclipse 80i microscope, fitted with Abrio CRI system for imaging and analysis (see below).

Swelling Test:

To quantitate fiber swelling, five fiber samples, each measuring 30 mm long, were randomly chosen from different regions of a long (>20 m) fiber spool. Dry fiber diameters were determined at 5 points along the fiber with the aid of a Nikon eclipse 80i microscope, fitted with Abrio CRI system for imaging and analysis (see below). The fiber samples were rehydrated in PBS for three hours and the diameter was re-measured. The swelling percent was calculated as: ((wet diameter−dry diameter)/dry diameter)*100.

Scanning Electron Microscopy (SEM):

Dry fiber samples were placed on an aluminum stub using carbon tape, and then coated with Au/Pd in a high-vacuum coater for 60 seconds with a 2 A current. The estimated coating thickness was 3 nm. SEM was performed with an FEI "Sirion" microscope.

Polarized Light Microscopy and Image Analysis:

Polarized microscopy was performed with a Nikon eclipse 80i microscope, fitted with an Abrio system (CRI, Germany) for polarized imaging and analysis[13]. The optical system includes a CCD camera, liquid-crystal (LC) compensator optic and a circular polarizer/interference filter optic (CP/IF). Image acquisition and analysis were performed using the Abrio 2.2 software. Background and specimen images were captured under identical conditions (546 nm).

Construction of Scaffold for Cell Culture:

EDC/NHS cross-linked fibers were stretched over glass coverslips measuring 24×20×0.1 mm, previously treated with "sigmacote" (Sigma-Aldrich) to render them more hydrophobic. Fiber samples were anchored to coverslips on both sides using a drop of silicone adhesive (DOW CORNING 732). This formed a >15 mm fiber section secured between the anchoring points and resting on the treated glass surface. Each coverslip formed an experimental unit that contained six fiber samples, one from every draw ratio. A 2 mm gap was left between the fibers. After curing of the adhesive (room temperature, 24 hours) the constructs were placed inside sterile six-well plates and rehydrated for 30 minutes in ddH$_2$O and sterilized by overnight incubation in isopropanol. They were then transferred into a new, sterile plate and rinsed 3 times in sterile ddH$_2$O for 30 minutes and once in growth medium for 30 minutes in a 37° C. incubator.

Rat Tenocyte Isolation:

Tenocytes were extracted from rat Achilles tendon according to a previously reported procedure[14]. Briefly. Achilles tendons were dissected from young rats, cut into small pieces, and transferred into a culture flask containing Dulbecco's modified Eagle's medium (DMEM) with 50% fetal calf serum (FCS). After 24 hours at 37° C., an additional 3 mL DMEM with 50% FCS were added, and incubation continued for another 24 hours at 37° C. During the incubation period, tenocytes migrate out of the tissue and adhere to the flask. Following removal of the tissue and old medium, fresh DMEM plus 10% FCS and 1% penicillin-streptomycin (PS) (BIOLAB Ltd, Israel) was added and the cells were cultivated for 96 hours at 37° C. For subculture, cells were detached via a brief trypsin EDTA (Biological Industries, Israel) treatment, and then reseeded.

Cell Alignment Assay:

Cells (100,000 in 1 mL DMEM plus 10% FCS) were spread on the coverslip fiber scaffold in each well and left to adhere for 30 minutes. Wells were then filled with medium. The plates were incubated in 5% CO$_2$ incubator at 37° C. for 72 hours. The assay was terminated by aspiration of the medium and the cells were fixed by addition of 3% paraformaldehyde (PFA) supplemented with 0.5% triton X-100 for 3 minutes incubation, followed by a 20 minutes incubation in 3% PFA at 37° C. After 3 washes in PBS, 1% skim milk was added as a blocking solution and samples were incubated for 1 hr. DAPI (300 nM) and Pahlloidin (50 nM) (both from Thermo Fisher Scientific) were added, and after 1 hour incubation, the samples were washed 3 times with PBS, and then stored in the dark at 4° C. for up to 1 week before imaging.

Fluorescent Image Acquisition:

Imaging of the fluorescently-labeled samples was performed with an EVOS 6500-FL fluorescent microscope (Life Technologies). A 20× magnification was used for all sample and control pictures. For imaging the DAPI stained nuclei, 360 nm excitation and 447 nm emission were used. For the Pahlloidin-stained actin fibers, 530 nm excitation and 593 nm emission were used.

Image Analysis:

The "CellProfiler" version 2.1.1 program[15] was used for image analyses. The fluorescent images of the DAPI stain (461 nm) were used as input files. In the first analysis stage, the nuclei were identified as primary objects based on the following parameters: typical object diameter—20 to 40 pixels, threshold strategy—global, thresholding method—MoG, smoothing method for thresholding—automatic, threshold correction factor—2, method to distinguish clamped objects—shape, method to draw dividing lines between clumped objects—intensity. These parameters were selected after multiple iterations and manual verification of accurate identification of the number and shape of nuclei in all experimental groups. The same parameters were used for all experimental groups and controls. In the second analysis stage, the "MeasureObjectSizeShape" module was used. This module assigns the best-fitting ellipse to every identified nucleus, and quantifies the following parameters:

"MajorAxisLength": The length (in pixels) of the major axis of the fitted ellipse.

Area: The actual number of pixels in the identified nucleus image.

Orientation: The angle (in degrees ranging from −90° to 90°) between the x-axis and the major axis of the fitted ellipse. The fiber axis was set parallel to the x-axis (0 degrees).

Statistical Analysis:

Statistical analysis was performed with JMP pro 10 software. One-way analysis of variance (ANOVA) was used for multiple comparisons. For pairwise comparisons, a two sample t-test was used. Statistical significance was set at $P<0.05$. Normality of the populations sampled was assumed. Homogeneity of variances of the populations was verified by Bartlett's and Levene's tests.

Numerical data are presented as mean±standard deviation (SD). Means and SDs were calculated using Excel software (Microsoft Corporation).

Differential Scanning Calorimetry (DSC):

Fiber samples weighing between 2.0 to 4.0 mg were incubated in PBS for three days before testing. The samples were placed in aluminum sample pans, covered with PBS and sealed. PBS was used as reference, and weights of the reference and sample pans were matched. The temperature range tested was from 5° C. to 95° C., at a 5 K/min scan rate. Tests were performed under dynamic nitrogen atmosphere (50 mL/min) on a Shimadzu DSC-50.

Results

Effect of Draw Ratio on Fiber Structure and Morphology

A sample of dried, GTA crosslinked fibers on a spool (spun at DR 1:8.1) is shown in FIG. 1B. Fiber diameter sharply decreased with increasing draw ratio (FIG. 1C); whereas at DR 1:1 the fiber diameter was 35 µm, at DR 1:8.1 it was reduced to 10 µm, and at the maximal draw ratio of 1:11.4 the diameter was 8 µm. Accordingly, the length spun from 1 mg of protein was increased from 1.7 m at DR1:1 to 19.7 m at DR1:11.4. The fiber production rate was over 760 m/hr at DR 1:8.1 and over a 1,000 m/hr at DR 1:11.4.

Scanning electron microscopy was employed to characterize fiber morphology. The impact of draw ratio on the orientation of the fiber's outer surface was clearly visible. Undrawn fibers (DR 1:1) displayed a very rough surface with deep grooves and pits (FIG. 2A), reminiscent of a wrinkled cloth. When drawing was introduced at DR 1:3.3 (FIG. 2B), a substantial alteration in fiber surface was observed. The fiber surface became much smoother and homogenous; some crevices were observed, but were shallower than in the undrawn fibers, and most of them were aligned with the fiber axis. As the draw ratio was further increased to DR 1:4.9, the crevices on the fiber surface became even shallower, and were almost entirely oriented with the fiber axis. This trend continued throughout all tested draw ratios, and culminated with the highest draw ratio (DR 1:11.3), that yielded the smoothest and most homogenous fibers (FIGS. 2D-G).

The fractured fiber ends revealed a core-shell structure, in which both components were affected by the draw ratio. Undrawn fibers (DR 1:1, FIG. 3A) had a thick shell that appeared to be tightly packed and fused, with a wrinkled morphology. The inner core (FIG. 3B) was composed of fine, well-separated fibrils, that formed a wavy pattern (crimp), that were loosely oriented with the fiber axis, and had a wavelength of approximately 2 µm. Multiple voids between the fibrils were clearly visible. When the draw ratio was increased to DR 1:4.9, the core-shell structure was still maintained, but the outer shell was thinner (FIG. 3C), appeared to be less fused and was much better aligned and oriented. The core was composed of thin, well-separated fibrils. The fibrils appear to be better aligned (FIG. 3D), with greater packing density and smaller voids between them. The crimp pattern was less pronounced and was mainly observed in the center of the core.

In contrast, fibers drawn at the maximal draw ratio, DR1:11.4 featured a uniform, continuous morphology, and no core-shell structure was discerned (FIG. 3E). The bulk of the fiber, which appeared fused, broke under pressure (see right side of FIG. 3E) revealing highly aligned, highly oriented and densely packed fibrils.

Effect of Draw Ratio on Order and Alignment

Polarized microscopy is a tool commonly used to characterize the degree of fibrillar order and orientation of collagen samples, as reflected by birefringence and slow optical axis[16]. The wet spun fibers were analyzed by the "Abrio" polarized light microscopy system that quantifies retardance (in nanometers) and determines the orientation azimuth of the slow optical axis of the sample by measuring the relative phase shift between two orthogonally polarized light waves[13]. For collagen, the slow optical axis is aligned with the molecular axis[16a], and therefore, the given orientations are the molecular and fibrillar orientations of rhcollagen. For imaging purposes, the Abrio software generates a pseudo-color image, where color denotes the orientation of the slow optic axis and the intensity indicates retardance. The retardance is dependent on both the sample thickness and the degree of alignment.

A side-by-side display of fibers spun at different draw ratios is presented in FIGS. 4A-G. Insets at the top depict the retardance intensity along the white broken line that transverses the fibers perpendicular to their long-axes. Undrawn fibers (DR1:1, FIG. 4A) displayed a retardance pattern commensurate with a distinct core-shell structure. The intensity diagram at the top shows that the strongest retardance was recorded at the fiber circumference, and not at its core, where sample thickness was maximal. This pattern suggests a shell with higher fibrillar alignment and density, that envelopes a loosely packed core. When looking at a longitudinally cut fiber, a faint cyan region was seen along its center, indicating molecular and fibrillar alignment with the fiber axis. As the light transverses the entire fiber diameter in that region, where core thickness is maximal and shell thickness is minimal, the orientation reflected by the signal was attributed to the core.

When focusing on the area closer to the fiber fringes, where the shell component becomes more significant relative to the core, fibril orientation appeared weaker. Multiple small patches displaying 45° or even 90° fibril orientation relative to the fiber axis were observed. This finding is in agreement with the wrinkled and rough surface observed along the outer shell by SEM.

Figures 4A, 4B, 4C, 4D, 4E, 4F, 4G:
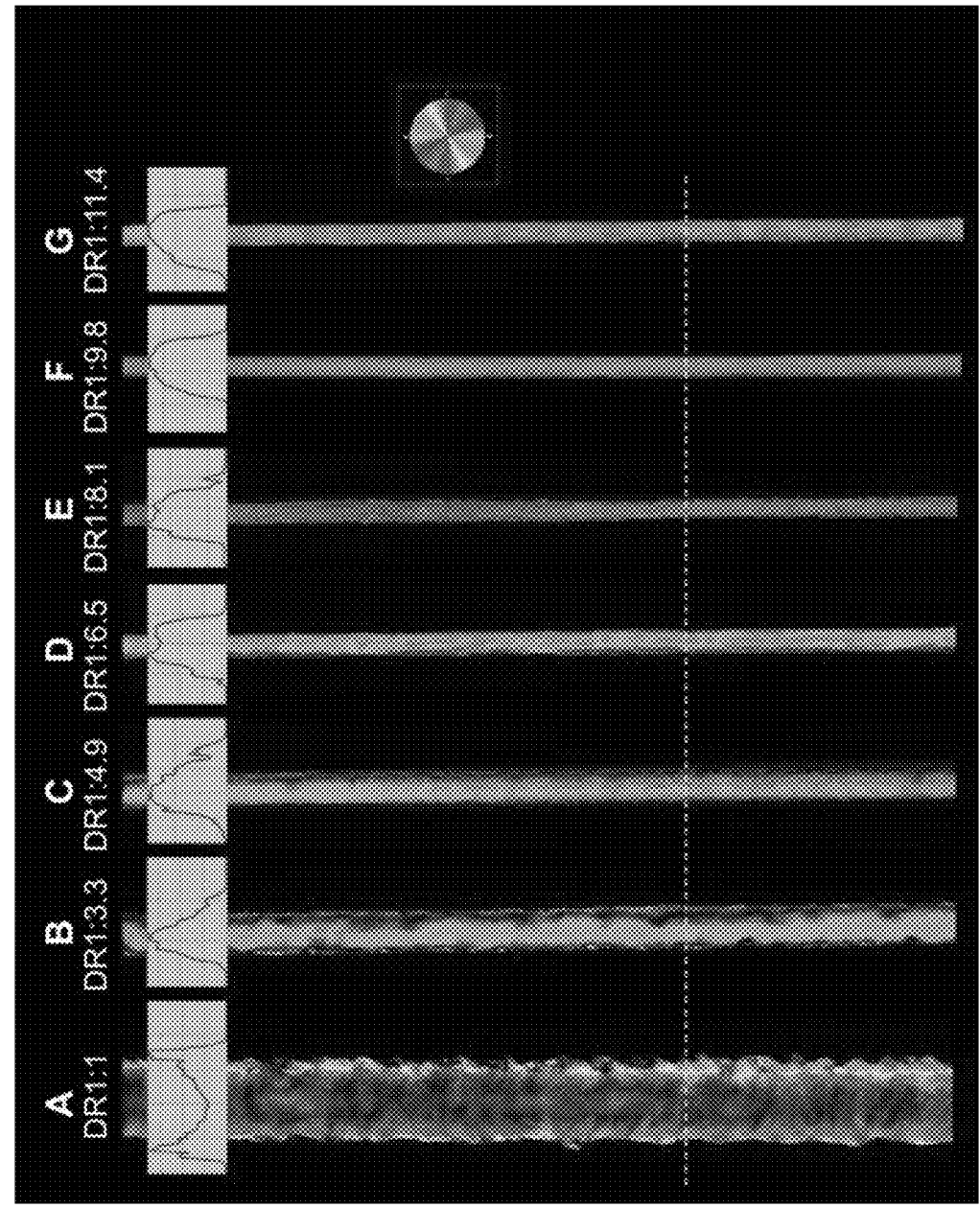

Fibers drawn at DR 1:3.3 appeared to have a fundamentally different intensity profile (FIG. 4B, top), with a maximal retardance measured along their center, at the thickest region, which declined toward the fringes. This indicates that the alignment and density in the core was more substantial relative to the shell, where it only became visible near the fiber fringes, where core thickness was small. The shape of the intensity diagram was not smooth, reflecting the surface roughness observed in the SEM images. Fibrillar alignment was strong and the fibrils were well oriented with the fiber axis throughout the bulk of the core, as reflected by the dominance of the cyan hue in the fiber center (FIG. 4B, body). The core appeared to be forming a faint crimp pattern, with a hue that shifted towards green when kinked right and towards blue when kinked left. In contrast, orientation was lost in the fiber shell, as manifested by multiple color patches, indicating orientations deviating from the fiber axis by as much as 90°.

This trend was maintained in fibers prepared at DR 1:4.9. Fibers displayed a rounder intensity diagram (FIG. 4C, top), reflecting further thinning of the non-oriented shell. The fiber core was smoother, with a very weak crimp still visible as small kinks sparsely dispersed throughout (FIG. 4C, body). The shell was almost absent, and appeared as a very thin un-oriented layer, mainly on the right side of the fiber. At DRs 1:6.5 and 1:8.1 (FIGS. 4D, E, body), fibers lacked the outer shell altogether, and displayed a homogenously oriented body (only the cyan hue was visible). However, intensity was not uniform, reflecting the presence of some crevices and folds or possible density changes along the fiber axis. DR 1:8.1 and 1:11.4 fibers (FIGS. 4F, G, top) featured a smooth circular shape, with well-defined edges. The fiber bodies showed both high uniformity and strong alignment of the monomers and fibrils, reflected by the strong intensity and uniform cyan color (FIGS. 4F, G, body).

In order to quantify and compare the degree of order in fibers spun at the different DRs, their birefringence was calculated and plotted against the draw ratio (see FIG. 10). A low level of birefringence was recorded in undrawn fibers (DR 1:1), and only slightly increased in DR 1:3.3 fibers. A strong rise was observed, however, when DR was further elevated to 1:4.9 which formed a local peak. Lower birefringence was then measured for DR 1:6.5 and 8.1 fibers, followed by a strong and steady birefringence increase for the two remaining draw ratios, 1:9.8 and 1:11.1.

Effect of Drawing on Mechanical Performance

To characterize the effect of fiber draw ratio on the mechanical properties of the drawn fibers, tensile stress and strain performance of the glutaraldehyde crosslinked fibers were assessed (FIGS. 5A-D). As shown in FIG. 5A, fiber ultimate tensile strength (UTS) increased linearly as DR was increased up to 1:8.3 ($p<0.05$). After this point, the UTS plateaued and even slightly declined at DR 1:11.4. A similar pattern was observed for the fibers Young's modulus (FIG. 5B), although statistical significance was not detected between each draw ratio increment. It was however detected between every second draw ratio. The peak modulus was in DR 1:8.1 fibers, followed by a steeper decline.

Tensile strain at break (FIG. 5C) peaked at a draw ratio of 1:3.3, and was larger than that measured for DR 1:1 fibers ($P<0.05$). No other significant differences in tensile strain at break were measured between other fiber groups, but the general trend was of gradual decline with increasing draw ratio.

Fiber toughness (energy at break) is actually a function of the tensile stress and strain, and therefore reflects their combined trends. The highest value was obtained at draw ratio 1:8.1, beyond which it gradually decreased (FIG. 5D). The steepest incline was observed between DR 1:1 and DR 1:3.1, ascribed to the strain increase between them.

Crosslinking

Two crosslinking systems were used: Glutaraldehyde (GTA) and 1-Ethyl-3-(3-dimethylaminopropyl) carbodiimide (EDC). Fiber swelling was quantified as a measure of fiber crosslinking effectiveness. FIG. 6 shows the swelling behavior of GTA crosslinked fibers. Fiber swelling strongly correlated with draw ratio, where fibers formed under high DRs swelled substantially more than those collected under lower DRs. At DR 1:11.4, the fibers swelled by 80%, whereas DR 1:1 fibers swelled by only 20%.

Figure 7A:
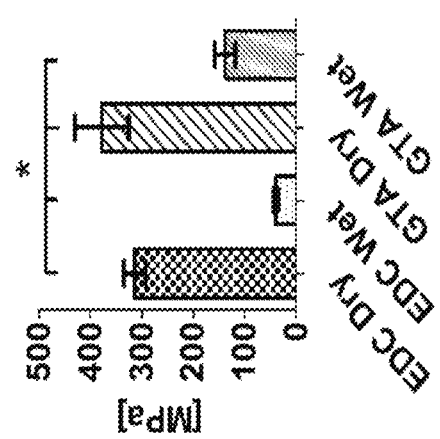
Figure 7B:
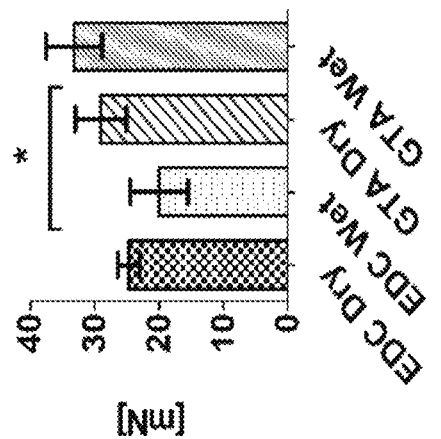
Figure 7C:
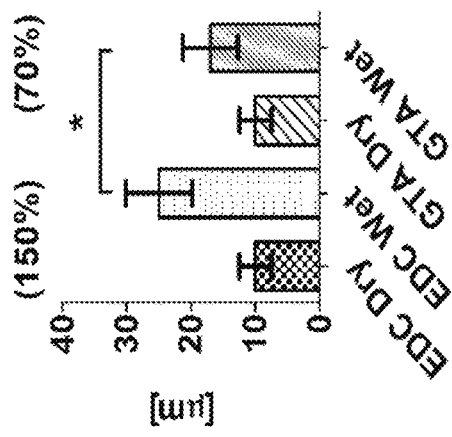
Figure 7D:
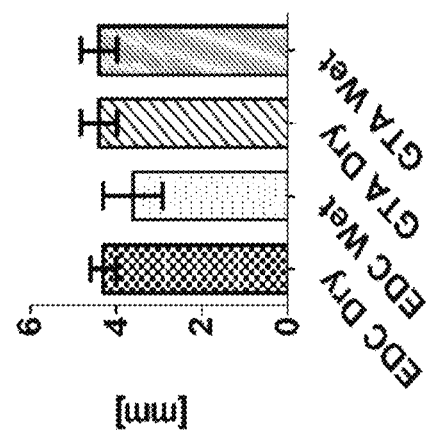

To compare the different crosslinking approaches (i.e., GTA and EDC), fibers drawn at DR 1:8.1 (the draw ratio that yielded the best mechanical performance in the GTA crosslinked fibers) were crosslinked and compared. FIG. 7A shows the dry diameter, wet diameter and swelling percent recorded for DR 1:8.1 fibers crosslinked using either of the two methods. EDC-crosslinked fibers swelled approximately two-fold more than the GTA-crosslinked fibers ($P<0.01$). No significant difference in fiber extension at break was observed between the different crosslinking treatments or hydration states (FIG. 7B). The dry fiber stress at break was approximately 20% lower for dry EDC-crosslinked (314 MPa) versus dry GTA-crosslinked fibers (378 MPa) (FIG. 7C). The difference between crosslinkers was greatly enhanced in wet fibers; stress at break of wet EDC-crosslinked fibers (40 MPa) was approximately 250% lower than that of wet GTA-crosslinked fibers (138 MPa). The measured load at break was not different for dry versus hydrated fibers crosslinked with identical reagents (FIG. 7D), but GTA-crosslinked fibers broke under a higher load than EDC-crosslinked fibers ($P<0.05$), both in dry and hydrated states.

Alignment of Rat Tenocytes

To test the effect of draw ratio on cell alignment, rat tenocytes were grown on the EDC-crosslinked fibers. In the control group the nuclei were generally round in shape, and were not oriented in any specific direction (FIG. 8A). Undrawn fibers showed a low degree of nuclear orientation, while cell bodies were still amorphous at large. When drawing was introduced, cell bodies and nuclei became elongated and aligned along the fiber axis, which became thinner with increasing draw ratio.

As it has previously shown that the nucleus is mechanically integrated with the cell body[20], and therefore reflects cell orientation, shape and configuration[21], cell alignment was inferred by quantifying the major axis length and orientation of each nucleus. Body shape was not quantified because reliable and repeatable image separation could not be achieved.

FIG. 8B shows the probability density of the cells' nuclei major axis orientation.

The control cells' nuclear orientation distribution (bottom, red) is rather flat, indicating they are not oriented in any particular direction. Cells cultured on undrawn fibers (DR1:1) show a low degree of nuclear orientation, as visualized by the flattened bell shape curve of their probability density (dark green, second from bottom), centered between 40 and −40 degrees. Upon introduction of drawing (DR 1:3.3), a marked increase in nuclear orientation was observed, with most cells presenting a nuclear orientation between 20° and −20°. When the draw ratio was further increased to DR 1:4.9, a local peak in orientation was seen, followed by a small decline at draw ratios DR 1:6.5 and 1:8.1. Another substantial increase in the nuclear orientation was observed for DR1:9.8 fibers, where the vast majority of nuclei were oriented between 10° and −10°. For technical reasons, the last draw ratio (DR1:11.4) fibers were omitted from this experiment.

FIG. 8C presents the length of cell's nucleus to area ratio. This parameter was used as an indicator of a prolate cell shape, and the division by the area was introduced to reduce the effect of nuclear size variability. The lowest ratio of length to area (reflecting a round shape) was observed among control cells. A strong increase ($P<0.05$) was noted among cells cultured on undrawn fibers (DR 1:1), followed by an additional increase when drawing was introduced ($P<0.05$). This trend continued until a local peak was obtained in cultures with DR 1:4.9 fibers. Draw ratios DR 1:6.5 and 1:8.1 showed a small decrease in the length/area ratio, while the largest ratio was obtained from cells grown on fibers with the highest draw ratio (DR 1:9.8).

TABLE 2 fiber dimensions and spinning rate

| Draw Ratio | Dry Diameter [μm] | Length per mg [m] | Spinning rate [m/h] |
|---|---|---|---|
| DR1:1 | 35 ± 3.1 | 1.7 ± 0.1 | 91 |
| DR1:3.3 | 20 ± 2.7 | 5.6 ± 0.3 | 304 |
| DR1:4.9 | 14 ± 2.3 | 8.5 ± 0.4 | 456 |
| DR1:6.5 | 11 ± 1.3 | 11.3 ± 0.6 | 608 |
| DR1:8.1 | 10 ± 2.5 | 14.1 ± 0.7 | 761 |
| DR1:9.8 | 9 ± 1.3 | 16.9 ± 0.8 | 913 |
| DR1:11.4 | 8 ± 0.8 | 19.7 ± 1.0 | 1,065 |

TABLE 3

A summary of the mechanical performance (hydrated) of the best performing collagen fibers published over the last 30 years

| Reference | Crosslinking Method | Strain at Break | Modulus | Stress at Break |
|---|---|---|---|---|
| Current Study | GTA | 1.95 ± 20.5 | 153 ± 888 | 31 ± 151 |
| Dunn et.al.[6i] | GTA | NA | NA | 38 ± 110 |
| Caves et.al.[25i] | GTA | 1.9 ± 14.3 | 173 ± 775 | 19.2 ± 93.9 |
| Wang et.al.[25e] | DHT† | 1.92 ± 11.87 | 205.9 ± 895 | 31.4 ± 91.8 |
| Koob et.al.[33] | NDGA | 1 ± 11 | 38 ± 696 | 10.1 ± 91.2 |
| Kato et.al.[6h] | GTA | 2.7 ± 16.1 | 96.6 ± 407 | 17.2 ± 66.2 |
| Pins et.al.[25h] | DHT† | 1.68 ± 13.8 | 101.1 ± 503.9 | 11.82 ± 57.1 |
| Gentleman et.al.[34] | EDC | NA | 76.3 ± 484.7 | 13.4 ± 50 |

Combined Effect of Dope Concentration and Drawing

To test the combined effect of dope concentration and drawing, three dope concentrations were tested (in addition to the 30 mg/mL concentration previously tested). The highest concentration tested was 70 mg/mL, beyond which viscosity became prohibitive while working with the ceramic 30 μm spinneret.

FIG. 14 shows the dependence of the UTS on the draw ratio for all the tested concentrations. The two higher concentrations (shown in black and blue for 70 and 50 mg/mL, respectively) could only be drawn to DR1:8.1, beyond which spinning became discontinuous. Fibers extruded from a 70 mg/mL concentration showed a peak UTS of 485 MPa at DR1:3.3. When dope concentration was reduced to 50 mg/m/L, a peak of 471 MPa was reached at DR1:4.9. At 30 mg/mL, a 378 MPa peak was reached at DR1:8.1, and at the lowest concentration of 10 mg/mL, the peak UTS of 266 MPa was reached at DR1:9.8.

REFERENCES 1. (a) Coburn, J.; Gibson, M.; Bandalini, P. A.; Laird, C.; Mao, H.-Q.; Moroni, L.; Seliktar, D.; Elisseeff, J., Biomimetics of the extracellular matrix: an integrated three-dimensional fiber-hydrogel composite for cartilage tissue engineering. Smart structures and systems 2011, 7 (3), 213; (b) Tamayol, A.; Akbari, M.; Annabi, N.; Paul, A.; Khademhosseini, A.; Juncker, D., Fiber-based tissue engineering: Progress, challenges, and opportunities. Biotechnology advances 2013, 31 (5), 669-687; (c) Murugan, R.; Ramakrishna, S., Nano-featured scaffolds for tissue engineering: a review of spinning methodologies. Tissue engineering 2006, 12 (3), 435-447.
2. Van Lieshout, M.; Vaz, C.; Rutten, M.; Peters, G.; Baaijens, F., Electrospinning versus knitting: two scaffolds for tissue engineering of the aortic valve. Journal of Biomaterials Science, Polymer Edition 2006, 17 (1-2), 77-89.
3. Lu, H. H.; Cooper, J. A.; Manuel, S.; Freeman, J. W.; Attawia, M. A.; Ko, F. K.; Laurencin, C. T., Anterior cruciate ligament regeneration using braided biodegradable scaffolds: in vitro optimization studies. Biomaterials 2005, 26 (23), 4805-4816.
4. Ateshian, G. A., Artificial cartilage: weaving in three dimensions. Nature materials 2007, 6 (2), 89-90.
5. Mano, J.; Silva, G.; Azevedo, H. S.; Malafaya, P.; Sousa, R.; Silva, S.; Boesel, L.; Oliveira, J. M.; Santos, T.; Marques, A., Natural origin biodegradable systems in tissue engineering and regenerative medicine: present status and some moving trends. Journal of the Royal Society Interface 2007, 4 (17), 999-1030.
6. (a) Griset, E. J.; Reissmann, T. L.; Joseph, N., Method of producing a collagen strand. Google Patents: 1963; (b) Braun, B.; Braun, E., Production of collagen strands. Google Patents: 1956; (c) Goldstein, J. D.; Tria, A.; Zawadsky, J.; Kato, Y.; Christiansen, D.; Silver, F., Development of a reconstituted collagen tendon prosthesis. J Bone Joint Surg Am 1989, 71, 1183-1191; (d) Pins, G. D.; Silver, F. H., A self-assembled collagen scaffold suitable for use in soft and hard tissue replacement. Materials Science and Engineering: C 1995, 3 (2), 101-107; (e) Meyer, M.; Baltzer, H.; Schwikal, K., Collagen fibres by thermoplastic and wet spinning. Materials Science and Engineering: C 2010, 30 (8), 1266-1271; (f) Zeugolis, D.; Paul, R.; Attenburrow, G., Extruded collagen fibres for tissue-engineering applications: influence of collagen concentration and NaCl amount. Journal of Biomaterials Science, Polymer Edition 2009, 20 (2), 219-234; (g) Zeugolis, D.; Paul, R.; Attenburrow, G., Post-self-assembly experimentation on extruded collagen fibres for tissue engineering applications. Acta biomaterialia 2008, 4 (6), 1646-1656; (h) Kato, Y. P.; Christiansen, D. L.; Hahn, R. A.; Shieh, S. J.; Goldstein, J. D.; Silver, F. H., Mechanical properties of collagen fibres: a comparison of reconstituted and rat tail tendon fibres. Biomaterials 1989, 10 (1), 38-42; (i) Dunn, M. G.; Avasarala, P. N.; Zawadsky, J. P., Optimization of extruded collagen fibers for ACL reconstruction. Journal of biomedical materials research 1993, 27 (12), 1545-1552; (j) Enea, D.; Henson, F.; Kew, S.; Wardale, J.; Getgood, A.; Brooks, R.; Rushton, N., Extruded collagen fibres for tissue engineering applications: effect of crosslinking method on mechanical and biological properties. Journal of Materials Science: Materials in Medicine 2011, 22 (6), 1569-1578.
7. (a) Vollrath, F.; Knight, D. P., Liquid crystalline spinning of spider silk. Nature 2001, 410 (6828), 541-8; (b) Lazaris, A.; Arcidiacono, S.; Huang, Y.; Zhou, J.-F.; Duguay, F.; Chretien, N.; Welsh, E. A.; Soares, J. W.; Karatzas, C.

N., Spider silk fibers spun from soluble recombinant silk produced in mammalian cells. *Science* 2002, 295 (5554), 472-476; (c) Vollrath, F.; Knight, D.; Hu, X., Silk production in a spider involves acid bath treatment. *Proceedings of the Royal Society of London B: Biological Sciences* 1998, 265 (1398), 817-820; (d) Knight, D.; Vollrath, F., Liquid crystals and flow elongation in a spider's silk production line. *Proceedings of the Royal Society of London B: Biological Sciences* 1999, 266 (1418), 519-523.

8. Shen, Y.; Johnson, M. A.; Martin, D. C., Microstructural characterization of *Bombyx mori* silk fibers. *Macromolecules* 1998, 31 (25), 8857-8864.

9. (a) Knight, D. P.; Hunt, S., Fine structure of the dogfish egg case: a unique collagenous material. *Tissue and Cell* 1976, 8 (1), 183-193; (b) Knight, D. P.; Feng, D.; Stewart, M., Structure and function of the salachian egg case. *Biological Reviews* 1996, 71 (1), 81-111; (c) Luong, T.-T.; Boutillon, M.-M.; Garrone, R.; Knight, D. P., Characterization of Selachian Egg Case Collagen. *Biochemical and biophysical research communications* 1998, 250 (3), 657-663; (d) Knupp, C.; Chew, M.; Squire, J., Collagen packing in the dogfish egg case wall. *Journal of structural biology* 1998, 122 (1), 101-110.

10. (a) Harrington, M. J.; Waite, J. H., pH-dependent locking of giant mesogens in fibers drawn from mussel byssal collagens. *Biomacromolecules* 2008, 9 (5), 1480-1486; (b) Harrington, M. J.; Waite, J. H., How nature modulates a fiber's mechanical properties: mechanically distinct fibers drawn from natural mesogenic block copolymer variants. *Advanced Materials* 2009, 21 (4), 440-444; (c) Hassenkam, T.; Gutsmann, T.; Hansma, P.; Sagert, J.; Waite, J. H., Giant bent-core mesogens in the thread forming process of marine mussels. *Biomacromolecules* 2004, 5 (4), 1351-1355.

11. Ebrahimi, D.; Tokareva, O.; Rim, N.; Wong, J. Y.; Kaplan, D. L.; Buehler, M. J., Silk—its mysteries, how it's made, and how it's used. *ACS Biomaterials Science & Engineering* 2015.

12. Stein, H.; Wilensky, M.; Tsafrir, Y.; Rosenthal, M.; Amir, R.; Avraham, T.; Ofir, K.; Dgany, O.; Yayon, A.; Shoseyov, O., Production of bioactive, post-translationally modified, heterotrimeric, human recombinant type-I collagen in transgenic tobacco. *Biomacromolecules* 2009, 10 (9), 2640-5.

13. Eder, M.; Lütz-Meindl, U.; Weiss, I. M., Non-invasive LC-PolScope imaging of biominerals and cell wall anisotropy changes. *Protoplasma* 2010, 246 (1-4), 49-64.

14. Pufe, T.; Petersen, W.; Tillmann, B.; Mentlein, R., The angiogenic peptide vascular endothelial growth factor is expressed in foetal and ruptured tendons. *Virchows Archiv* 2001, 439 (4), 579-585.

15. (a) Carpenter, A. E.; Jones, T. R.; Lamprecht, M. R.; Clarke, C.; Kang, I. H.; Friman, O.; Guertin, D. A.; Chang, J. H.; Lindquist, R. A.; Moffat, J.; Golland, P.; Sabatini, D. M., CellProfiler: image analysis software for identifying and quantifying cell phenotypes. *Genome Biol* 2006, 7 (10), R100; (b) CellProfiler. www(dot)cellprofiler (dot)org.

16. (a) Whittaker, P.; Canham, P. B., Demonstration of quantitative fabric analysis of tendon collagen using two-dimensional polarized light microscopy. *Matrix* 1991, 11 (1), 56-62; (b) Bromage, T. G.; Goldman, H. M.; McFarlin, S. C.; Warshaw, J.; Boyde, A.; Riggs, C. M., Circularly polarized light standards for investigations of collagen fiber orientation in bone. *The Anatomical Record Part B: The New Anatomist* 2003, 274 (1), 157-168; (c) Wolman, M.; Kasten, F., Polarized light microscopy in the study of the molecular structure of collagen and reticulin. *Histochemistry* 1986, 85 (1), 41-49; (d) Nieminen, M. T.; Rieppo, J.; Töyras, J.; Hakumäki, J. M.; Silvennoinen, J.; Hyttinen, M. M.; Helminen, H. J.; Jurvelin, J. S., T2 relaxation reveals spatial collagen architecture in articular cartilage: a comparative quantitative MRI and polarized light microscopic study. *Magnetic resonance in medicine* 2001, 46 (3), 487-493.

17. Kato, Y. P.; Silver, F. H., Formation of continuous collagen fibres: evaluation of biocompatibilily and mechanical properties. *Biomaterials* 1990, 11 (3), 169-175.

18. (a) Huang-Lee, L. L.; Cheung, D. T.; Nimni, M. E., Biochemical changes and cytotoxicity associated with the degradation of polymeric glutaraldehyde derived cross-links. *Journal of biomedical materials research* 1990, 24 (9), 1185-1201; (b) Gough, J. E.; Scotchford, C. A.; Downes, S., Cytotoxicity of glutaraldehyde crosslinked collagen/poly (vinyl alcohol) films is by the mechanism of apoptosis. *Journal of biomedical materials research* 2002, 61 (1), 121-130.

19. Fagerholm, P.; Lagali, N. S.; Ong, J. A.; Merrett, K.; Jackson, W. B.; Polarek, J. W.; Suuronen, E. J.; Liu, Y.; Brunette, I.; Griffith, M., Stable corneal regeneration four years after implantation of a cell-free recombinant human collagen scaffold. *Biomaterials* 2014, 35 (8), 2420-2427.

20. Maniotis, A. J.; Chen, C. S.; Ingber, D. E., Demonstration of mechanical connections between integrins, cytoskeletal filaments, and nucleoplasm that stabilize nuclear structure. *Proceedings of the National Academy of Sciences* 1997, 94 (3), 849-854.

21. (a) Dalby, M. J.; Riehle, M. O.; Yarwood, S. J.; Wilkinson, C. D.; Curtis, A. S., Nucleus alignment and cell signaling in fibroblasts: response to a micro-grooved topography. *Experimental cell research* 2003, 284 (2), 272-280; (b) Xue, N.; Li, X.; Bertulli, C.; Li, Z.; Patharagulpong, A.; Sadok, A.; Huang, Y., Rapid Patterning of 1-D Collagenous Topography as an ECM Protein Fibril Platform for Image Cytometry. *PloS one* 2014, 9 (4).

22. Hearle, J. W., *High-performance fibres*. Elsevier: 2001.

23. Ahmed, D.; Hongpeng, Z.; Haijuan, K.; Jing, L.; Yu, M.; Muhuo, Y., Microstructural developments of poly (p-phenylene terephthalamide) fibers during heat treatment process: a review. *Materials Research* 2014, (AHEAD), 0-0.

24. Yaari, A.; Posen, Y.; Shoseyov, O., Liquid crystalline human recombinant collagen: the challenge and the opportunity. *Tissue Engineering Part A* 2013, 19 (13-14), 1502-1506.

25. (a) Fofonoff, T. W.; Bell, E., Apparatus and method for spinning and processing collagen fiber. Google Patents: 1996; (b) Zeugolis, D. I.; Paul, G. R.; Attenburrow, G., Cross-linking of extruded collagen fibers—A biomimetic three-dimensional scaffold for tissue engineering applications. *Journal of Biomedical Materials Research* Part A 2009, 89 (4), 895-908; (c) Kato, Y. P.; Dunn, M.; Zawadsky, J. P.; Tria, A.; Silver, F., Regeneration of Achilles tendon with a collagen tendon prosthesis. Results of a one-year implantation study. *The Journal of Bone & Joint Surgery* 1991, 73 (4), 561-574; (d) Kato, Y. P.; Silver, F. H. In *Properties of manually produced and automated continuous collagen fibers*, Engineering in Medicine and Biology Society, 1989. Images of the Twenty-First Century., Proceedings of the Annual International Conference of the IEEE Engineering in, IEEE: 1989; pp 843-844; (e) Ming-Che, W.; Pins, G. D.; Silver, F. H., Collagen fibres with improved strength for the repair of soft tissue injuries. *Biomaterials* 1994, 15 (7), 507-512; (f) Zeugolis, D. I.; Paul, R. G.; Attenburrow, G., Factors influencing the properties of reconstituted collagen fibers prior to self-assembly: animal species and collagen extraction method. *J Biomed Mater Res A* 2008, 86 (4), 892-904; (g) Pins, G. D.; Huang, E. K.; Christiansen, D. L.; Silver, F. H., Effects of static axial strain on the tensile properties and failure mechanisms of self-assembled collagen fibers. *Journal of Applied Polymer Science* 1997, 63 (11), 1429-1440; (h) Pins, G. D.; Christiansen, D. L.; Patel, R.; Silver, F. H., Self-assembly of collagen fibers. Influence of fibrillar alignment and decorin on mechanical properties. *Biophysical Journal* 1997, 73 (4), 2164-2172; (i) Caves, J. M.; Kumar, V. A.; Wen, J.; Cui, W.; Martinez, A.; Apkarian, R.; Coats, J. E.; Berland, K.; Chaikof, E. L., Fibrillogenesis in continuously spun synthetic collagen fiber. *J Biomed Mater Res B Appl Biomater* 2010, 93 (1), 24-38; (j) Siriwardane, M. L.; DeRosa, K.; Collins, G.; Pfister, B. J., Controlled formation of cross-linked collagen fibers for neural tissue engineering applications. *Biofabrication* 2014, 6 (1), 015012; (k) Cavallaro, J. F.; Kemp, P. D.; Kraus, K. H., Collagen fabrics as biomaterials. *Biotechnology and bioengineering* 1994, 43 (8), 781-791.
26. (a) Pope, D.; Keller, A., Alignment of macromolecules in solution by elongational flow; a study of the effect of pure shear in a four roll mill. *Colloid and Polymer Science* 1977, 255 (7), 633-643; (b) Lenstra, T.; Dogic, Z.; Dhont, J., Shear-induced displacement of isotropic-nematic spinodals. *The Journal of Chemical Physics* 2001, 114 (22), 10151-10162.
27. Schmitt, V.; Lequeux, F.; Pousse, A.; Roux, D., Flow behavior and shear induced transition near an isotropic/nematic transition in equilibrium polymers. *Langmuir* 1994, 10 (3), 955-961.
28. Um, I. C.; Ki, C. S.; Kweon, H.; Lee, K. G.; Ihm, D. W.; Park, Y. H., Wet spinning of silk polymer: II. Effect of drawing on the structural characteristics and properties of filament. *International journal of biological macromolecules* 2004, 34 (1), 107-119.
29. Fukae, R.; Maekawa, A.; Sangen, O., Gel-spinning and drawing of gelatin. *Polymer* 2005, 46 (25), 11193-11194.
30. Nelson, K. D.; Romero, A.; Waggoner, P.; Crow, B.; Borneman, A.; Smith, G. M., Technique paper for wet-spinning poly (L-lactic acid) and poly (DL-lactide-co-glycolide) monofilament fibers. *Tissue engineering* 2003, 9 (6), 1323-1330.
31. (a) Müller, M.; Riekel, C.; Vuong, R.; Chanzy, H., Skin/core microstructure in viscose rayon fibres analysed by X-ray microbeam and electron diffraction mapping. *Polymer* 2000, 41 (7), 2627-2632; (b) Morehead, F. F.; Sisson, W. A., Skin effect in viscose rayon. *Textile Research Journal* 1945, 15 (12), 443-450.
32. (a) Giraud-Guille, M. M.; Besseau, L.; Martin, R., Liquid crystalline assemblies of collagen in bone and in vitro systems. *J Biomech* 2003, 36 (10), 1571-9; (b) Giraud-Guille, M. M., Liquid crystallinity in condensed type I collagen solutions. A clue to the packing of collagen in extracellular matrices. *J Mol Biol* 1992, 224 (3), 861-73.
33. Koob, T. J.; Hernandez, D. J., Material properties of polymerized NDGA-collagen composite fibers: development of biologically based tendon constructs. *Biomaterials* 2002, 23 (1), 203-212.
34. Gentleman, E.; Lay, A. N.; Dickerson, D. A.; Nauman, E. A.; Livesay, G. A.; Dee, K. C., Mechanical characterization of collagen fibers and scaffolds for tissue engineering. *Biomaterials* 2003, 24 (21), 3805-3813.
35. (a) Hashemi, J.; Chandrashekar, N.; Slauterbeck, J., The mechanical properties of the human patellar tendon are correlated to its mass density and are independent of sex. *Clinical Biomechanics* 2005, 20 (6), 645-652; (b) Lewis, G.; Shaw, K. M., Tensile properties of human tendo Achillis: effect of donor age and strain rate. *The Journal of foot and ankle surgery* 1997, 36 (6), 435-445.
36. (a) Kastelic, J.; Palley, I.; Baer, E., A structural mechanical model for tendon crimping. *Journal of Biomechanics* 1980, 13 (10), 887-893; (b) Freed, A. D.; Doehring, T. C., Elastic model for crimped collagen fibrils. *Journal of biomechanical engineering* 2005, 127 (4), 587-593; (c) Fratzl, P.; Misof, K; Zizak, I.; Rapp, G.; Amenitsch, H.; Bernstorff, S., Fibrillar structure and mechanical properties of collagen. *J Struct Biol* 1998, 122 (1-2), 119-22.
37. (a) Gupta, B.; Revagade, N.; Anjum, N.; Atthoff, B.; Hilborn, J., Preparation of poly (lactic acid) fiber by dry-jet-wet-spinning. I. Influence of draw ratio on fiber properties. *Journal of applied polymer science* 2006, 100 (2), 1239-1246; (b) Sawai, D.; Fujii, Y.; Kanamoto, T., Development of oriented morphology and tensile properties upon superdawing of solution-spun fibers of ultrahigh molecular weight poly (acrylonitrile). *Polymer* 2006, 47 (12), 4445-4453; (c) Jarecki, L.; Meier, D. J., Ultrahigh modulus polyethylene. 1 Effect of drawing temperature. *Polymer* 1979, 20 (9), 1078-1082; (d) Jayanarayanan, K.; Jose, T.; Thomas, S.; Joseph, K., Effect of draw ratio on the microstructure, thermal, tensile and dynamic rheological properties of insitu microfibrillar composites. *European Polymer Journal* 2009, 45 (6), 1738-1747.
38. Smith, P.; Lemstra, P. J., Ultra-high-strength polyethylene filaments by solution spinning/drawing. *Journal of Materials Science* 1980, 15 (2), 505-514.
39. Albertson, A. E.; Teulé, F.; Weber, W.; Yarger, J. L.; Lewis, R. V., Effects of different post-spin stretching conditions on the mechanical properties of synthetic spider silk fibers. *Journal of the mechanical behavior of biomedical materials* 2014, 29, 225-234.
40. Nadler, M.; Steiner, A.; Dvir, T.; Szekely, O.; Szekely, P.; Ginsburg, A.; Asor, R.; Resh, R.; Tamburu, C.; Peres, M., Following the structural changes during zinc-induced crystallization of charged membranes using time-resolved solution X-ray scattering. *Soft Matter* 2011, 7 (4), 1512-1523.
41. Huang, T.; Toraya, H.; Blanton, T.; Wu, Y., X-ray powder diffraction analysis of silver behenate, a possible low-angle diffraction standard. *Journal of applied crystallography* 1993, 26 (2), 180-184.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of generating a collagen fiber, the method comprising:
   (a) extruding a solution of collagen into a coagulating solution to generate the collagen fiber; and
   (b) drawing the fiber in said coagulating solution, wherein the rate of said drawing of said fiber is higher than the rate of extruding said solution of collagen into said coagulating solution, wherein the rate of said drawing of said fiber is at least three times higher than the rate of extruding said solution of collagen into said coagulating solution.

2. The method of claim 1, further comprising isolating the collagen fiber following said extruding.

3. The method of claim 2, further comprising drying the collagen fiber following said isolating.

4. The method of claim 1, wherein said extruding is effected concomitantly with said drawing.

5. The method of claim 3, further comprising polymerizing said collagen following said extruding.

6. The method of claim 3, further comprising crosslinking said collagen following said extruding.

7. The method of claim 6, wherein said crosslinking is effected in said coagulating solution.

8. The method of claim 1, wherein said extruding is effected using a spinneret.

9. The method of claim 1, wherein said extruding is effected by passing said collagen solution through an orifice comprising an inner diameter between 10 µm-100 µm.

10. The method of claim 1, wherein said collagen comprises recombinant atelocollagen.

11. The method of claim 1, wherein said collagen is human collagen.

12. The method of claim 1, wherein said collagen is present at a concentration between 20-200 mg/ml in said solution.

13. The method of claim 1, wherein said collagen is present at a concentration between 30-70 mg/ml in said solution.

14. The method of claim 13, wherein said extruding is effected by passing through an orifice comprising an inner diameter of about 30 μm.

15. The method of claim 1, wherein said solution of collagen is an acidic solution.

16. A collagen fiber produced by the method of claim 1.

17. The collagen fiber of claim 16, having a diameter of about 10 μm.

18. The collagen fiber of claim 16, having a tensile stress at break of between 60-200 MPa when wet.

19. The collagen fiber of claim 16, having a Young's modulus of between 500-1200 MPa when wet.

20. The collagen fiber of claim 16, having a strain at break of between 0.15-0.3 when wet.

21. A scaffold comprising the collagen fiber of claim 16.

22. The scaffold of claim 21, further comprising a cell population seeded thereon.

23. A pharmaceutical composition comprising the isolated collgaen fiber of claim 2.

24. A cosmetic composition comprising the isolated collagen fiber of claim 2.

\* \* \* \* \*

SEQUENCE LISTING

<160> NUMBER OF SEQ ID NOS: 14

<210> SEQ ID NO 1
<211> LENGTH: 1464
<212> TYPE: PRT
<213> ORGANISM: Homo sapiens

<400> SEQUENCE: 1

```
Met Phe Ser Phe Val Asp Leu Arg Leu Leu Leu Leu Ala Ala Thr
 1               5                  10                  15

Ala Leu Leu Thr His Gly Gln Glu Gly Gln Val Glu Gly Gln Asp
                20                  25                  30

Glu Asp Ile Pro Pro Ile Thr Cys Val Gln Asn Gly Leu Arg Tyr His
                35                  40                  45

Asp Arg Asp Val Trp Lys Pro Glu Pro Cys Arg Ile Cys Val Cys Asp
 50                  55                  60

Asn Gly Lys Val Leu Cys Asp Asp Val Ile Cys Asp Glu Thr Lys Asn
 65                  70                  75                  80

Cys Pro Gly Ala Glu Val Pro Glu Gly Glu Cys Cys Pro Val Cys Pro
                    85                  90                  95

Asp Gly Ser Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
                115                 120                 125

Pro Gly Arg Asp Gly Ile Pro Gly Gln Pro Gly Leu Pro Gly Pro Pro
                130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
                180                 185                 190

Pro Gly Ala Pro Gly Pro Gln Gly Phe Gln Gly Pro Pro Gly Glu Pro
                195                 200                 205

Gly Glu Pro Gly Ala Ser Gly Pro Met Gly Pro Arg Gly Pro Pro Gly
                210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
                260                 265                 270

Leu Asp Gly Ala Lys Gly Asp Ala Gly Pro Ala Gly Pro Lys Gly Glu
                275                 280                 285

Pro Gly Ser Pro Gly Glu Asn Gly Ala Pro Gly Gln Met Gly Pro Arg
                290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
                340                 345                 350

Gly Glu Ala Gly Pro Gln Gly Pro Arg Gly Ser Glu Gly Pro Gln Gly
                355                 360                 365
```

-continued

```
Val Arg Gly Glu Pro Gly Pro Pro Gly Pro Ala Gly Ala Ala Gly Pro
370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Pro Pro Gly Pro Lys Gly Asn
            420                 425                 430

Ser Gly Glu Pro Gly Ala Pro Gly Ser Lys Gly Asp Thr Gly Ala Lys
            435                 440                 445

Gly Glu Pro Gly Pro Val Gly Val Gln Gly Pro Pro Gly Pro Ala Gly
450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
                500                 505                 510

Ser Pro Gly Pro Ala Gly Pro Lys Gly Ser Pro Gly Glu Ala Gly Arg
            515                 520                 525

Pro Gly Glu Ala Gly Leu Pro Gly Ala Lys Gly Leu Thr Gly Ser Pro
530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
                580                 585                 590

Gly Lys Ala Gly Glu Arg Gly Val Pro Gly Pro Pro Gly Ala Val Gly
            595                 600                 605

Pro Ala Gly Lys Asp Gly Glu Ala Gly Ala Gln Gly Pro Pro Gly Pro
610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655

Lys Pro Gly Glu Gln Gly Val Pro Gly Asp Leu Gly Ala Pro Gly Pro
                660                 665                 670

Ser Gly Ala Arg Gly Glu Arg Gly Phe Pro Gly Glu Arg Gly Val Gln
            675                 680                 685

Gly Pro Pro Gly Pro Ala Gly Pro Arg Gly Ala Asn Gly Ala Pro Gly
690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
                740                 745                 750

Ala Asp Gly Ser Pro Gly Lys Asp Gly Val Arg Gly Leu Thr Gly Pro
            755                 760                 765

Ile Gly Pro Pro Gly Pro Ala Gly Ala Pro Gly Asp Lys Gly Glu Ser
770                 775                 780

Gly Pro Ser Gly Pro Ala Gly Pro Thr Gly Ala Arg Gly Ala Pro Gly
```

```
                785                 790                 795                 800
Asp Arg Gly Glu Pro Gly Pro Gly Pro Ala Gly Phe Ala Gly Pro
                    805                 810                 815

Pro Gly Ala Asp Gly Gln Pro Gly Ala Lys Gly Glu Pro Gly Asp Ala
                820                 825                 830

Gly Ala Lys Gly Asp Ala Gly Pro Pro Gly Pro Ala Gly Pro Ala Gly
                835                 840                 845

Pro Pro Gly Pro Ile Gly Asn Val Gly Ala Pro Gly Ala Lys Gly Ala
        850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
                    885                 890                 895

Pro Pro Gly Pro Ala Gly Lys Glu Gly Gly Lys Gly Pro Arg Gly Glu
            900                 905                 910

Thr Gly Pro Ala Gly Arg Pro Gly Glu Val Gly Pro Pro Gly Pro Pro
                915                 920                 925

Gly Pro Ala Gly Glu Lys Gly Ser Pro Gly Ala Asp Gly Pro Ala Gly
        930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975

Gly Pro Ser Gly Glu Pro Gly Lys Gln Gly Pro Ser Gly Ala Ser Gly
                    980                 985                 990

Glu Arg Gly Pro Pro Gly Pro Met Gly Pro Pro Gly Leu Ala Gly Pro
            995                 1000                1005

Pro Gly Glu Ser Gly Arg Glu Gly Ala Pro Gly Ala Glu Gly Ser
        1010                1015                1020

Pro Gly Arg Asp Gly Ser Pro Gly Ala Lys Gly Asp Arg Gly Glu
        1025                1030                1035

Thr Gly Pro Ala Gly Pro Pro Gly Ala Pro Gly Ala Pro Gly Ala
        1040                1045                1050

Pro Gly Pro Val Gly Pro Ala Gly Lys Ser Gly Asp Arg Gly Glu
        1055                1060                1065

Thr Gly Pro Ala Gly Pro Ala Gly Pro Val Gly Pro Val Gly Ala
        1070                1075                1080

Arg Gly Pro Ala Gly Pro Gln Gly Pro Arg Gly Asp Lys Gly Glu
        1085                1090                1095

Thr Gly Glu Gln Gly Asp Arg Gly Ile Lys Gly His Arg Gly Phe
        1100                1105                1110

Ser Gly Leu Gln Gly Pro Pro Gly Pro Pro Gly Ser Pro Gly Glu
        1115                1120                1125

Gln Gly Pro Ser Gly Ala Ser Gly Pro Ala Gly Pro Arg Gly Pro
        1130                1135                1140

Pro Gly Ser Ala Gly Ala Pro Gly Lys Asp Gly Leu Asn Gly Leu
        1145                1150                1155

Pro Gly Pro Ile Gly Pro Pro Gly Pro Arg Gly Arg Thr Gly Asp
        1160                1165                1170

Ala Gly Pro Val Gly Pro Pro Gly Pro Pro Gly Pro Pro Gly Pro
        1175                1180                1185

Pro Gly Pro Pro Ser Ala Gly Phe Asp Phe Ser Phe Leu Pro Gln
        1190                1195                1200
```

```
Pro Pro Gln Glu Lys Ala His Asp Gly Gly Arg Tyr Tyr Arg Ala
    1205                1210                1215

Asp Asp Ala Asn Val Val Arg Asp Arg Asp Leu Glu Val Asp Thr
    1220                1225                1230

Thr Leu Lys Ser Leu Ser Gln Gln Ile Glu Asn Ile Arg Ser Pro
    1235                1240                1245

Glu Gly Ser Arg Lys Asn Pro Ala Arg Thr Cys Arg Asp Leu Lys
    1250                1255                1260

Met Cys His Ser Asp Trp Lys Ser Gly Glu Tyr Trp Ile Asp Pro
    1265                1270                1275

Asn Gln Gly Cys Asn Leu Asp Ala Ile Lys Val Phe Cys Asn Met
    1280                1285                1290

Glu Thr Gly Glu Thr Cys Val Tyr Pro Thr Gln Pro Ser Val Ala
    1295                1300                1305

Gln Lys Asn Trp Tyr Ile Ser Lys Asn Pro Lys Asp Lys Arg His
    1310                1315                1320

Val Trp Phe Gly Glu Ser Met Thr Asp Gly Phe Gln Phe Glu Tyr
    1325                1330                1335

Gly Gly Gln Gly Ser Asp Pro Ala Asp Val Ala Ile Gln Leu Thr
    1340                1345                1350

Phe Leu Arg Leu Met Ser Thr Glu Ala Ser Gln Asn Ile Thr Tyr
    1355                1360                1365

His Cys Lys Asn Ser Val Ala Tyr Met Asp Gln Thr Gly Asn
    1370                1375                1380

Leu Lys Lys Ala Leu Leu Leu Gln Gly Ser Asn Glu Ile Glu Ile
    1385                1390                1395

Arg Ala Glu Gly Asn Ser Arg Phe Thr Tyr Ser Val Thr Val Asp
    1400                1405                1410

Gly Cys Thr Ser His Thr Gly Ala Trp Gly Lys Thr Val Ile Glu
    1415                1420                1425

Tyr Lys Thr Thr Lys Thr Ser Arg Leu Pro Ile Ile Asp Val Ala
    1430                1435                1440

Pro Leu Asp Val Gly Ala Pro Asp Gln Glu Phe Gly Phe Asp Val
    1445                1450                1455

Gly Pro Val Cys Phe Leu
    1460

<210> SEQ ID NO 2
<211> LENGTH: 1366
<212> TYPE: PRT
<213> ORGANISM: Homo sapiens

<400> SEQUENCE: 2

Met Leu Ser Phe Val Asp Thr Arg Thr Leu Leu Leu Leu Ala Val Thr
1               5                   10                  15

Leu Cys Leu Ala Thr Cys Gln Ser Leu Gln Glu Glu Thr Val Arg Lys
                20                  25                  30

Gly Pro Ala Gly Asp Arg Gly Pro Arg Gly Glu Arg Gly Pro Pro Gly
            35                  40                  45

Pro Pro Gly Arg Asp Gly Glu Asp Gly Pro Thr Gly Pro Pro Gly Pro
        50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
```

-continued

```
                85                  90                  95
Gly Pro Arg Gly Pro Gly Ala Ala Gly Ala Pro Gly Pro Gln Gly
            100                 105                 110
Phe Gln Gly Pro Ala Gly Glu Pro Gly Glu Pro Gly Gln Thr Gly Pro
            115                 120                 125
Ala Gly Ala Arg Gly Pro Ala Gly Pro Pro Gly Lys Ala Gly Glu Asp
            130                 135                 140
Gly His Pro Gly Lys Pro Gly Arg Pro Gly Glu Arg Gly Val Val Gly
145                 150                 155                 160
Pro Gln Gly Ala Arg Gly Phe Pro Gly Thr Pro Gly Leu Pro Gly Phe
                165                 170                 175
Lys Gly Ile Arg Gly His Asn Gly Leu Asp Gly Leu Lys Gly Gln Pro
            180                 185                 190
Gly Ala Pro Gly Val Lys Gly Glu Pro Gly Ala Pro Gly Glu Asn Gly
            195                 200                 205
Thr Pro Gly Gln Thr Gly Ala Arg Gly Leu Pro Gly Glu Arg Gly Arg
            210                 215                 220
Val Gly Ala Pro Gly Pro Ala Gly Ala Arg Gly Ser Asp Gly Ser Val
225                 230                 235                 240
Gly Pro Val Gly Pro Ala Gly Pro Ile Gly Ser Ala Gly Pro Pro Gly
                245                 250                 255
Phe Pro Gly Ala Pro Gly Pro Lys Gly Glu Ile Gly Ala Val Gly Asn
            260                 265                 270
Ala Gly Pro Ala Gly Pro Ala Gly Pro Arg Gly Glu Val Gly Leu Pro
            275                 280                 285
Gly Leu Ser Gly Pro Val Gly Pro Pro Gly Asn Pro Gly Ala Asn Gly
            290                 295                 300
Leu Thr Gly Ala Lys Gly Ala Ala Gly Leu Pro Gly Val Ala Gly Ala
305                 310                 315                 320
Pro Gly Leu Pro Gly Pro Arg Gly Ile Pro Gly Pro Val Gly Ala Ala
                325                 330                 335
Gly Ala Thr Gly Ala Arg Gly Leu Val Gly Glu Pro Gly Pro Ala Gly
            340                 345                 350
Ser Lys Gly Glu Ser Gly Asn Lys Gly Glu Pro Gly Ser Ala Gly Pro
            355                 360                 365
Gln Gly Pro Pro Gly Pro Ser Gly Glu Glu Gly Lys Arg Gly Pro Asn
            370                 375                 380
Gly Glu Ala Gly Ser Ala Gly Pro Pro Gly Pro Pro Gly Leu Arg Gly
385                 390                 395                 400
Ser Pro Gly Ser Arg Gly Leu Pro Gly Ala Asp Gly Arg Ala Gly Val
                405                 410                 415
Met Gly Pro Pro Gly Ser Arg Gly Ala Ser Gly Pro Ala Gly Val Arg
            420                 425                 430
Gly Pro Asn Gly Asp Ala Gly Arg Pro Gly Glu Pro Gly Leu Met Gly
            435                 440                 445
Pro Arg Gly Leu Pro Gly Ser Pro Gly Asn Ile Gly Pro Ala Gly Lys
            450                 455                 460
Glu Gly Pro Val Gly Leu Pro Gly Ile Asp Gly Arg Pro Gly Pro Ile
465                 470                 475                 480
Gly Pro Ala Gly Ala Arg Gly Glu Pro Gly Asn Ile Gly Phe Pro Gly
                485                 490                 495
Pro Lys Gly Pro Thr Gly Asp Pro Gly Lys Asn Gly Asp Lys Gly His
            500                 505                 510
```

```
Ala Gly Leu Ala Gly Ala Arg Gly Ala Pro Gly Pro Asp Gly Asn Asn
        515                 520                 525

Gly Ala Gln Gly Pro Pro Gly Pro Gln Gly Val Gln Gly Gly Lys Gly
        530                 535                 540

Glu Gln Gly Pro Ala Gly Pro Pro Gly Phe Gln Gly Leu Pro Gly Pro
545                 550                 555                 560

Ser Gly Pro Ala Gly Glu Val Gly Lys Pro Gly Glu Arg Gly Leu His
                565                 570                 575

Gly Glu Phe Gly Leu Pro Gly Pro Ala Gly Pro Arg Gly Glu Arg Gly
            580                 585                 590

Pro Pro Gly Glu Ser Gly Ala Ala Gly Pro Thr Gly Pro Ile Gly Ser
        595                 600                 605

Arg Gly Pro Ser Gly Pro Pro Gly Pro Asp Gly Asn Lys Gly Glu Pro
        610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
                645                 650                 655

Lys Gly Glu Pro Gly Leu Arg Gly Glu Ile Gly Asn Pro Gly Arg Asp
            660                 665                 670

Gly Ala Arg Gly Ala Pro Gly Ala Val Gly Ala Pro Gly Pro Ala Gly
        675                 680                 685

Ala Thr Gly Asp Arg Gly Glu Ala Gly Ala Ala Gly Pro Ala Gly Pro
        690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
                725                 730                 735

Ala Lys Gly Glu Arg Gly Ala Lys Gly Pro Lys Gly Glu Asn Gly Val
            740                 745                 750

Val Gly Pro Thr Gly Pro Val Gly Ala Ala Gly Pro Ala Gly Pro Asn
        755                 760                 765

Gly Pro Pro Gly Pro Ala Gly Ser Arg Gly Asp Gly Gly Pro Pro Gly
        770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Ala Gly Lys Glu
                805                 810                 815

Gly Leu Arg Gly Pro Arg Gly Asp Gln Gly Pro Val Gly Arg Thr Gly
            820                 825                 830

Glu Val Gly Ala Val Gly Pro Pro Gly Phe Ala Gly Glu Lys Gly Pro
        835                 840                 845

Ser Gly Glu Ala Gly Thr Ala Gly Pro Pro Gly Thr Pro Gly Pro Gln
850                 855                 860

Gly Leu Leu Gly Ala Pro Gly Ile Leu Gly Leu Pro Gly Ser Arg Gly
865                 870                 875                 880

Glu Arg Gly Leu Pro Gly Val Ala Gly Ala Val Gly Glu Pro Gly Pro
                885                 890                 895

Leu Gly Ile Ala Gly Pro Pro Gly Ala Arg Gly Pro Pro Gly Ala Val
            900                 905                 910

Gly Ser Pro Gly Val Asn Gly Ala Pro Gly Glu Ala Gly Arg Asp Gly
        915                 920                 925
```

```
Asn Pro Gly Asn Asp Gly Pro Pro Gly Arg Asp Gly Gln Pro Gly His
    930                 935                 940
Lys Gly Glu Arg Gly Tyr Pro Gly Asn Ile Gly Pro Val Gly Ala Ala
945                 950                 955                 960
Gly Ala Pro Gly Pro His Gly Pro Val Gly Pro Ala Gly Lys His Gly
                965                 970                 975
Asn Arg Gly Glu Thr Gly Pro Ser Gly Pro Val Gly Pro Ala Gly Ala
                980                 985                 990
Val Gly Pro Arg Gly Pro Ser Gly Pro Gln Gly Ile Arg Gly Asp Lys
            995                 1000                1005
Gly Glu Pro Gly Glu Lys Gly Pro Arg Gly Leu Pro Gly Leu Lys
        1010                1015                1020
Gly His Asn Gly Leu Gln Gly Leu Pro Gly Ile Ala Gly His His
        1025                1030                1035
Gly Asp Gln Gly Ala Pro Gly Ser Val Gly Pro Ala Gly Pro Arg
        1040                1045                1050
Gly Pro Ala Gly Pro Ser Gly Pro Ala Gly Lys Asp Gly Arg Thr
        1055                1060                1065
Gly His Pro Gly Thr Val Gly Pro Ala Gly Ile Arg Gly Pro Gln
        1070                1075                1080
Gly His Gln Gly Pro Ala Gly Pro Pro Gly Pro Pro Gly Pro Pro
        1085                1090                1095
Gly Pro Pro Gly Val Ser Gly Gly Gly Tyr Asp Phe Gly Tyr Asp
        1100                1105                1110
Gly Asp Phe Tyr Arg Ala Asp Gln Pro Arg Ser Ala Pro Ser Leu
        1115                1120                1125
Arg Pro Lys Asp Tyr Glu Val Asp Ala Thr Leu Lys Ser Leu Asn
        1130                1135                1140
Asn Gln Ile Glu Thr Leu Leu Thr Pro Glu Gly Ser Arg Lys Asn
        1145                1150                1155
Pro Ala Arg Thr Cys Arg Asp Leu Arg Leu Ser His Pro Glu Trp
        1160                1165                1170
Ser Ser Gly Tyr Tyr Trp Ile Asp Pro Asn Gln Gly Cys Thr Met
        1175                1180                1185
Asp Ala Ile Lys Val Tyr Cys Asp Phe Ser Thr Gly Glu Thr Cys
        1190                1195                1200
Ile Arg Ala Gln Pro Glu Asn Ile Pro Ala Lys Asn Trp Tyr Arg
        1205                1210                1215
Ser Ser Lys Asp Lys Lys His Val Trp Leu Gly Glu Thr Ile Asn
        1220                1225                1230
Ala Gly Ser Gln Phe Glu Tyr Asn Val Glu Gly Val Thr Ser Lys
        1235                1240                1245
Glu Met Ala Thr Gln Leu Ala Phe Met Arg Leu Leu Ala Asn Tyr
        1250                1255                1260
Ala Ser Gln Asn Ile Thr Tyr His Cys Lys Asn Ser Ile Ala Tyr
        1265                1270                1275
Met Asp Glu Glu Thr Gly Asn Leu Lys Lys Ala Val Ile Leu Gln
        1280                1285                1290
Gly Ser Asn Asp Val Glu Leu Val Ala Glu Gly Asn Ser Arg Phe
        1295                1300                1305
Thr Tyr Thr Val Leu Val Asp Gly Cys Ser Lys Lys Thr Asn Glu
        1310                1315                1320
Trp Gly Lys Thr Ile Ile Glu Tyr Lys Thr Asn Lys Pro Ser Arg
```

-continued

```
            1325                1330                1335

Leu Pro Phe Leu Asp Ile Ala Pro Leu Asp Ile Gly Gly Ala Asp
        1340                1345                1350

Gln Glu Phe Phe Val Asp Ile Gly Pro Val Cys Phe Lys
        1355                1360                1365

<210> SEQ ID NO 3
<211> LENGTH: 1464
<212> TYPE: PRT
<213> ORGANISM: Homo sapiens

<400> SEQUENCE: 3

Met Phe Ser Phe Val Asp Leu Arg Leu Leu Leu Leu Leu Ala Ala Thr
1               5                   10                  15

Ala Leu Leu Thr His Gly Gln Glu Glu Gly Gln Val Glu Gly Gln Asp
            20                  25                  30

Glu Asp Ile Pro Pro Ile Thr Cys Val Gln Asn Gly Leu Arg Tyr His
        35                  40                  45

Asp Arg Asp Val Trp Lys Pro Glu Pro Cys Arg Ile Cys Val Cys Asp
    50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
        115                 120                 125

Pro Gly Arg Asp Gly Ile Pro Gly Gln Pro Gly Leu Pro Gly Pro Pro
    130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
        195                 200                 205

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335
```

-continued

```
Thr Gly Pro Ala Gly Pro Pro Gly Phe Pro Gly Ala Val Gly Ala Lys
            340                 345                 350
Gly Glu Ala Gly Pro Gln Gly Pro Arg Gly Ser Glu Gly Pro Gln Gly
        355                 360                 365
Val Arg Gly Glu Pro Gly Pro Pro Gly Pro Ala Gly Ala Ala Gly Pro
    370                 375                 380
Ala Gly Asn Pro Gly Ala Asp Gly Gln Pro Gly Ala Lys Gly Ala Asn
385                 390                 395                 400
Gly Ala Pro Gly Ile Ala Gly Ala Pro Gly Phe Pro Gly Ala Arg Gly
                405                 410                 415
Pro Ser Gly Pro Gln Gly Pro Gly Gly Pro Pro Gly Pro Lys Gly Asn
            420                 425                 430
Ser Gly Glu Pro Gly Ala Pro Gly Ser Lys Gly Asp Thr Gly Ala Lys
        435                 440                 445
Gly Glu Pro Gly Pro Val Gly Val Gln Gly Pro Pro Gly Pro Ala Gly
    450                 455                 460
Glu Glu Gly Lys Arg Gly Ala Arg Gly Glu Pro Gly Pro Thr Gly Leu
465                 470                 475                 480
Pro Gly Pro Pro Gly Glu Arg Gly Gly Pro Gly Ser Arg Gly Phe Pro
                485                 490                 495
Gly Ala Asp Gly Val Ala Gly Pro Lys Gly Pro Ala Gly Glu Arg Gly
            500                 505                 510
Ser Pro Gly Pro Ala Gly Pro Lys Gly Ser Pro Gly Glu Ala Gly Arg
        515                 520                 525
Pro Gly Glu Ala Gly Leu Pro Gly Ala Lys Gly Leu Thr Gly Ser Pro
    530                 535                 540
Gly Ser Pro Gly Pro Asp Gly Lys Thr Gly Pro Pro Gly Pro Ala Gly
545                 550                 555                 560
Gln Asp Gly Arg Pro Gly Pro Pro Gly Pro Pro Gly Ala Arg Gly Gln
                565                 570                 575
Ala Gly Val Met Gly Phe Pro Gly Pro Lys Gly Ala Ala Gly Glu Pro
            580                 585                 590
Gly Lys Ala Gly Glu Arg Gly Val Pro Gly Pro Pro Gly Ala Val Gly
        595                 600                 605
Pro Ala Gly Lys Asp Gly Glu Ala Gly Ala Gln Gly Pro Pro Gly Pro
    610                 615                 620
Ala Gly Pro Ala Gly Glu Arg Gly Glu Gln Gly Pro Ala Gly Ser Pro
625                 630                 635                 640
Gly Phe Gln Gly Leu Pro Gly Pro Ala Gly Pro Pro Gly Glu Ala Gly
                645                 650                 655
Lys Pro Gly Glu Gln Gly Val Pro Gly Asp Leu Gly Ala Pro Gly Pro
            660                 665                 670
Ser Gly Ala Arg Gly Glu Arg Gly Phe Pro Gly Glu Arg Gly Val Gln
        675                 680                 685
Gly Pro Pro Gly Pro Ala Gly Pro Arg Gly Ala Asn Gly Ala Pro Gly
    690                 695                 700
Asn Asp Gly Ala Lys Gly Asp Ala Gly Ala Pro Gly Ala Pro Gly Ser
705                 710                 715                 720
Gln Gly Ala Pro Gly Leu Gln Gly Met Pro Gly Glu Arg Gly Ala Ala
                725                 730                 735
Gly Leu Pro Gly Pro Lys Gly Asp Arg Gly Asp Ala Gly Pro Lys Gly
            740                 745                 750
Ala Asp Gly Ser Pro Gly Lys Asp Gly Val Arg Gly Leu Thr Gly Pro
```

-continued

```
            755                 760                 765
Ile Gly Pro Pro Gly Pro Ala Gly Ala Pro Gly Asp Lys Gly Glu Ser
            770                 775                 780
Gly Pro Ser Gly Pro Ala Gly Pro Thr Gly Ala Arg Gly Ala Pro Gly
785                 790                 795                 800
Asp Arg Gly Glu Pro Gly Pro Pro Gly Ala Phe Ala Gly Pro
                805                 810                 815
Pro Gly Ala Asp Gly Gln Pro Gly Ala Lys Gly Glu Pro Gly Asp Ala
                820                 825                 830
Gly Ala Lys Gly Asp Ala Gly Pro Pro Gly Pro Ala Gly Pro Ala Gly
                835                 840                 845
Pro Pro Gly Pro Ile Gly Asn Val Gly Ala Pro Gly Ala Lys Gly Ala
850                 855                 860
Arg Gly Ser Ala Gly Pro Pro Gly Ala Thr Gly Phe Pro Gly Ala Ala
865                 870                 875                 880
Gly Arg Val Gly Pro Pro Gly Pro Ser Gly Asn Ala Gly Pro Pro Gly
                885                 890                 895
Pro Pro Gly Pro Ala Gly Lys Glu Gly Gly Lys Gly Pro Arg Gly Glu
                900                 905                 910
Thr Gly Pro Ala Gly Arg Pro Gly Glu Val Gly Pro Pro Gly Pro Pro
                915                 920                 925
Gly Pro Ala Gly Glu Lys Gly Ser Pro Gly Ala Asp Gly Pro Ala Gly
930                 935                 940
Ala Pro Gly Thr Pro Gly Pro Gln Gly Ile Ala Gly Gln Arg Gly Val
945                 950                 955                 960
Val Gly Leu Pro Gly Gln Arg Gly Glu Arg Gly Phe Pro Gly Leu Pro
                965                 970                 975
Gly Pro Ser Gly Glu Pro Gly Lys Gln Gly Pro Ser Gly Ala Ser Gly
                980                 985                 990
Glu Arg Gly Pro Pro Gly Pro Met Gly Pro Pro Gly Leu Ala Gly Pro
                995                 1000                1005
Pro Gly Glu Ser Gly Arg Glu Gly Ala Pro Gly Ala Glu Gly Ser
        1010                1015                1020
Pro Gly Arg Asp Gly Ser Pro Gly Ala Lys Gly Asp Arg Gly Glu
        1025                1030                1035
Thr Gly Pro Ala Gly Pro Pro Gly Ala Pro Gly Ala Pro Gly Ala
        1040                1045                1050
Pro Gly Pro Val Gly Pro Ala Gly Lys Ser Gly Asp Arg Gly Glu
        1055                1060                1065
Thr Gly Pro Ala Gly Pro Ala Gly Pro Val Gly Pro Val Gly Ala
        1070                1075                1080
Arg Gly Pro Ala Gly Pro Gln Gly Pro Arg Gly Asp Lys Gly Glu
        1085                1090                1095
Thr Gly Glu Gln Gly Asp Arg Gly Ile Lys Gly His Arg Gly Phe
        1100                1105                1110
Ser Gly Leu Gln Gly Pro Pro Gly Pro Pro Gly Ser Pro Gly Glu
        1115                1120                1125
Gln Gly Pro Ser Gly Ala Ser Gly Pro Ala Gly Pro Arg Gly Pro
        1130                1135                1140
Pro Gly Ser Ala Gly Ala Pro Gly Lys Asp Gly Leu Asn Gly Leu
        1145                1150                1155
Pro Gly Pro Ile Gly Pro Pro Gly Pro Arg Gly Arg Thr Gly Asp
        1160                1165                1170
```

Ala Gly Pro Val Gly Pro Pro Gly Pro Pro Gly Pro
1175            1180            1185

Pro Gly Pro Pro Ser Ala Gly Phe Asp Phe Ser Phe Leu Pro Gln
    1190            1195            1200

Pro Pro Gln Glu Lys Ala His Asp Gly Gly Arg Tyr Tyr Arg Ala
    1205            1210            1215

Asp Asp Ala Asn Val Val Arg Asp Arg Asp Leu Glu Val Asp Thr
    1220            1225            1230

Thr Leu Lys Ser Leu Ser Gln Gln Ile Glu Asn Ile Arg Ser Pro
    1235            1240            1245

Glu Gly Ser Arg Lys Asn Pro Ala Arg Thr Cys Arg Asp Leu Lys
    1250            1255            1260

Met Cys His Ser Asp Trp Lys Ser Gly Glu Tyr Trp Ile Asp Pro
    1265            1270            1275

Asn Gln Gly Cys Asn Leu Asp Ala Ile Lys Val Phe Cys Asn Met
    1280            1285            1290

Glu Thr Gly Glu Thr Cys Val Tyr Pro Thr Gln Pro Ser Val Ala
    1295            1300            1305

Gln Lys Asn Trp Tyr Ile Ser Lys Asn Pro Lys Asp Lys Arg His
    1310            1315            1320

Val Trp Phe Gly Glu Ser Met Thr Asp Gly Phe Gln Phe Glu Tyr
    1325            1330            1335

Gly Gly Gln Gly Ser Asp Pro Ala Asp Val Ala Ile Gln Leu Thr
    1340            1345            1350

Phe Leu Arg Leu Met Ser Thr Glu Ala Ser Gln Asn Ile Thr Tyr
    1355            1360            1365

His Cys Lys Asn Ser Val Ala Tyr Met Asp Gln Thr Gly Asn
    1370            1375            1380

Leu Lys Lys Ala Leu Leu Leu Gln Gly Ser Asn Glu Ile Glu Ile
    1385            1390            1395

Arg Ala Glu Gly Asn Ser Arg Phe Thr Tyr Ser Val Thr Val Asp
    1400            1405            1410

Gly Cys Thr Ser His Thr Gly Ala Trp Gly Lys Thr Val Ile Glu
    1415            1420            1425

Tyr Lys Thr Thr Lys Thr Ser Arg Leu Pro Ile Ile Asp Val Ala
    1430            1435            1440

Pro Leu Asp Val Gly Ala Pro Asp Gln Glu Phe Gly Phe Asp Val
    1445            1450            1455

Gly Pro Val Cys Phe Leu
    1460

<210> SEQ ID NO 4
<211> LENGTH: 1366
<212> TYPE: PRT
<213> ORGANISM: Homo sapiens

<400> SEQUENCE: 4

Met Leu Ser Phe Val Asp Thr Arg Thr Leu Leu Leu Leu Ala Val Thr
1               5                   10                  15

Leu Cys Leu Ala Thr Cys Gln Ser Leu Gln Glu Glu Thr Val Arg Lys
                20                  25                  30

Gly Pro Ala Gly Asp Arg Gly Pro Arg Gly Glu Arg Gly Pro Pro Gly
            35                  40                  45

Pro Pro Gly Arg Asp Gly Glu Asp Gly Pro Thr Gly Pro Pro Gly Pro

```
                50                  55                  60
Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
                100                 105                 110

Phe Gln Gly Pro Ala Gly Glu Pro Gly Glu Pro Gly Gln Thr Gly Pro
                115                 120                 125

Ala Gly Ala Arg Gly Pro Ala Gly Pro Pro Gly Lys Ala Gly Glu Asp
                130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
                180                 185                 190

Gly Ala Pro Gly Val Lys Gly Glu Pro Gly Ala Pro Gly Glu Asn Gly
                195                 200                 205

Thr Pro Gly Gln Thr Gly Ala Arg Gly Leu Pro Gly Glu Arg Gly Arg
                210                 215                 220

Val Gly Ala Pro Gly Pro Ala Gly Ala Arg Gly Ser Asp Gly Ser Val
225                 230                 235                 240

Gly Pro Val Gly Pro Ala Gly Pro Ile Gly Ser Ala Gly Pro Pro Gly
                245                 250                 255

Phe Pro Gly Ala Pro Gly Pro Lys Gly Glu Ile Gly Ala Val Gly Asn
                260                 265                 270

Ala Gly Pro Ala Gly Pro Ala Gly Pro Arg Gly Glu Val Gly Leu Pro
                275                 280                 285

Gly Leu Ser Gly Pro Val Gly Pro Pro Gly Asn Pro Gly Ala Asn Gly
                290                 295                 300

Leu Thr Gly Ala Lys Gly Ala Ala Gly Leu Pro Gly Val Ala Gly Ala
305                 310                 315                 320

Pro Gly Leu Pro Gly Pro Arg Gly Ile Pro Gly Pro Val Gly Ala Ala
                325                 330                 335

Gly Ala Thr Gly Ala Arg Gly Leu Val Gly Glu Pro Gly Pro Ala Gly
                340                 345                 350

Ser Lys Gly Glu Ser Gly Asn Lys Gly Glu Pro Gly Ser Ala Gly Pro
                355                 360                 365

Gln Gly Pro Pro Gly Pro Ser Gly Glu Glu Gly Lys Arg Gly Pro Asn
                370                 375                 380

Gly Glu Ala Gly Ser Ala Gly Pro Pro Gly Pro Pro Gly Leu Arg Gly
385                 390                 395                 400

Ser Pro Gly Ser Arg Gly Leu Pro Gly Ala Asp Gly Arg Ala Gly Val
                405                 410                 415

Met Gly Pro Pro Gly Ser Arg Gly Ala Ser Gly Pro Ala Gly Val Arg
                420                 425                 430

Gly Pro Asn Gly Asp Ala Gly Arg Pro Gly Glu Pro Gly Leu Met Gly
                435                 440                 445

Pro Arg Gly Leu Pro Gly Ser Pro Gly Asn Ile Gly Pro Ala Gly Lys
                450                 455                 460

Glu Gly Pro Val Gly Leu Pro Gly Ile Asp Gly Arg Pro Gly Pro Ile
465                 470                 475                 480
```

Gly Pro Ala Gly Ala Arg Gly Glu Pro Gly Asn Ile Gly Phe Pro Gly
                485                 490                 495

Pro Lys Gly Pro Thr Gly Asp Pro Gly Lys Asn Gly Asp Lys Gly His
            500                 505                 510

Ala Gly Leu Ala Gly Ala Arg Gly Ala Pro Gly Pro Asp Gly Asn Asn
            515                 520                 525

Gly Ala Gln Gly Pro Pro Gly Pro Gln Gly Val Gln Gly Gly Lys Gly
        530                 535                 540

Glu Gln Gly Pro Ala Gly Pro Pro Gly Phe Gln Gly Leu Pro Gly Pro
545                 550                 555                 560

Ser Gly Pro Ala Gly Glu Val Gly Lys Pro Gly Glu Arg Gly Leu His
            565                 570                 575

Gly Glu Phe Gly Leu Pro Gly Pro Ala Gly Pro Arg Gly Glu Arg Gly
            580                 585                 590

Pro Pro Gly Glu Ser Gly Ala Ala Gly Pro Thr Gly Pro Ile Gly Ser
            595                 600                 605

Arg Gly Pro Ser Gly Pro Pro Gly Pro Asp Gly Asn Lys Gly Glu Pro
            610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
            645                 650                 655

Lys Gly Glu Pro Gly Leu Arg Gly Glu Ile Gly Asn Pro Gly Arg Asp
            660                 665                 670

Gly Ala Arg Gly Ala Pro Gly Ala Val Gly Ala Pro Gly Pro Ala Gly
            675                 680                 685

Ala Thr Gly Asp Arg Gly Glu Ala Gly Ala Ala Gly Pro Ala Gly Pro
            690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
            725                 730                 735

Ala Lys Gly Glu Arg Gly Ala Lys Gly Pro Lys Gly Glu Asn Gly Val
            740                 745                 750

Val Gly Pro Thr Gly Pro Val Gly Ala Ala Gly Pro Ala Gly Pro Asn
            755                 760                 765

Gly Pro Pro Gly Pro Ala Gly Ser Arg Gly Asp Gly Gly Pro Pro Gly
            770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Pro Ala Gly Lys Glu
            805                 810                 815

Gly Leu Arg Gly Pro Arg Gly Asp Gln Gly Pro Val Gly Arg Thr Gly
            820                 825                 830

Glu Val Gly Ala Val Gly Pro Pro Gly Phe Ala Gly Glu Lys Gly Pro
            835                 840                 845

Ser Gly Glu Ala Gly Thr Ala Gly Pro Pro Gly Thr Pro Gly Pro Gln
            850                 855                 860

Gly Leu Leu Gly Ala Pro Gly Ile Leu Gly Leu Pro Gly Ser Arg Gly
865                 870                 875                 880

Glu Arg Gly Leu Pro Gly Val Ala Gly Ala Val Gly Glu Pro Gly Pro
            885                 890                 895

```
Leu Gly Ile Ala Gly Pro Pro Gly Ala Arg Gly Pro Gly Ala Val
            900                 905                 910

Gly Ser Pro Gly Val Asn Gly Ala Pro Gly Glu Ala Gly Arg Asp Gly
        915                 920                 925

Asn Pro Gly Asn Asp Gly Pro Pro Gly Arg Asp Gly Gln Pro Gly His
    930                 935                 940

Lys Gly Glu Arg Gly Tyr Pro Gly Asn Ile Gly Pro Val Gly Ala Ala
945                 950                 955                 960

Gly Ala Pro Gly Pro His Gly Pro Val Gly Pro Ala Gly Lys His Gly
                965                 970                 975

Asn Arg Gly Glu Thr Gly Pro Ser Gly Pro Val Gly Pro Ala Gly Ala
            980                 985                 990

Val Gly Pro Arg Gly Pro Ser Gly Pro Gln Gly Ile Arg Gly Asp Lys
        995                 1000                1005

Gly Glu Pro Gly Glu Lys Gly Pro Arg Gly Leu Pro Gly Leu Lys
    1010                1015                1020

Gly His Asn Gly Leu Gln Gly Leu Pro Gly Ile Ala Gly His His
    1025                1030                1035

Gly Asp Gln Gly Ala Pro Gly Ser Val Gly Pro Ala Gly Pro Arg
    1040                1045                1050

Gly Pro Ala Gly Pro Ser Gly Pro Ala Gly Lys Asp Gly Arg Thr
    1055                1060                1065

Gly His Pro Gly Thr Val Gly Pro Ala Gly Ile Arg Gly Pro Gln
    1070                1075                1080

Gly His Gln Gly Pro Ala Gly Pro Pro Gly Pro Pro Gly Pro Pro
    1085                1090                1095

Gly Pro Pro Gly Val Ser Gly Gly Gly Tyr Asp Phe Gly Tyr Asp
    1100                1105                1110

Gly Asp Phe Tyr Arg Ala Asp Gln Pro Arg Ser Ala Pro Ser Leu
    1115                1120                1125

Arg Pro Lys Asp Tyr Glu Val Asp Ala Thr Leu Lys Ser Leu Asn
    1130                1135                1140

Asn Gln Ile Glu Thr Leu Leu Thr Pro Glu Gly Ser Arg Lys Asn
    1145                1150                1155

Pro Ala Arg Thr Cys Arg Asp Leu Arg Leu Ser His Pro Glu Trp
    1160                1165                1170

Ser Ser Gly Tyr Tyr Trp Ile Asp Pro Asn Gln Gly Cys Thr Met
    1175                1180                1185

Asp Ala Ile Lys Val Tyr Cys Asp Phe Ser Thr Gly Glu Thr Cys
    1190                1195                1200

Ile Arg Ala Gln Pro Glu Asn Ile Pro Ala Lys Asn Trp Tyr Arg
    1205                1210                1215

Ser Ser Lys Asp Lys Lys His Val Trp Leu Gly Glu Thr Ile Asn
    1220                1225                1230

Ala Gly Ser Gln Phe Glu Tyr Asn Val Glu Gly Val Thr Ser Lys
    1235                1240                1245

Glu Met Ala Thr Gln Leu Ala Phe Met Arg Leu Leu Ala Asn Tyr
    1250                1255                1260

Ala Ser Gln Asn Ile Thr Tyr His Cys Lys Asn Ser Ile Ala Tyr
    1265                1270                1275

Met Asp Glu Glu Thr Gly Asn Leu Lys Lys Ala Val Ile Leu Gln
    1280                1285                1290

Gly Ser Asn Asp Val Glu Leu Val Ala Glu Gly Asn Ser Arg Phe
```

```
            1295                1300                1305
Thr Tyr Thr Val Leu Val Asp Gly Cys Ser Lys Lys Thr Asn Glu
        1310                1315                1320

Trp Gly Lys Thr Ile Ile Glu Tyr Lys Thr Asn Lys Pro Ser Arg
        1325                1330                1335

Leu Pro Phe Leu Asp Ile Ala Pro Leu Asp Ile Gly Gly Ala Asp
        1340                1345                1350

Gln Glu Phe Phe Val Asp Ile Gly Pro Val Cys Phe Lys
        1355                1360                1365

<210> SEQ ID NO 5
<211> LENGTH: 1489
<212> TYPE: PRT
<213> ORGANISM: Homo sapiens

<400> SEQUENCE: 5

Met Ala His Ala Arg Val Leu Leu Ala Leu Ala Val Leu Ala Thr
1               5                   10                  15

Ala Ala Val Ala Val Ala Ser Ser Ser Phe Ala Asp Ser Asn Pro
                20                  25                  30

Ile Arg Pro Val Thr Asp Arg Ala Ala Ser Thr Leu Ala Gln Leu Gln
        35                  40                  45

Glu Glu Gly Gln Val Glu Gly Gln Asp Glu Asp Ile Pro Pro Ile Thr
50                  55                  60

Cys Val Gln Asn Gly Leu Arg Tyr His Asp Arg Asp Val Trp Lys Pro
65                  70                  75                  80

Glu Pro Cys Arg Ile Cys Val Cys Asp Asn Gly Lys Val Leu Cys Asp
                85                  90                  95

Asp Val Ile Cys Asp Glu Thr Lys Asn Cys Pro Gly Ala Glu Val Pro
                100                 105                 110

Glu Gly Glu Cys Cys Pro Val Cys Pro Asp Gly Ser Glu Ser Pro Thr
            115                 120                 125

Asp Gln Glu Thr Thr Gly Val Glu Gly Pro Lys Gly Asp Thr Gly Pro
        130                 135                 140

Arg Gly Pro Arg Gly Pro Ala Gly Pro Pro Gly Arg Asp Gly Ile Pro
145                 150                 155                 160

Gly Gln Pro Gly Leu Pro Gly Pro Pro Gly Pro Pro Gly Pro Pro Gly
                165                 170                 175

Pro Pro Gly Leu Gly Gly Asn Phe Ala Pro Gln Leu Ser Tyr Gly Tyr
                180                 185                 190

Asp Glu Lys Ser Thr Gly Gly Ile Ser Val Pro Gly Pro Met Gly Pro
                195                 200                 205

Ser Gly Pro Arg Gly Leu Pro Gly Pro Pro Gly Ala Pro Gly Pro Gln
        210                 215                 220

Gly Phe Gln Gly Pro Pro Gly Glu Pro Gly Glu Pro Gly Ala Ser Gly
225                 230                 235                 240

Pro Met Gly Pro Arg Gly Pro Pro Gly Pro Pro Gly Lys Asn Gly Asp
                245                 250                 255

Asp Gly Glu Ala Gly Lys Pro Gly Arg Pro Gly Glu Arg Gly Pro Pro
                260                 265                 270

Gly Pro Gln Gly Ala Arg Gly Leu Pro Gly Thr Ala Gly Leu Pro Gly
        275                 280                 285

Met Lys Gly His Arg Gly Phe Ser Gly Leu Asp Gly Ala Lys Gly Asp
        290                 295                 300
```

```
Ala Gly Pro Ala Gly Pro Lys Gly Glu Pro Gly Ser Pro Gly Glu Asn
305                 310                 315                 320

Gly Ala Pro Gly Gln Met Gly Pro Arg Gly Leu Pro Gly Glu Arg Gly
            325                 330                 335

Arg Pro Gly Ala Pro Gly Pro Ala Gly Ala Arg Gly Asn Asp Gly Ala
                340                 345                 350

Thr Gly Ala Ala Gly Pro Pro Gly Pro Thr Gly Pro Ala Gly Pro Pro
            355                 360                 365

Gly Phe Pro Gly Ala Val Gly Ala Lys Gly Glu Ala Gly Pro Gln Gly
        370                 375                 380

Pro Arg Gly Ser Glu Gly Pro Gln Gly Val Arg Gly Glu Pro Gly Pro
385                 390                 395                 400

Pro Gly Pro Ala Gly Ala Ala Gly Pro Ala Gly Asn Pro Gly Ala Asp
            405                 410                 415

Gly Gln Pro Gly Ala Lys Gly Ala Asn Gly Ala Pro Gly Ile Ala Gly
            420                 425                 430

Ala Pro Gly Phe Pro Gly Ala Arg Gly Pro Ser Gly Pro Gln Gly Pro
        435                 440                 445

Gly Gly Pro Pro Gly Pro Lys Gly Asn Ser Gly Glu Pro Gly Ala Pro
450                 455                 460

Gly Ser Lys Gly Asp Thr Gly Ala Lys Gly Glu Pro Gly Pro Val Gly
465                 470                 475                 480

Val Gln Gly Pro Pro Gly Pro Ala Gly Glu Glu Gly Lys Arg Gly Ala
            485                 490                 495

Arg Gly Glu Pro Gly Pro Thr Gly Leu Pro Gly Pro Pro Gly Glu Arg
            500                 505                 510

Gly Gly Pro Gly Ser Arg Gly Phe Pro Gly Ala Asp Gly Val Ala Gly
            515                 520                 525

Pro Lys Gly Pro Ala Gly Glu Arg Gly Ser Pro Gly Pro Ala Gly Pro
530                 535                 540

Lys Gly Ser Pro Gly Glu Ala Gly Arg Pro Gly Glu Ala Gly Leu Pro
545                 550                 555                 560

Gly Ala Lys Gly Leu Thr Gly Ser Pro Gly Ser Pro Gly Pro Asp Gly
            565                 570                 575

Lys Thr Gly Pro Pro Gly Pro Ala Gly Gln Asp Gly Arg Pro Gly Pro
            580                 585                 590

Pro Gly Pro Pro Gly Ala Arg Gly Gln Ala Gly Val Met Gly Phe Pro
            595                 600                 605

Gly Pro Lys Gly Ala Ala Gly Glu Pro Gly Lys Ala Gly Glu Arg Gly
        610                 615                 620

Val Pro Gly Pro Pro Gly Ala Val Gly Pro Ala Gly Lys Asp Gly Glu
625                 630                 635                 640

Ala Gly Ala Gln Gly Pro Pro Gly Pro Ala Gly Pro Ala Gly Glu Arg
            645                 650                 655

Gly Glu Gln Gly Pro Ala Gly Ser Pro Gly Phe Gln Gly Leu Pro Gly
            660                 665                 670

Pro Ala Gly Pro Pro Gly Glu Ala Gly Lys Pro Gly Glu Gln Gly Val
        675                 680                 685

Pro Gly Asp Leu Gly Ala Pro Gly Pro Ser Gly Ala Arg Gly Glu Arg
        690                 695                 700

Gly Phe Pro Gly Glu Arg Gly Val Gln Gly Pro Pro Gly Pro Ala Gly
705                 710                 715                 720

Pro Arg Gly Ala Asn Gly Ala Pro Gly Asn Asp Gly Ala Lys Gly Asp
```

```
                725                 730                 735
Ala Gly Ala Pro Gly Ala Pro Gly Ser Gln Gly Ala Pro Gly Leu Gln
            740                 745                 750
Gly Met Pro Gly Glu Arg Gly Ala Ala Gly Leu Pro Gly Pro Lys Gly
            755                 760                 765
Asp Arg Gly Asp Ala Gly Pro Lys Gly Ala Asp Gly Ser Pro Gly Lys
            770                 775                 780
Asp Gly Val Arg Gly Leu Thr Gly Pro Ile Gly Pro Pro Gly Pro Ala
785                 790                 795                 800
Gly Ala Pro Gly Asp Lys Gly Glu Ser Gly Pro Ser Gly Pro Ala Gly
            805                 810                 815
Pro Thr Gly Ala Arg Gly Ala Pro Gly Asp Arg Gly Glu Pro Gly Pro
            820                 825                 830
Pro Gly Pro Ala Gly Phe Ala Gly Pro Pro Gly Ala Asp Gly Gln Pro
            835                 840                 845
Gly Ala Lys Gly Glu Pro Gly Asp Ala Gly Ala Lys Gly Asp Ala Gly
            850                 855                 860
Pro Pro Gly Pro Ala Gly Pro Ala Gly Pro Pro Gly Pro Ile Gly Asn
865                 870                 875                 880
Val Gly Ala Pro Gly Ala Lys Gly Ala Arg Gly Ser Ala Gly Pro Pro
            885                 890                 895
Gly Ala Thr Gly Phe Pro Gly Ala Ala Gly Arg Val Gly Pro Pro Gly
            900                 905                 910
Pro Ser Gly Asn Ala Gly Pro Pro Gly Pro Pro Gly Pro Ala Gly Lys
            915                 920                 925
Glu Gly Gly Lys Gly Pro Arg Gly Glu Thr Gly Pro Ala Gly Arg Pro
930                 935                 940
Gly Glu Val Gly Pro Pro Gly Pro Pro Gly Pro Ala Gly Glu Lys Gly
945                 950                 955                 960
Ser Pro Gly Ala Asp Gly Pro Ala Gly Ala Pro Gly Thr Pro Gly Pro
            965                 970                 975
Gln Gly Ile Ala Gly Gln Arg Gly Val Val Gly Leu Pro Gly Gln Arg
            980                 985                 990
Gly Glu Arg Gly Phe Pro Gly Leu Pro Gly Pro Ser Gly Glu Pro Gly
            995                 1000                1005
Lys Gln Gly Pro Ser Gly Ala Ser Gly Glu Arg Gly Pro Pro Gly
        1010                1015                1020
Pro Met Gly Pro Pro Gly Leu Ala Gly Pro Pro Gly Glu Ser Gly
        1025                1030                1035
Arg Glu Gly Ala Pro Gly Ala Glu Gly Ser Pro Gly Arg Asp Gly
        1040                1045                1050
Ser Pro Gly Ala Lys Gly Asp Arg Gly Glu Thr Gly Pro Ala Gly
        1055                1060                1065
Pro Pro Gly Ala Pro Gly Ala Pro Gly Ala Pro Gly Pro Val Gly
        1070                1075                1080
Pro Ala Gly Lys Ser Gly Asp Arg Gly Glu Thr Gly Pro Ala Gly
        1085                1090                1095
Pro Ala Gly Pro Val Gly Pro Ala Gly Ala Arg Gly Pro Ala Gly
        1100                1105                1110
Pro Gln Gly Pro Arg Gly Asp Lys Gly Glu Thr Gly Glu Gln Gly
        1115                1120                1125
Asp Arg Gly Ile Lys Gly His Arg Gly Phe Ser Gly Leu Gln Gly
        1130                1135                1140
```

-continued

```
Pro Pro Gly Pro Pro Gly Ser Pro Gly Glu Gln Gly Pro Ser Gly
    1145                1150                1155

Ala Ser Gly Pro Ala Gly Pro Arg Gly Pro Pro Gly Ser Ala Gly
    1160                1165                1170

Ala Pro Gly Lys Asp Gly Leu Asn Gly Leu Pro Gly Pro Ile Gly
    1175                1180                1185

Pro Pro Gly Pro Arg Gly Arg Thr Gly Asp Ala Gly Pro Val Gly
    1190                1195                1200

Pro Pro Gly Pro Pro Gly Pro Pro Gly Pro Pro Gly Pro Pro Ser
    1205                1210                1215

Ala Gly Phe Asp Phe Ser Phe Leu Pro Gln Pro Pro Gln Glu Lys
    1220                1225                1230

Ala His Asp Gly Gly Arg Tyr Tyr Arg Ala Asp Asp Ala Asn Val
    1235                1240                1245

Val Arg Asp Arg Asp Leu Glu Val Asp Thr Thr Leu Lys Ser Leu
    1250                1255                1260

Ser Gln Gln Ile Glu Asn Ile Arg Ser Pro Glu Gly Ser Arg Lys
    1265                1270                1275

Asn Pro Ala Arg Thr Cys Arg Asp Leu Lys Met Cys His Ser Asp
    1280                1285                1290

Trp Lys Ser Gly Glu Tyr Trp Ile Asp Pro Asn Gln Gly Cys Asn
    1295                1300                1305

Leu Asp Ala Ile Lys Val Phe Cys Asn Met Glu Thr Gly Glu Thr
    1310                1315                1320

Cys Val Tyr Pro Thr Gln Pro Ser Val Ala Gln Lys Asn Trp Tyr
    1325                1330                1335

Ile Ser Lys Asn Pro Lys Asp Lys Arg His Val Trp Phe Gly Glu
    1340                1345                1350

Ser Met Thr Asp Gly Phe Gln Phe Glu Tyr Gly Gly Gln Gly Ser
    1355                1360                1365

Asp Pro Ala Asp Val Ala Ile Gln Leu Thr Phe Leu Arg Leu Met
    1370                1375                1380

Ser Thr Glu Ala Ser Gln Asn Ile Thr Tyr His Cys Lys Asn Ser
    1385                1390                1395

Val Ala Tyr Met Asp Gln Gln Thr Gly Asn Leu Lys Lys Ala Leu
    1400                1405                1410

Leu Leu Lys Gly Ser Asn Glu Ile Glu Ile Arg Ala Glu Gly Asn
    1415                1420                1425

Ser Arg Phe Thr Tyr Ser Val Thr Val Asp Gly Cys Thr Ser His
    1430                1435                1440

Thr Gly Ala Trp Gly Lys Thr Val Ile Glu Tyr Lys Thr Thr Lys
    1445                1450                1455

Thr Ser Arg Leu Pro Ile Ile Asp Val Ala Pro Leu Asp Val Gly
    1460                1465                1470

Ala Pro Asp Gln Glu Phe Gly Phe Asp Val Gly Pro Val Cys Phe
    1475                1480                1485

Leu
```

```
<210> SEQ ID NO 6
<211> LENGTH: 1389
<212> TYPE: PRT
<213> ORGANISM: Homo sapiens

<400> SEQUENCE: 6
```

```
Met Ala His Ala Arg Val Leu Leu Ala Leu Ala Val Leu Ala Thr
 1               5                  10                 15

Ala Ala Val Ala Val Ala Ser Ser Ser Phe Ala Asp Ser Asn Pro
            20                  25                  30

Ile Arg Pro Val Thr Asp Arg Ala Ala Ser Thr Leu Ala Gln Leu Leu
            35                  40                  45

Gln Glu Glu Thr Val Arg Lys Gly Pro Ala Gly Asp Arg Gly Pro Arg
 50                  55                  60

Gly Glu Arg Gly Pro Pro Gly Pro Pro Gly Arg Asp Gly Glu Asp Gly
 65                  70                  75                  80

Pro Thr Gly Pro Pro Gly Pro Pro Gly Pro Gly Pro Pro Gly Leu
                85                  90                  95

Gly Gly Asn Phe Ala Ala Gln Tyr Asp Gly Lys Gly Val Gly Leu Gly
                100                 105                 110

Pro Gly Pro Met Gly Leu Met Gly Pro Arg Gly Pro Pro Gly Ala Ala
            115                 120                 125

Gly Ala Pro Gly Pro Gln Gly Phe Gln Gly Pro Ala Gly Glu Pro Gly
 130                 135                 140

Glu Pro Gly Gln Thr Gly Pro Ala Gly Ala Arg Gly Pro Ala Gly Pro
145                 150                 155                 160

Pro Gly Lys Ala Gly Glu Asp Gly His Pro Gly Lys Pro Gly Arg Pro
            165                 170                 175

Gly Glu Arg Gly Val Val Gly Pro Gln Gly Ala Arg Gly Phe Pro Gly
            180                 185                 190

Thr Pro Gly Leu Pro Gly Phe Lys Gly Ile Arg Gly His Asn Gly Leu
            195                 200                 205

Asp Gly Leu Lys Gly Gln Pro Gly Ala Pro Gly Val Lys Gly Glu Pro
 210                 215                 220

Gly Ala Pro Gly Glu Asn Gly Thr Pro Gly Gln Thr Gly Ala Arg Gly
225                 230                 235                 240

Leu Pro Gly Glu Arg Gly Arg Val Gly Ala Pro Gly Pro Ala Gly Ala
            245                 250                 255

Arg Gly Ser Asp Gly Ser Val Gly Pro Val Gly Pro Ala Gly Pro Ile
            260                 265                 270

Gly Ser Ala Gly Pro Pro Gly Phe Pro Gly Ala Pro Gly Pro Lys Gly
            275                 280                 285

Glu Ile Gly Ala Val Gly Asn Ala Gly Pro Thr Gly Pro Ala Gly Pro
 290                 295                 300

Arg Gly Glu Val Gly Leu Pro Gly Leu Ser Gly Pro Val Gly Pro Pro
305                 310                 315                 320

Gly Asn Pro Gly Ala Asn Gly Leu Thr Gly Ala Lys Gly Ala Ala Gly
            325                 330                 335

Leu Pro Gly Val Ala Gly Ala Pro Gly Leu Pro Gly Pro Arg Gly Ile
            340                 345                 350

Pro Gly Pro Val Gly Ala Ala Gly Ala Thr Gly Ala Arg Gly Leu Val
            355                 360                 365

Gly Glu Pro Gly Pro Ala Gly Ser Lys Gly Glu Ser Gly Asn Lys Gly
            370                 375                 380

Glu Pro Gly Ser Ala Gly Pro Gln Gly Pro Pro Gly Pro Ser Gly Glu
385                 390                 395                 400

Glu Gly Lys Arg Gly Pro Asn Gly Glu Ala Gly Ser Ala Gly Pro Pro
            405                 410                 415
```

```
Gly Pro Pro Gly Leu Arg Gly Ser Pro Gly Ser Arg Gly Leu Pro Gly
            420                 425                 430

Ala Asp Gly Arg Ala Gly Val Met Gly Pro Pro Gly Ser Arg Gly Ala
435                 440                 445

Ser Gly Pro Ala Gly Val Arg Gly Pro Asn Gly Asp Ala Gly Arg Pro
    450                 455                 460

Gly Glu Pro Gly Leu Met Gly Pro Arg Gly Leu Pro Gly Ser Pro Gly
465                 470                 475                 480

Asn Ile Gly Pro Ala Gly Lys Glu Gly Pro Val Gly Leu Pro Gly Ile
                485                 490                 495

Asp Gly Arg Pro Gly Pro Ile Gly Pro Ala Gly Ala Arg Gly Glu Pro
            500                 505                 510

Gly Asn Ile Gly Phe Pro Gly Pro Lys Gly Pro Thr Gly Asp Pro Gly
        515                 520                 525

Lys Asn Gly Asp Lys Gly His Ala Gly Leu Ala Gly Ala Arg Gly Ala
    530                 535                 540

Pro Gly Pro Asp Gly Asn Asn Gly Ala Gln Gly Pro Pro Gly Pro Gln
545                 550                 555                 560

Gly Val Gln Gly Gly Lys Gly Glu Gln Gly Pro Ala Gly Pro Pro Gly
                565                 570                 575

Phe Gln Gly Leu Pro Gly Pro Ser Gly Pro Ala Gly Glu Val Gly Lys
            580                 585                 590

Pro Gly Glu Arg Gly Leu His Gly Glu Phe Gly Leu Pro Gly Pro Ala
        595                 600                 605

Gly Pro Arg Gly Glu Arg Gly Pro Pro Gly Glu Ser Gly Ala Ala Gly
    610                 615                 620

Pro Thr Gly Pro Ile Gly Ser Arg Gly Pro Ser Gly Pro Pro Gly Pro
625                 630                 635                 640

Asp Gly Asn Lys Gly Glu Pro Gly Val Val Gly Ala Val Gly Thr Ala
                645                 650                 655

Gly Pro Ser Gly Pro Ser Gly Leu Pro Gly Glu Arg Gly Ala Ala Gly
            660                 665                 670

Ile Pro Gly Gly Lys Gly Glu Lys Gly Glu Pro Gly Leu Arg Gly Glu
        675                 680                 685

Ile Gly Asn Pro Gly Arg Asp Gly Ala Arg Gly Ala His Gly Ala Val
    690                 695                 700

Gly Ala Pro Gly Pro Ala Gly Ala Thr Gly Asp Arg Gly Glu Ala Gly
705                 710                 715                 720

Ala Ala Gly Pro Ala Gly Pro Ala Gly Pro Arg Gly Ser Pro Gly Glu
                725                 730                 735

Arg Gly Glu Val Gly Pro Ala Gly Pro Asn Gly Phe Ala Gly Pro Ala
            740                 745                 750

Gly Ala Ala Gly Gln Pro Gly Ala Lys Gly Glu Arg Gly Gly Lys Gly
        755                 760                 765

Pro Lys Gly Glu Asn Gly Val Val Gly Pro Thr Gly Pro Val Gly Ala
    770                 775                 780

Ala Gly Pro Ala Gly Pro Asn Gly Pro Pro Gly Pro Ala Gly Ser Arg
785                 790                 795                 800

Gly Asp Gly Gly Pro Pro Gly Met Thr Gly Phe Pro Gly Ala Ala Gly
                805                 810                 815

Arg Thr Gly Pro Pro Gly Pro Ser Gly Ile Ser Gly Pro Pro Gly Pro
            820                 825                 830

Pro Gly Pro Ala Gly Lys Glu Gly Leu Arg Gly Pro Arg Gly Asp Gln
```

-continued

```
              835                 840                 845
Gly Pro Val Gly Arg Thr Gly Glu Val Gly Ala Val Gly Pro Pro Gly
              850                 855                 860
Phe Ala Gly Glu Lys Gly Pro Ser Gly Glu Ala Gly Thr Ala Gly Pro
865                 870                 875                 880
Pro Gly Thr Pro Gly Pro Gln Gly Leu Leu Gly Ala Pro Gly Ile Leu
                    885                 890                 895
Gly Leu Pro Gly Ser Arg Gly Glu Arg Gly Leu Pro Gly Val Ala Gly
                    900                 905                 910
Ala Val Gly Glu Pro Gly Pro Leu Gly Ile Ala Gly Pro Pro Gly Ala
                    915                 920                 925
Arg Gly Pro Pro Gly Ala Val Gly Ser Pro Gly Val Asn Gly Ala Pro
930                 935                 940
Gly Glu Ala Gly Arg Asp Gly Asn Pro Gly Asn Asp Gly Pro Pro Gly
945                 950                 955                 960
Arg Asp Gly Gln Pro Gly His Lys Gly Glu Arg Gly Tyr Pro Gly Asn
                    965                 970                 975
Ile Gly Pro Val Gly Ala Ala Gly Ala Pro Gly Pro His Gly Pro Val
                    980                 985                 990
Gly Pro Ala Gly Lys His Gly Asn Arg Gly Glu Thr Gly Pro Ser Gly
                    995                 1000                1005
Pro Val Gly Pro Ala Gly Ala Val Gly Pro Arg Gly Pro Ser Gly
      1010                1015                1020
Pro Gln Gly Ile Arg Gly Asp Lys Gly Glu Pro Gly Glu Lys Gly
      1025                1030                1035
Pro Arg Gly Leu Pro Gly Phe Lys Gly His Asn Gly Leu Gln Gly
      1040                1045                1050
Leu Pro Gly Ile Ala Gly His His Gly Asp Gln Gly Ala Pro Gly
      1055                1060                1065
Ser Val Gly Pro Ala Gly Pro Arg Gly Pro Ala Gly Pro Ser Gly
      1070                1075                1080
Pro Ala Gly Lys Asp Gly Arg Thr Gly His Pro Gly Thr Val Gly
      1085                1090                1095
Pro Ala Gly Ile Arg Gly Pro Gln Gly His Gln Gly Pro Ala Gly
      1100                1105                1110
Pro Pro Gly Pro Pro Gly Pro Pro Gly Pro Pro Gly Val Ser Gly
      1115                1120                1125
Gly Gly Tyr Asp Phe Gly Tyr Asp Gly Asp Phe Tyr Arg Ala Asp
      1130                1135                1140
Gln Pro Arg Ser Ala Pro Ser Leu Arg Pro Lys Asp Tyr Glu Val
      1145                1150                1155
Asp Ala Thr Leu Lys Ser Leu Asn Asn Gln Ile Glu Thr Leu Leu
      1160                1165                1170
Thr Pro Glu Gly Ser Arg Lys Asn Pro Ala Arg Thr Cys Arg Asp
      1175                1180                1185
Leu Arg Leu Ser His Pro Glu Trp Ser Ser Gly Tyr Tyr Trp Ile
      1190                1195                1200
Asp Pro Asn Gln Gly Cys Thr Met Glu Ala Ile Lys Val Tyr Cys
      1205                1210                1215
Asp Phe Pro Thr Gly Glu Thr Cys Ile Arg Ala Gln Pro Glu Asn
      1220                1225                1230
Ile Pro Ala Lys Asn Trp Tyr Arg Ser Ser Lys Asp Lys Lys His
      1235                1240                1245
```

Val Trp Leu Gly Glu Thr Ile Asn Ala Gly Ser Gln Phe Glu Tyr
    1250                1255                1260

Asn Val Glu Gly Val Thr Ser Lys Glu Met Ala Thr Gln Leu Ala
1265                1270                1275

Phe Met Arg Leu Leu Ala Asn Tyr Ala Ser Gln Asn Ile Thr Tyr
    1280                1285                1290

His Cys Lys Asn Ser Ile Ala Tyr Met Asp Glu Thr Gly Asn
    1295                1300                1305

Leu Lys Lys Ala Val Ile Leu Gln Gly Ser Asn Asp Val Glu Leu
    1310                1315                1320

Val Ala Glu Gly Asn Ser Arg Phe Thr Tyr Thr Val Leu Val Asp
    1325                1330                1335

Gly Cys Ser Lys Lys Thr Asn Glu Trp Gly Lys Thr Ile Ile Glu
    1340                1345                1350

Tyr Lys Thr Asn Lys Pro Ser Arg Leu Pro Phe Leu Asp Ile Ala
    1355                1360                1365

Pro Leu Asp Ile Gly Gly Ala Asp His Glu Phe Phe Val Asp Ile
    1370                1375                1380

Gly Pro Val Cys Phe Lys
    1385

<210> SEQ ID NO 7
<211> LENGTH: 5927
<212> TYPE: DNA
<213> ORGANISM: Homo sapiens

<400> SEQUENCE: 7

```
tcgtcggagc agacgggagt ttctcctcgg ggtcggagca ggaggcacgc ggagtgtgag      60
gccacgcatg agcggacgct aaccccctcc ccagccacaa agagtctaca tgtctagggt     120
ctagacatgt tcagctttgt ggacctccgg ctcctgctcc tcttagcggc caccgccctc     180
ctgacgcacg gccaagagga aggccaagtc gagggccaag acgaagacat cccaccaatc     240
acctgcgtac agaacggcct caggtaccat gaccgagacg tgtggaaacc cgagccctgc     300
cggatctgcg tctgcgacaa cggcaaggtg ttgtgcgatg acgtgatctg tgacgagacc     360
aagaactgcc ccggcgccga agtccccgag ggcgagtgct gtcccgtctg ccccgacggc     420
tcagagtcac ccaccgacca agaaaccacc ggcgtcgagg acccaaggg agacactggc     480
ccccgaggcc aaggggacc cgcaggcccc cctggccgag atggcatccc tggacagcct     540
ggacttcccg accccccgg accccccgga cctcccggac ccctggcct cggaggaaac     600
tttgctcccc agctgtctta tggctatgat gagaaatcaa ccggaggaat ttccgtgcct     660
ggccccatgg gtccctctgg tcctcgtggt ctccctggcc ccctggtgc acctggtccc     720
caaggcttcc aaggtccccc tggtgagcct ggcgagcctg gagcttcagg tcccatgggt     780
ccccgaggtc cccaggtcc ccctggaaag aatgagatg atgggaagc tggaaaacct     840
ggtcgtcctg gtgagcgtgg gcctcctggg cctcagggtg ctcgaggatt gcccggaaca     900
gctggcctcc ctggaatgaa gggacacaga ggtttcagtg gtttggatgg tgccaaggga     960
gatgctggtc ctgctggtcc taagggtgag cctggcagcc tggtgaaaa tggagctcct    1020
ggtcagatgg gccccgtgg cctgcctggt gagagaggtc gccctggagc cctggccct    1080
gctggtgctc gtgaaatga tgctgctact ggtgctgccg gccccctgg tcccaccggc    1140
cccgctggtc ctcctggctt ccctggtgct gttggtgcta aggtgaagc tggtccccaa    1200
```

```
gggccccgag gctctgaagg tccccagggt gtgcgtggtg agcctggccc ccctggccct    1260
gctggtgctg ctggccctgc tggaaaccct ggtgctgatg gacagcctgg tgctaaaggt    1320
gccaatggtg ctcctggtat tgctggtgct cctggcttcc ctggtgcccg aggcccctct    1380
ggaccccagg gccccggcgg ccctcctggt cccaagggta acagcggtga acctggtgct    1440
cctggcagca aaggagacac tggtgctaag ggagagcctg gccctgttgg tgttcaagga    1500
ccccctggcc ctgctggaga ggaaggaaag cgaggagctc gaggtgaacc cggacccact    1560
ggcctgcccg acccctgg cgagcgtggt ggacctggta gccgtggttt ccctggcgca    1620
gatggtgttg ctggtcccaa gggtcccgct ggtgaacgtg gttctcctgg ccctgctggc    1680
cccaaaggat ctcctggtga agctggtcgt cccggtgaag ctggtctgcc tggtgccaag    1740
ggtctgactg gaagccctgg cagccctggt cctgatggca aaactggccc ccctggtccc    1800
gccggtcaag atggtcgccc cggaccccca ggcccacctg gtcccgtgg tcaggctggt    1860
gtgatgggat tccctggacc taaaggtgct gctggagagc ccggcaaggc tggagagcga    1920
ggtgttcccg accccctgg cgctgtcggt cctgctggca aagatggaga ggctggagct    1980
cagggacccc ctggccctgc tggtcccgct ggcgagagag gtgaacaagg ccctgctggc    2040
tcccccggat tccagggtct ccctggtcct gctggtcctc caggtgaagc aggcaaacct    2100
ggtgaacagg gtgttcctgg agaccttggc gccctggcc cctctggagc aagaggcgag    2160
agaggtttcc ctggcgagcg tggtgtgcaa ggtccccctg gtcctgctgg tccccgaggg    2220
gccaacggtg ctcccggcaa cgatggtgct aagggtgatg ctggtgcccc tggagctccc    2280
ggtagccagg gcgcccctgg ccttcaggga atgcctggtg aacgtggtgc agctggtctt    2340
ccagggccta aggtgacag aggtgatgct ggtcccaaag gtgctgatgg ctctcctggc    2400
aaagatggcg tccgtggtct gactggcccc attggtcctc ctggccctgc tggtgccct    2460
ggtgacaagg gtgaaagtgg tcccagcggc cctgctggtc ccactggagc tcgtggtgcc    2520
cccgagacc gtggtgagcc tggtcccccc ggccctgctg gctttgctgg ccccctggt    2580
gctgacggcc aacctggtgc taaaggcgaa cctggtgatg ctggtgctaa aggcgatgct    2640
ggtcccctg ccctgccgg acccgctgga ccccctggcc ccattggtaa tgttggtgct    2700
cctggagcca aggtgctcg cggcagcgct ggtccccctg gtgctactgg ttcctggt    2760
gctgctggcc gagtcggtcc tcctggcccc tctggaaatg ctggaccccc tggccctct    2820
ggtcctgctg gcaaagaagg cggcaaaggt ccccgtggtg agactggccc tgctggacgt    2880
cctggtgaag ttggtcccc tggtcccct ggccctgctg gcgagaaagg atccctggt    2940
gctgatggtc ctgctggtgc tcctggtact cccgggcctc aaggtattgc tggacagcgt    3000
ggtgtggtcg gcctgcctgg tcagagagga gagagaggct tccctggtct tcctggcccc    3060
tctggtgaac ctggcaaaca aggtcccctct ggagcaagtg gtgaacgtgg tccccctggt    3120
cccatgggcc ccctggatt ggctggaccc cctggtgaat ctggacgtga gggggctcct    3180
ggtgccgaag gttcccctgg acgagacggt tctcctggcg ccaagggtga ccgtggtgag    3240
accggccccg ctggaccccc tggtgctcct ggtgctcctg gtgcccctgg cccgttggc    3300
cctgctggca agagtggtga tcgtggtgag actggtcctg ctggtcccgc cggtcctgtc    3360
ggccctgttg gcgcccgtgg ccccgccgga cccaaggcc ccgtggtga aagggtgag    3420
acaggcgaac agggcgacag aggcataaag ggtcaccgtg gcttctctgg cctccagggt    3480
ccccctggcc ctcctggctc tcctggtgaa caaggtccct ctggagcctc tggtcctgct    3540
ggtccccgag gtcccccctgg ctctgctggt gctcctggca aagatggact caacggtctc    3600
```

```
cctggcccca ttgggccccc tggtcctcgc ggtcgcactg gtgatgctgg tcctgttggt    3660
ccccccggcc ctcctggacc tcctggtccc cctggtcctc ccagcgctgg tttcgacttc    3720
agcttcctgc cccagccacc tcaagagaag gctcacgatg gtggccgcta ctaccgggct    3780
gatgatgcca atgtggttcg tgaccgtgac ctcgaggtgg acaccaccct caagagcctg    3840
agccagcaga tcgagaacat ccggagccca gagggcagcc gcaagaaccc cgcccgcacc    3900
tgccgtgacc tcaagatgtg ccactctgac tggaagagtg gagagtactg gattgacccc    3960
aaccaaggct gcaacctgga tgccatcaaa gtcttctgca acatggagac tggtgagacc    4020
tgcgtgtacc ccactcagcc cagtgtggcc cagaagaact ggtacatcag caagaacccc    4080
aaggacaaga ggcatgtctg gttcggcgag agcatgaccg atggattcca gttcgagtat    4140
ggcggccagg gctccgaccc tgccgatgtg gccatccagc tgaccttcct gcgcctgatg    4200
tccaccgagg cctcccagaa catcacctac cactgcaaga acagcgtggc ctacatggac    4260
cagcagactg gcaacctcaa gaaggccctg ctcctccagg gctccaacga gatcgagatc    4320
cgcgccgagg gcaacagccg cttcacctac agcgtcactg tcgatggctg cacgagtcac    4380
accggagcct ggggcaagac agtgattgaa tacaaaacca ccaagacctc ccgcctgccc    4440
atcatcgatg tggccccctt ggacgttggt gccccagacc aggaattcgg cttcgacgtt    4500
ggccctgtct gcttcctgta aactccctcc atcccaacct ggctccctcc cacccaacca    4560
actttccccc caacccggaa acagacaagc aacccaaact gaaccccctc aaaagccaaa    4620
aaatgggaga caatttcaca tggactttgg aaaatatttt tttcctttgc attcatctct    4680
caaacttagt ttttatcttt gaccaaccga acatgaccaa aaaccaaaag tgcattcaac    4740
cttaccaaaa aaaaaaaaaa aaaagaata aataaataac tttttaaaaa aggaagcttg    4800
gtccacttgc ttgaagaccc atgcggggt aagtccctt ctgcccgttg ggcttatgaa    4860
accccaatgc tgccctttct gctcctttct ccacaccccc cttggggcct ccctccact    4920 ccttcccaaa tctgtctccc cagaagacac aggaaacaat gtattgtctg cccagcaatc    4980
aaaggcaatg ctcaaacacc caagtggccc ccaccctcag cccgctcctg cccgcccagc    5040 accccccaggc cctggggggac ctggggttct cagactgcca aagaagcctt gccatctggc    5100
gctcccatgg ctcttgcaac atctcccctt cgttttgag ggggtcatgc cggggagcc    5160 accagcccct cactgggttc ggaggagagt caggaagggc cacgacaaag cagaaacatc    5220
ggatttgggg aacgcgtgtc aatcccttgt gccgcagggc tgggcgggag agactgttct    5280
gttccttgtg taactgtgtt gctgaaagac tacctcgttc ttgtcttgat gtgtcaccgg    5340
ggcaactgcc tggggcggg gatggggca gggtggaagc ggctccccat tttataccaa    5400
aggtgctaca tctatgtgat gggtggggtg gggagggaat cactggtgct atagaaattg    5460
agatgccccc ccaggccagc aaatgttcct tttgttcaa agtctatttt tattccttga    5520 tattttctt ttttttttt tttttttgtg gatgggggact tgtgaatttt tctaaaggtg    5580
ctatttaaca tgggaggaga gcgtgtgcgg ctccagccca gcccgctgct cactttccac    5640
cctctctcca cctgcctctg gcttctcagg cctctgctct ccgacctctc tcctctgaaa    5700
ccctcctcca cagctgcagc ccatcctccc ggctccctcc tagtctgtcc tgcgtcctct    5760
gtccccgggt ttcagagaca acttcccaaa gcacaaagca gtttttcccc ctaggggtgg    5820
gaggaagcaa aagactctgt acctattttg tatgtgtata ataatttgag atgttttaa    5880 ttattttgat tgctggaata aagcatgtgg aaatgaccca aacataa              5927
```

<210> SEQ ID NO 8
<211> LENGTH: 5411
<212> TYPE: DNA
<213> ORGANISM: Homo sapiens

<400> SEQUENCE: 8

| | | | | | |
|---|---|---|---|---|---|
| gtgtcccata | gtgtttccaa | acttggaaag | gcgggggag | ggcgggagga | tgcggagggc | 60 |
| ggaggtatgc | agacaacgag | tcagagtttc | cccttgaaag | cctcaaaagt | gtccacgtcc | 120 |
| tcaaaagaa | tggaaccaat | ttaagaagcc | agccccgtgg | ccacgtccct | tcccccattc | 180 |
| gctccctcct | ctgcgcccc | gcaggctcct | cccagctgtg | gctgcccggg | ccccagccc | 240 |
| cagccctccc | attggtggag | gccctttggg | aggcacccta | gggccaggga | aacttttgcc | 300 |
| gtataaatag | ggcagatccg | ggctttatta | ttttagcacc | acggcagcag | gaggtttcgg | 360 |
| ctaagttgga | ggtactggcc | acgactgcat | gcccgcgccc | gccaggtgat | acctccgccg | 420 |
| gtgacccagg | ggctctgcga | cacaaggagt | ctgcatgtct | aagtgctaga | catgctcagc | 480 |
| tttgtggata | cgcggacttt | gttgctgctt | gcagtaacct | tatgcctagc | aacatgccaa | 540 |
| tcttttacaag | aggaaactgt | aagaaagggc | ccagccggag | atagaggacc | acgtggagaa | 600 |
| aggggtccac | caggccccc | aggcagagat | ggtgaagatg | gtcccacagg | ccctcctggt | 660 |
| ccacctggtc | ctcctggccc | cctggtctc | ggtgggaact | tgctgctca | gtatgatgga | 720 |
| aaaggagttg | gacttggccc | tggaccaatg | ggcttaatgg | gacctagagg | cccacctggt | 780 |
| gcagctggag | ccccaggccc | tcaaggtttc | caaggacctg | ctggtgagcc | tggtgaacct | 840 |
| ggtcaaactg | gtcctgcagg | tgctcgtggt | ccagctggcc | ctcctggcaa | ggctggtgaa | 900 |
| gatggtcacc | ctggaaaacc | cggacgacct | ggtgagagag | gagttgttgg | accacagggt | 960 |
| gctcgtggtt | tccctggaac | tcctggactt | cctggcttca | aaggcattag | gggacacaat | 1020 |
| ggtctggatg | gattgaaggg | acagcccggt | gctcctggtg | tgaagggtga | acctggtgcc | 1080 |
| cctggtgaaa | atggaactcc | aggtcaaaca | ggagcccgtg | ggcttcctgg | tgagagagga | 1140 |
| cgtgttggtg | ccctggcc | agctggtgcc | cgtggcagtg | atggaagtgt | gggtcccgtg | 1200 |
| ggtcctgctg | gtcccattgg | gtctgctggc | cctccaggct | tcccaggtgc | ccctggcccc | 1260 |
| aagggtgaaa | ttggagctgt | tggtaacgct | ggtcctgctg | gtcccgccgg | tccccgtggt | 1320 |
| gaagtgggtc | ttccaggcct | ctccggcccc | gttggacctc | ctggtaatcc | tggagcaaac | 1380 |
| ggccttactg | gtgccaaggg | tgctgctggc | cttcccggcg | ttgctgggc | tcccggcctc | 1440 |
| cctggacccc | gcggtattcc | tggccctgtt | ggtgctgccg | gtgctactgg | tgccagagga | 1500 |
| cttgttggtg | agcctggtcc | agctggctcc | aaaggagaga | gcggtaacaa | gggtgagccc | 1560 |
| ggctctgctg | ggccccaagg | tcctcctggt | cccagtggtg | aagaaggaaa | gagaggccct | 1620 |
| aatggggaag | ctggatctgc | cggccctcca | ggacctcctg | ggctgagagg | tagtcctggt | 1680 |
| tctcgtggtc | ttcctggagc | tgatggcaga | gctggcgtca | tgggccctcc | tggtagtcgt | 1740 |
| ggtgcaagtg | gccctgctgg | agtccgagga | cctaatggaa | atgctggtcg | ccctggggag | 1800 |
| cctggtctca | tgggacccag | aggtcttcct | ggttcccctg | gaaatatcgg | ccccgctgga | 1860 |
| aaagaaggtc | ctgtcggcct | ccctggcatc | gacggcaggc | ctggcccaat | tggcccagct | 1920 |
| ggagcaagag | gagagcctgg | caacattgga | ttccctggac | ccaaaggccc | cactggtgat | 1980 |
| cctggcaaaa | acggtgataa | aggtcatgct | ggtcttgctg | gtgctcgggg | tgctccaggt | 2040 |
| cctgatggaa | acaatggtgc | tcagggacct | cctggaccac | agggtgttca | aggtggaaaa | 2100 |
| ggtgaacagg | gtccccctgg | tcctccaggc | ttccagggtc | tgcctggccc | ctcaggtccc | 2160 |

```
gctggtgaag ttggcaaacc aggagaaagg ggtctccatg gtgagtttgg tctccctggt   2220
cctgctggtc aagaggggga acgcggtccc ccaggtgaga gtggtgctgc cggtcctact   2280
ggtcctattg gaagccgagg tccttctgga cccccagggc ctgatggaaa caagggtgaa   2340
cctggtgtgg ttggtgctgt gggcactgct ggtccatctg gtcctagtgg actcccagga   2400
gagaggggtg ctgctggcat acctggaggc aagggagaaa aggtgaacc tggtctcaga    2460 ggtgaaattg gtaaccctgg cagagatggt gctcgtggtg ctcctggtgc tgtaggtgcc   2520
cctggtcctg ctggagccac aggtgaccgg ggcgaagctg gggctgctgg tcctgctggt   2580
cctgctggtc ctcggggaag ccctggtgaa cgtggtgagg tcggtcctgc tggccccaat   2640
ggatttgctg gtcctgctgg tgctgctggt caacctggtg ctaaaggaga agaggagcc   2700 aaagggccta agggtgaaaa cggtgttgtt ggtcccacag gccccgttgg agctgctggc   2760
ccagctggtc caaatggtcc cccggtcct gctggaagtc gtggtgatgg aggccccct    2820 ggtatgactg gtttccctgg tgctgctgga cggactggtc ccccaggacc ctctggtatt   2880 tctggcccctc ctggtcccccc tggtcctgct gggaagaag gcttcgtgg tcctcgtggt   2940 gaccaaggtc cagttggccg aactggagaa gtaggtgcag ttggtccccc tggcttcgct   3000
ggtgagaagg gtccctctgg agaggctggt actgctggac ctcctggcac tccaggtcct   3060
cagggtcttc ttggtgctcc tggtattctg ggtctccctg gctcgagagg tgaacgtggt   3120
ctaccaggtg ttgctggtgc tgtgggtgaa cctggtcctc ttggcattgc cggccctcct   3180
ggggcccgtg gtcctcctgg tgctgtgggt agtcctggag tcaacggtgc tcctggtgaa   3240
gctggtcgtg atggcaaccc tgggaacgat ggtcccccag gtcgcgatgg tcaacccgga   3300
cacaagggag agcgcggtta ccctggcaat attggtcccg ttggtgctgc aggtgcacct   3360
ggtcctcatg gccccgtggg tcctgctggc aaacatggaa accgtggtga aactggtcct   3420
tctggtcctg ttggtcctgc tggtgctgtt ggcccaagag gtcctagtgg cccacaaggc   3480
attcgtggcg ataagggaga gcccggtgaa aaggggccca gaggtcttcc tggcttaaag   3540
ggacacaatg gattgcaagg tctgcctggt atcgctggtc accatggtga tcaaggtgct   3600
cctggctccg tgggtcctgc tggtcctagg ggccctgctg gtccttctgg ccctgctgga   3660
aaagatggtc gcactggaca tcctggtaca gttggacctg ctggcattcg aggccctcag   3720
ggtcaccaag gccctgctgg cccccctggt cccctggcc ctcctggacc tcaggtgta    3780 agcggtggtg gttatgactt tggttacgat ggagacttct acagggctga ccagcctcgc   3840
tcagcacctt ctctcagacc caaggactat gaagttgatg ctactctgaa gtctctcaac   3900
aaccagattg agacccttct tactcctgaa ggctctagaa agaacccagc tcgcacatgc   3960
cgtgacttga gactcagcca cccagagtgg agcagtggtt actactggat tgaccctaac   4020
caaggatgca ctatggatgc tatcaaagta tactgtgatt tctctactgg cgaaacctgt   4080
atccgggccc aacctgaaaa catcccagcc aagaactggt ataggagctc caaggacaag   4140
aaacacgtct ggctaggaga aactatcaat gctggcagcc agtttgaata taatgtagaa   4200
ggagtgactt ccaaggaaat ggctacccaa cttgccttca tgcgcctgct ggccaactat   4260
gcctctcaga acatcaccta ccactgcaag aacagcattg catacatgga tgaggagact   4320
ggcaacctga aaaaggctgt cattctacag ggctctaatg atgttgaact tgttgctgag   4380
ggcaacagca ggttcactta cactgttctt gtagatggct gctctaaaaa gacaaatgaa   4440
tggggaaaga caatcattga atacaaaaca aataagccat cacgcctgcc cttccttgat   4500
```

| | |
|---|---|
| attgcacctt tggacatcgg tggtgctgac caggaattct ttgtggacat tggcccagtc | 4560 |
| tgtttcaaat aaatgaactc aatctaaatt aaaaaagaaa gaaatttgaa aaaactttct | 4620 |
| ctttgccatt tcttcttctt cttttttaac tgaaagctga atccttccat ttcttctgca | 4680 |
| catctacttg cttaaattgt gggcaaaaga gaaaaagaag gattgatcag agcattgtgc | 4740 |
| aatacagttt cattaactcc ttcccccgct cccccaaaaa tttgaatttt ttttcaaca | 4800 |
| ctcttcaccc tgttatggaa aatgtcaacc tttgtaagaa aaccaaaata aaaattgaaa | 4860 |
| aataaaaacc ataaacattt gcaccacttg tggcttttga atatcttcca cagagggaag | 4920 |
| tttaaaaccc aaacttccaa aggtttaaac tacctcaaaa cactttccca tgagtgtgat | 4980 |
| ccacattgtt aggtgctgac ctagacagag atgaactgag gtccttgttt tgttttgttc | 5040 |
| ataatacaaa ggtgctaatt aatagtattt cagatacttg aagaatgttg atggtgctag | 5100 |
| aagaatttga gaagaaatac tcctgtattg agttgtatcg tgtggtgtat ttttaaaaa | 5160 |
| atttgattta gcattcatat tttccatctt attcccaatt aaaagtatgc agattatttg | 5220 |
| cccaaatctt cttcagattc agcatttgtt ctttgccagt ctcattttca tcttcttcca | 5280 |
| tggttccaca gaagctttgt ttcttgggca agcagaaaaa ttaaattgta cctatttgt | 5340 |
| atatgtgaga tgtttaaata aattgtgaaa aaatgaaat aaagcatgtt tggttttcca | 5400 |
| aaagaacata t | 5411 |

<210> SEQ ID NO 9
<211> LENGTH: 4467
<212> TYPE: DNA
<213> ORGANISM: Homo sapiens

<400> SEQUENCE: 9

| | |
|---|---|
| atggctcacg ctcgtgttct cctcctcgct ctcgctgttt tggcaacagc tgctgtggct | 60 |
| gtggcttcta gttcttcttt tgctgattca aaccctatta gacctgttac tgatagagca | 120 |
| gcttccactt tggctcaatt gcaagaggag ggccaggttg agggccaaga tgaggatatc | 180 |
| cctccaatta catgcgtgca aaatggcttg cgttaccacg ataggggatgt gtggaaacct | 240 |
| gaaccttgtc gtatctgtgt gtgtgataac ggcaaggtgc tctgcgatga tgttatctgc | 300 |
| gatgagacaa aaaattgccc tggcgctgaa gttcctgagg gcgagtgttg ccctgtgtgc | 360 |
| cctgatggtt ccgagtcccc aactgatcag gaaactactg gcgtggaggg cccaaaagga | 420 |
| gatactggtc cacgtggtcc tagggggtcca gcaggtcctc caggtagaga tggtattcca | 480 |
| ggccagcctg gattgccagg accaccaggc ccacctggcc caccaggacc tcctggtctt | 540 |
| ggtggaaatt tcgctccaca actctcttat ggctatgatg agaagtcaac aggtggtatt | 600 |
| tccgttccag gtcctatggg accatccgga ccaagaggtc tcccaggtcc tccaggtgct | 660 |
| cctggacctc aaggctttca aggacctcca ggcgaaccag agaaccaggg cgcttctgga | 720 |
| ccaatgggcc caaggggacc acctggccca ccaggaaaaa atggcgatga tggcgaagct | 780 |
| ggaaagcctg gtcgtcctgg agagagaggt cctcctggcc cacagggtgc aagaggcttg | 840 |
| ccaggaactg ctggcttgcc tggaatgaag ggacataggg gcttctccgg cctcgatggc | 900 |
| gctaaggtg atgctggccc tgctggacca aaggcgagc caggttcccc tggagaaaac | 960 |
| ggtgctcctg gacaaatggg tcctcgtgga cttccaggag aaaggggtcg tccaggcgct | 1020 |
| ccaggaccag caggtgctag ggaaacgat ggtgcaacag cgctgctgg ccctcctggc | 1080 |
| ccaactggtc ctgctggccc tccaggattc ccaggcgcag ttggagctaa aggagaagca | 1140 |
| ggaccacagg gccctagggg ttctgaagga cctcagggtg ttagaggtga accaggtcct | 1200 |

```
ccaggcccag ctggagcagc tggtccagca ggaaatccag gtgctgatgg tcaacctgga    1260
gctaagggcg ctaatggcgc accaggtatc gcaggcgcac caggttttcc tggcgctaga    1320
ggcccaagtg gtcctcaagg accaggtgga ccaccaggtc caaaaggcaa ttctggcgaa    1380
cctggcgctc caggttctaa aggagatact ggtgctaaag gcgaaccagg acctgttggt    1440
gttcagggtc ctcctggtcc tgctggagaa aaggaaaaa gaggtgctcg tggagaacca    1500
ggaccaactg gacttcctgg acctcctggt gaacgtggcg gacctggctc aaggggtttc    1560
cctggagctg atggagtggc aggtccaaaa ggccctgctg gagagagagg ttcaccaggt    1620
ccagctggtc ctaagggctc ccctggtgaa gcaggtagac caggcgaagc aggattgcca    1680
ggcgcaaagg gattgacagg ctctcctggt agtcctggcc cagatggaaa aacaggccca    1740
ccaggtccag caggacaaga tggacgtcca ggcccaccag gtcctcctgg agcaagggga    1800
caagctggcg ttatgggttt tccaggacct aaaggtgctg ctggagagcc aggaaaggca    1860
ggtgaaagag gagttcctgg tccaccagga gcagtgggtc ctgctggcaa agatggtgaa    1920
gctggagcac agggccctcc aggccctgct ggcccagctg gcgaacgtgg agaacaaggc    1980
ccagctggta gtccaggatt tcaaggattg cctggccctg ctggccctcc aggagaagca    2040
ggaaaacctg gagaacaagg agttcctggt gatttgggag cacctggacc ttcaggagca    2100
cgtggtgaaa gaggcttccc tggcgagagg ggtgttcaag gtccaccagg tccagcagga    2160
cctagaggtg ctaatggcgc tcctggcaac gatggagcaa aggtgatgc tggtgctcct    2220
ggcgcacctg gaagtcaggg tgctcctgga ttgcaaggaa tgcctggaga gagggtgct    2280
gctggcttgc caggcccaaa gggcgatagg ggtgatgctg gaccaaaagg tgctgatgga    2340
tccccaggaa aagatggagt tcgtggtctt actggcccaa tcggacctcc aggccctgct    2400
ggcgctccag gtgataaggg cgaaagtggc ccaagtggac ctgctggacc tactggtgct    2460
agaggtgcac ctggtgatag ggtgaacct ggaccacctg gtccagctgg ttttgctggt    2520
cctcctggag ctgatggaca acctggcgca aagggtgaac caggtgatgc tggcgcaaag    2580
ggagatgctg gtccacctgg acctgctggt ccagcaggcc ccctgggcc aatcggtaat    2640
gttggagcac caggtgctaa gggagctagg ggttccgctg gtccacctgg agcaacagga    2700
tttccaggcg ctgctggtag agttggccca ccaggcccat ccggaaacgc aggccctcct    2760
ggtcctccag gtcctgctgg caaggagggt ggcaaaggac caaggggcga aactggcccct    2820
gctggtagac ctggcgaagt tggccctcct ggaccaccag gtccagcagg agaaaaaggt    2880
tccccaggag ctgatggccc agctggtgct ccaggaactc caggccctca ggtattgct    2940
ggacagagag gcgttgtggg actccctggt caaaggggag agagaggatt tccaggcttg    3000
ccaggaccta gtggagaacc tggaaaacaa ggcccatcag gcgctagtgg agagcgtgga    3060
cctcctggcc ctatgggacc tcctggattg gctggcccac ctggcgaatc aggtcgtgaa    3120
ggcgcaccag cgcagaagg atcacctgga agagatggat ccctggtgc taaaggcgat    3180
cgtggagaaa ctggtccagc aggcccacca ggcgcaccag gtgcacctgg cgctccagga    3240
cctgtgggac cagctggaaa atccggagat aggggcgaga caggcccagc aggaccagct    3300
ggacctgttg gccctgctgg cgctcgtgga ccagcaggac ctcaaggacc aagggggat    3360
aaggagaaa caggcgaaca aggcgatagg ggcattaagg gtcataggg ttttagtggc    3420
ctccagggtc ctcctggccc acctggatca ccaggagaac agggaccatc tggtgcttcc    3480
ggcccagctg gtccaagagg acctccagga tcagctggtc cacctggaaa agatggtctt    3540
```

| | |
|---|---:|
| aacggtctcc caggaccaat cggccctcca ggacctagag gaagaacagg agatgctggc | 3600 |
| cctgttggcc ctccaggacc tcctggtcca ccaggtccac ctggtcctcc atcagctgga | 3660 |
| ttcgattttt catttcttcc acagccacca caagagaaag ctcacgatgg cggcagatat | 3720 |
| taccgtgctg atgatgctaa cgttgttagg gatagagatt tggaagtgga tacaactttg | 3780 |
| aaatccctct cccagcaaat tgaaaacatt agatctccag aaggttcacg taaaaaccca | 3840 |
| gctagaacat gtcgtgattt gaaaatgtgt cactccgatt ggaaaagtgg tgaatactgg | 3900 |
| attgatccaa atcagggctg taatctcgat gctatcaaag ttttctgtaa catggaaaca | 3960 |
| ggcgaaacat gcgtttatcc tactcaacct tccgtggctc agaaaaattg gtacatctca | 4020 |
| aaaaatccta agataagag gcacgtttgg ttcggtgaaa gtatgactga tggatttcaa | 4080 |
| tttgagtacg gcggtcaagg tagtgatcca gctgatgtgg ctattcaact cacattttg | 4140 |
| cgtcttatgt ccacagaggc atcacaaaac atcacttacc actgcaaaaa cagtgtggct | 4200 |
| tatatggatc aacaaacagg aaaccttaag aaggctcttc ttttgaaggg ctcaaacgag | 4260 |
| attgagatta gagcagaggg caactcaagg tttacttatt cagttactgt tgatggctgc | 4320 |
| acttcacata ctggcgcttg ggtaaaaaca gttatcgagt ataagactac aaaaacatca | 4380 |
| agactcccaa tcattgatgt tgctcctctc gatgttggcg ctcctgatca agagttcggt | 4440 |
| tttgatgtgg gcccagtttg tttcctc | 4467 |

<210> SEQ ID NO 10
<211> LENGTH: 4167
<212> TYPE: DNA
<213> ORGANISM: Homo sapiens

<400> SEQUENCE: 10

| | |
|---|---:|
| atggctcacg ctcgtgttct cctcctcgct ctcgctgttt tggcaacagc tgctgtggct | 60 |
| gtggcttcaa gttctagttt tgctgattcc aacccaattc gtccagttac tgatagagca | 120 |
| gcttccactt tggctcaatt gcttcaagaa gaaactgtga ggaagggccc tgctggcgat | 180 |
| aggggcccta ggggcgaaag gggtccacca ggacctccag gcagggatgg cgaagatggt | 240 |
| ccaactggcc ctcctggacc tcctggccct caggggccac ccggcttggg cggaaacttc | 300 |
| gcagctcaat acgatggcaa gggtgttggt cttggtcctg gtcctatggg cttgatggga | 360 |
| cctagaggcc cacctggtgc tgctggtgct cctggaccac agggttttca gggaccagct | 420 |
| ggcgagccag gagagccagg ccaaacagga ccagctggtg caaggggacc tgctggacct | 480 |
| cctggaaaag ctggtgaaga tggtcaccca ggcaaaccag gacgtcctgg cgaaagaggt | 540 |
| gttgttggac cacaaggcgc tagggatttt ccaggtacac ctggattgcc aggttttaag | 600 |
| ggcattcgtg gtcataacgg cctcgatgga ttgaagggac agcctggcgc acctggcgtt | 660 |
| aagggtgaac tggagcacc aggtgaaaac ggtactcctg gccagactgg tgcaagagga | 720 |
| ctcccaggtg aaaggggtag agttggtgct cctggacctg ctggagctag gggtagtgat | 780 |
| ggtagtgttg gtcctgtggg ccctgctggt ccaatcggtt ccgctggccc acctggattc | 840 |
| ccaggcgctc caggacctaa aggagaaatc ggtgctgtgg gtaacgcagg tcctactggt | 900 |
| ccagcaggtc ctcgtggaga agtgggattg ccaggacttt ctggtccagt gggccctcca | 960 |
| ggcaaccctg gagctaacgg cttgacagga gctaaaggcg cagcaggact ccctggagtg | 1020 |
| gctggcgcac caggattgcc tggtccaagg ggtatcccag gcctgttgg cgcagctgga | 1080 |
| gctactggtg cacgtggact tgttggcgaa ccaggccctg ctggatcaaa aggcgagtct | 1140 |
| ggaaataagg gagaacctgg ttctgctgga cctcaaggtc ctcctggacc ttctggagaa | 1200 |

```
gaaggaaaaa ggggaccaaa tggcgaggct ggatcagcag gtccaccagg accacctgga   1260
cttcgtggat cccctggtag tagaggactt ccaggcgctg atggtagagc aggcgttatg   1320
ggaccaccag gaagtagagg agcatccggt ccagcaggag ttaggggtcc taacggagat   1380
gctggtagac caggtgaacc aggtcttatg ggcccaaggg gcctcccagg tagtccagga   1440
aatatcggcc ctgctggaaa agaaggccct gttggacttc caggtattga tggacgtcct   1500
ggccctattg gcccagcagg tgcaagagga gaacctggca atattggatt ccaggacca   1560 aagggtccaa caggcgatcc tggaaaaaat ggagataagg gtcatgctgg attggcaggc   1620
gcaaggggcg ctcctggtcc agatggaaac aacggcgcac agggtccacc tggccctcag   1680
ggtgttcaag gcggaaaagg cgaacaaggc ccagctggac caccaggctt tcaaggcttg   1740
ccaggaccaa gtggtccagc aggtgaagtt ggcaagccag gcgagcgtgg acttcatggc   1800
gagtttggac tccctggacc agcaggacca aggggtgaaa gaggccctcc tggagagagt   1860
ggcgctgctg gaccaacagg cccaatcggt agtagaggtc ctagtggacc tccaggccca   1920
gatggaaata agggtgaacc aggagttgtg ggcgctgttg gaacagctgg tccttcagga   1980
ccatcaggac tcccaggcga gagggcgct gctggcattc tggaggaaa aggtgaaaaa   2040 ggcgaacctg gcctccgtgg cgaaatcgga atcctggac gtgatggtgc tcgtggtgca   2100
cacggcgctg tgggcgctcc aggccctgct ggtgctactg gtgatagagg agaggctggc   2160
gcagctggcc cagcaggtcc tgctggccca agggggtagtc ctggtgaaag aggcgaagtt   2220
ggacctgctg gccctaacgg ctttgctggc cctgctggag cagcaggtca acctggcgct   2280
aaaggtgaaa ggggcggaaa gggcccaaaa ggtgaaaatg gcgttgtggg accaactggt   2340
ccagtgggcg cagctggacc tgctggtcca aatggaccac caggaccagc aggtagtaga   2400
ggagatggtg gacctccagg aatgacaggt tttccaggtg ctgctggtag aacaggacct   2460
cctggtccta gtggtatttc tggtccacca ggaccaccag gtcctgctgg aaaagaagga   2520
ttgaggggtc cacgtggtga tcaaggacca gtgggcagaa ctggtgaagt tggcgcagtg   2580
ggaccacctg gtttgctgg agaaaagggc ccttctggag aggcaggaac agctggtcct   2640
cctggtacac ctggacctca aggactttg ggtgcacctg gtattctcgg attgccagga   2700
agtaggggcg aacgtggact tcctggcgtg gcaggagcag ttggagaacc tggccctctc   2760
ggaatcgcag gcccaccagg cgcaagagga ccaccaggag ctgttggatc accaggcgtg   2820
aatggtgcac ctggcgaggc tggtcgtgat ggaaacccag gaaatgatgg cccaccagga   2880
agagatggtc aacctggaca caaggcgag agggctacc caggaaatat tggcccagtt   2940
ggtgctgctg gcgcaccagg cccacacggt ccagttggac cagcaggaaa acacggtaat   3000
cgtgccgaaa caggcccttc aggcccagtg ggacctgctg gtgctgttgg cccaagagga   3060
ccatctggac ctcaaggcat tagaggcgat aagggagagc ctggcgaaaa aggacctaga   3120
ggcttgcctg gttttaaagg acacaacggt ctccaaggac ttccaggtat cgctggtcat   3180
catggagatc agggtgctcc tggatcagtg ggtccagcag gtcctagagg cccagcaggc   3240
ccttccggtc cagcaggaaa ggatggacgt actggccacc ctggaactgt gggccctgct   3300
ggaattagag gtcctcaagg tcatcagggc cctgctggcc ctccaggtcc accaggtcct   3360
ccaggcccac caggagtttc aggtggtggt tacgattttg gttacgatgg tgattttac    3420 cgtgctgatc aacctagaag tgctccttct ctccgtccta agattatga agttgatgct   3480 actttgaaat cacttaacaa ccagattgag actcttctca cacctgaggg atcaagaaag   3540
```

| | |
|---|---|
| aatccagcac gtacatgccg tgatctcaga cttagtcacc cagagtggtc aagtggctat | 3600 |
| tattggattg atcctaatca gggttgtaca atggaggcta tcaaagttta ctgtgatttt | 3660 |
| ccaactggag agacatgtat tagggcacaa cctgagaaca ttccagctaa aaattggtat | 3720 |
| cgttcctcta aagataagaa acatgtttgg ctcggagaga ctattaacgc tggttctcag | 3780 |
| ttcgagtata atgttgaggg cgttacttct aaagagatgg caactcagct cgcttttatg | 3840 |
| agattgctcg ctaactacgc atcccaaaac atcacttatc actgcaaaaa ttccattgca | 3900 |
| tatatggatg aggagacagg aaatttgaag aaagcagtta ttctccaagg tagtaacgat | 3960 |
| gttgagcttg tggctgaggg aaatagtaga ttcacttaca cagttttggt ggatggatgc | 4020 |
| tcaaagaaaa ctaatgagtg gggcaagaca atcattgagt acaagacaaa taagccttct | 4080 |
| aggctcccat ttctcgatat tgcacctctt gatatcggag gagctgatca cgagtttttt | 4140 |
| gttgatatcg gacctgtttg tttttaag | 4167 |

<210> SEQ ID NO 11
<211> LENGTH: 1633
<212> TYPE: DNA
<213> ORGANISM: Artificial sequence
<220> FEATURE:
<223> OTHER INFORMATION: Synthetic sequence containing the coding
      regions of the vascular signal sequence of barley gene for Thiol
      protease aleurain precursor fused to the human Prolyl
      4-hydroxylase beta subunit and flanking regions

<400> SEQUENCE: 11

| | |
|---|---|
| ctcgagtaaa ccatggctca tgctagggtt ttgcttttgg ctcttgctgt tcttgctact | 60 |
| gctgctgttg ctgtggcttc ttcttcatct ttcgctgatt ctaacccaat taggccagtg | 120 |
| actgatagag ctgcttctac tcttgctcaa ttggtcgaca tggatgctcc agaagaggag | 180 |
| gatcacgttc ttgtgcttag gaagtctaac ttcgctgaag ctcttgctgc tcacaagtac | 240 |
| cttcttgtgg agttttatgc tccttggtgc ggacattgca aagctcttgc tccagagtat | 300 |
| gctaaggctg ctggaaagtt gaaggctgag ggatctgaaa ttaggcttgc taaagtggat | 360 |
| gctactgagg agtctgatct tgctcaacag tacggagtta ggggataccc aactattaag | 420 |
| ttcttcagga acgagataca tgcttctcca aaggagtata ctgctggaag ggaggctgat | 480 |
| gatattgtga actggcttaa gagagaact ggaccagctg ctactactct tccagatgga | 540 |
| gctgctgcta atctcttgt ggagtcatct gaggtggcag tgattggatt cttcaaggat | 600 |
| gtggagtctg attctgctaa gcagttcctt caagctgctg aggctattga tgatattcca | 660 |
| ttcggaatta cttctaactc tgatgtgttc tctaagtacc agcttgataa ggatggagtg | 720 |
| gtgctttca agaaattcga tgagggaagg aacaatttcg agggagaggt gacaaaggag | 780 |
| aaccttcttg atttcattaa gcacaaccag cttccacttg tgattgagtt cactgagcag | 840 |
| actgctccaa agattttcgg aggagagatt aagactcaca ttcttcttt ccttccaaag | 900 |
| tctgtgtctg attacgatgg aaagttgtct aacttcaaga ctgctgctga gtctttcaag | 960 |
| ggaaagattc tttttcatttt cattgattct gatcacactg ataaccagag gattcttgag | 1020 |
| ttcttcggac ttaagaagga agagtgccca gctgttaggc ttattactct tgaggaggag | 1080 |
| atgactaagt acaagccaga gtctgaagaa cttactgctg agaggattac tgagttctgc | 1140 |
| cacagattcc ttgagggaaa gattaagcca caccttatgt ctcaagagct tccagaggat | 1200 |
| tgggataagc agccagttaa ggtgttggtg ggtaaaaact cgaggatgt ggctttcgat | 1260 |
| gagaagaaga acgtgttcgt ggagttctac gcaccttggt gtggtcactg taagcagctt | 1320 |

```
gctccaattt gggataagtt gggagagact tacaaggatc acgagaacat tgtgattgct    1380
aagatggatt ctactgctaa cgaggtggag gctgttaagg ttcactcttt cccaactttg    1440
aagttcttcc cagcttctgc tgataggact gtgattgatt acaacggaga aaggactctt    1500
gatggattca agaagttcct tgagtctgga ggacaagatg gagctggaga tgatgatgat    1560
cttgaggatt tggaagaagc tgaggagcca gatatggagg aggatgatga tcagaaggct    1620
gtgtgatgag ctc                                                      1633
```

<210> SEQ ID NO 12
<211> LENGTH: 1723
<212> TYPE: DNA
<213> ORGANISM: Artificial sequence
<220> FEATURE:
<223> OTHER INFORMATION: Synthetic sequence containing the coding
regions of the vascular signal sequence of barley gene for Thiol
protease aleurain precursor fused to the human Prolyl
4-hydroxylase alpha-1 subunit and flanking regions

<400> SEQUENCE: 12

```
ctcgagtaaa ccatggctca tgctagggtt ttgcttttgg ctcttgctgt tcttgctact    60
gctgctgttg ctgtggcttc ttcttcatct ttcgctgatt ctaacccaat taggccagtg   120
actgatagag ctgcttctac tcttgctcaa ttggtcgaca tgcacccagg attcttcact   180
tctattggac agatgactga tcttattcac actgagaagg atcttgtgac ttctcttaag   240
gattacatta aggctgagga ggataagttg gagcagatta agaagtgggc tgagaagttg   300
gataggctta cttctactgc tacaaaagat ccagagggat tcgttggtca tccagtgaac   360
gctttcaagt tgatgaagag gcttaacact gagtggagtg agcttgagaa ccttgtgctt   420
aaggatatgt ctgatggatt catttctaac cttactattc agaggcagta cttcccaaat   480
gatgaggatc aagtgggagc tgctaaggct cttcttaggc ttcaggatac ttacaacctt   540
gatactgata caatttctaa gggaaaacctt ccaggagtta agcacaagtc tttccttact   600
gctgaggatt gcttcgagct tggaaaggtt gcatacactg aggctgatta ctaccacact   660
gagctttgga tggaacaagc tcttaggcaa cttgatgagg agagatttc tactattgat   720 aaggtgtcag tgcttgatta ccttttcttac gctgtgtacc agcagggtga tcttgataag   780
gctcttttgc ttactaagaa gttgcttgag cttgatccag aacatcagag ggctaacgga   840
aaccttaagt acttcgagta cattatggct aaggaaaagg atgtgaacaa gtctgcttct   900
gatgatcagt ctgatcaaaa gactactcca aagaagaagg gagtggctgt tgattatctt   960
cctgagaggc agaagtatga gatgttgtgt aggggagagg gtattaagat gactccaagg   1020
aggcagaaga agtgttctg caggtatcac gatggaaaca ggaacccaaa gttcattctt   1080
gctccagcta agcaagaaga tgagtgggat aagccaagga ttattaggtt ccacgatatt   1140
atttctgatg ctgagattga gattgtgaag gatcttgcta agccaagact taggagggct   1200
actatttcta accctattac tggtgatctt gagactgtgc actacaggat ttctaagtct   1260
gcttggcttt ctggatacga gaacccagtg gtgtctagga ttaacatgag gattcaggat   1320
cttactggac ttgatgtgtc tactgctgag gagcttcaag ttgctaacta cggagttgga   1380
ggacaatatg agccacactt cgatttcgct aggaaggatg agccagatgc ttttaaggag   1440
cttggaactg gaaacaggat tgctacttgg ctttttctaca tgtctgatgt ttctgctgga   1500
ggagctactg ttttcccaga agtgggagct tctgtttggc caaagaaggg aactgctgtg   1560
ttctggtaca acctttttcgc ttctggagag ggagattact ctactaggca tgctgcttgc   1620
```

```
ccagttcttg ttggaaacaa gtgggtgtca aacaagtggc ttcatgagag gggacaagag    1680
tttagaaggc catgcactct ttctgagctt gagtgatgag ctc                      1723

<210> SEQ ID NO 13
<211> LENGTH: 2888
<212> TYPE: DNA
<213> ORGANISM: Artificial sequence
<220> FEATURE:
<223> OTHER INFORMATION: Synthetic sequence containing the coding
      regions of the vascular signal sequence of barley gene for Thiol
      protease aleurain precursor fused to the human Lysyl hydroxylase 3
      and flanking regions

<400> SEQUENCE: 13
gcgaattcgc tagctatcac tgaaaagaca gcaagacaat ggtgtctcga tgcaccagaa      60
ccacatcttt gcagcagatg tgaagcagcc agagtggtcc acaagacgca ctcagaaaag    120
gcatcttcta ccgacacaga aaagacaaac cacagctcat catccaacat gtagactgtc    180
gttatgcgtc ggctgaagat aagactgacc ccaggccagc actaaagaag aaataatgca    240
agtggtccta gctccacttt agctttaata attatgtttc attattattc tctgcttttg    300
ctctctatat aaagagcttg tattttcatt tgaaggcaga ggcgaacaca cacacagaac    360
ctccctgctt acaaaccaga tcttaaacca tggctcacgc tagggttttg cttcttgctc    420
ttgctgttct tgctactgct gctgttgctg tggcttcttc aagttctttc gctgattcta    480
acccaattag gccagtgact gatagagctg cttctactct tgctcaattg agatctatgt    540
ctgatagacc aaggggaagg gatccagtta atccagagaa gttgcttgtg attactgtgg    600
ctactgctga gactgaagga taccttagat tccttaggag tgctgagttc ttcaactaca    660
ctgtgaggac tcttggactt ggagaagaat ggagggagg agatgttgct agaactgttg    720
gaggaggaca gaaagtgaga tggcttaaga agagatggga gaagtacgct gatagggagg    780
atatgattat tatgttcgtg gattcttacg atgtgattct tgctggatct ccaactgagc    840
ttttgaagaa attcgttcag tctggatcta ggcttctttt ctctgctgag tctttttgtt    900
ggccagaatg gggacttgct gagcaatatc cagaagtggg aactggaaag agattcctta    960
actctggagg attcattgga ttcgctacta ctattcacca gattgtgagg cagtggaagt   1020
acaaggatga cgatgatgat cagcttttct cactaggct ttaccttgat ccaggactta   1080
gggagaagtt gtctcttaac cttgatcaca agtctaggat tttccagaac cttaacggtg   1140
ctcttgatga ggttgtgctt aagttcgata ggaacagagt gaggattagg aacgtggctt   1200
acgatactct tccattgtg gtgcatgaa acggaccaac aaaactccag cttaactacc   1260
ttggaaacta cgttccaaac ggatggactc agaaggagg atgtggattc tgcaatcagg   1320
ataggagaac tcttccagga ggacaaccac accaagagt tttccttgct gtgttcgttg   1380
aacagccaac tccattcctt ccaagattcc ttcagaggct tcttcttttg gattacccac   1440
cagatagggt gacactttc cttcacaaca acgaggtttt ccacgagcca cacattgctg   1500
attcttggcc acagcttcag gatcatttct ctgctgtgaa gttggttggt ccagaagaag   1560
ctctttctcc aggagaagct agggatatgg ctatggattt gtgcaggcag gatccagagt   1620
gcgagttcta cttctctctt gatgctgatg ctgtgcttac taaccttcag actcttagga   1680
ttcttattga ggagaacagg aaagtgattg ctccaatgct ttctaggcac ggaaagttgt   1740
ggtctaattt ctgggggtgct cttttctcctg atgagtacta cgctagatca gaggactacg   1800
tggagcttgt tcagagaaag agagtgggag tttggaacgt tccttatatt tctcaggctt   1860
```

```
acgtgattag gggagatact cttaggatgg agcttccaca gagggatgtt ttctctggat   1920
ctgatactga tccagatatg gctttctgca agtctttcag ggataaggga attttccttc   1980 accttctaa  ccagcatgag ttcggaagat tgcttgctac ttcaagatac gatactgagc   2040
accttcatcc tgatctttgg cagattttcg ataacccagt ggattggaag gagcagtaca   2100
ttcacgagaa ctactctagg gctcttgaag gagaaggaat tgtggagcaa ccatgcccag   2160
atgtttactg gttcccactt ctttctgagc aaatgtgcga tgagcttgtt gctgagatgg   2220
agcattacgg acaatggagt ggaggtagac atgaggattc taggcttgct ggaggatacg   2280
agaacgttcc aactgtggat attcacatga agcaagtggg atacgaggat caatggcttc   2340
agcttcttag gacttatgtg ggaccaatga ctgagtctct tttcccagga taccacacta   2400
aggctagggc tgttatgaac ttcgttgtga ggtatcgtcc agatgagcaa ccatctctta   2460
ggccacacca cgattcttct actttcactc ttaacgtggc tcttaaccac aagggacttg   2520
attatgaggg aggaggatgc cgtttcctta gatacgattg cgtgatttct tcaccaagaa   2580
agggatgggc tcttcttcat ccaggaaggc ttactcatta ccacgaggga cttccaacta   2640
cttggggaac tagatatatt atggtgtctt tcgtggatcc atgactgctt taatgagata   2700
tgcgagacgc ctatgatcgc atgatatttg ctttcaattc tgttgtgcac gttgtaaaaa   2760
acctgagcat gtgtagctca gatccttacc gccggtttcg gttcattcta atgaatatat   2820
cacccgttac tatcgtattt ttatgaataa tattctccgt tcaatttact gattgtccag   2880
aattcgcg                                                            2888

<210>  SEQ ID NO 14
<211>  LENGTH: 45
<212>  TYPE: PRT
<213>  ORGANISM: Artificial Sequence
<220>  FEATURE:
<223>  OTHER INFORMATION: Vacuolar targeting sequence of the thiol
       protease aleurain precursor (NCBI accession P05167 GI:113603)

<400>  SEQUENCE: 14

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Ala
        35                  40                  45
```